(12) United States Patent
Song et al.

(10) Patent No.: US 11,578,137 B2
(45) Date of Patent: Feb. 14, 2023

(54) ANTI-C5 ANTIBODIES AND USES THEREOF

(71) Applicant: The Trustees of the University of Pennsylvania, Philadelphia, PA (US)

(72) Inventors: Wenchao Song, Bryn Mawr, PA (US); Sayaka Sato, Philadelphia, PA (US); Takashi Miwa, Bala Cynwyd, PA (US); Damodar Gullipalli, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 116 days.

(21) Appl. No.: 16/491,675

(22) PCT Filed: Mar. 6, 2018

(86) PCT No.: PCT/US2018/021001
§ 371 (c)(1),
(2) Date: Sep. 6, 2019

(87) PCT Pub. No.: WO2018/165062
PCT Pub. Date: Sep. 13, 2018

(65) Prior Publication Data
US 2020/0385481 A1 Dec. 10, 2020

Related U.S. Application Data

(60) Provisional application No. 62/467,498, filed on Mar. 6, 2017.

(51) Int. Cl.
*A61K 39/00* (2006.01)
*C07K 16/28* (2006.01)

(52) U.S. Cl.
CPC .... *C07K 16/2896* (2013.01); *A61K 2039/505* (2013.01); *C07K 2317/24* (2013.01);
(Continued)

(58) Field of Classification Search
None
See application file for complete search history.

(56) References Cited

U.S. PATENT DOCUMENTS

2014/0314772 A1* 10/2014 Guo .................. A61P 37/02
424/139.1
2015/0239966 A1  8/2015 Baciu
(Continued)

FOREIGN PATENT DOCUMENTS

JP  2011529700  12/2011
JP  2016513088  5/2016
(Continued)

OTHER PUBLICATIONS

Kussie "A Single Engineered Amino Acid Substitution Changes Antibody Fine Specificity" J immunol 152(1):146-52 (Year: 1994).*
(Continued)

*Primary Examiner* — Aurora M Fontainhas
(74) *Attorney, Agent, or Firm* — Riverside Law LLP

(57) ABSTRACT

This invention relates to inhibition of the complement signaling using an anti-C5 antibody. Specifically, the invention relates to methods of treating a complement-mediated disease or complement-mediated disorder in an individual by contacting the individual with an anti-C5 antibody.

23 Claims, 33 Drawing Sheets
Specification includes a Sequence Listing.

(52) U.S. Cl.
CPC .... *C07K 2317/55* (2013.01); *C07K 2317/565* (2013.01); *C07K 2317/622* (2013.01)

(56) References Cited

U.S. PATENT DOCUMENTS

| | | | |
|---|---|---|---|
| 2016/0068592 A1 | 3/2016 | Chung | |
| 2016/0176954 A1 | 6/2016 | Ruike | |
| 2016/0200805 A1 | 7/2016 | Fung | |
| 2016/0229908 A1 | 8/2016 | Igawa | |
| 2016/0251433 A1 | 9/2016 | Andrien, Jr. | |
| 2016/0355580 A1 | 12/2016 | Rother | |
| 2017/0355756 A1* | 12/2017 | Julien | C12N 15/86 |

FOREIGN PATENT DOCUMENTS

| | | |
|---|---|---|
| RU | 2477137 | 3/2013 |
| WO | 2007103549 | 9/2007 |
| WO | 2011137395 | 11/2011 |
| WO | 2014110438 | 7/2014 |
| WO | 2016160756 | 10/2016 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*

Koenig "Mutational landscape of antibody variable domains reveals a switch modulating the interdomain conformational dynamics and antigen binding" PNAS E486-E495 (Year: 2017).*

Boerner et al., "Production of antigen-specific human monoclonal antibodies from in vitro-primed human splenocytes", J. Immunol., 1991, 147:86-95.

Brodeur et al., "Monoclonal Antibody Production Techniques and Applications", Dekker, Inc., New York, 1987, 51-63.

Fukuzawa et al., "Long lasting neutralization of C5 by SKY59, a novel recycling antibody, is a potential therapy for complement-mediated diseases", Sci Rep., 2017, 7:1080, 12 pages.

Hwang et al., "Immunogenicity of engineered antibodies", Method, 2005, 36:3-10.

International Preliminary Report on Patentability for PCT/US2018/021001 dated Sep. 10, 2019, 7 pages.

International Search Report for PCT/US2018/021001 dated Jun. 20, 2018, 3 pages.

Kozbor D et al., "A human hybrid myeloma for production of human monoclonal antibodies", J. Immunol., 1984, 133:3001-3005.

Thomas et al., "Inhibition of Complement Activity by Humanized anti-C5 Antibody and Single-Chain Fv", Mol Immunol., 1996, 33:1389-1401.

Written Opinion of the International Searching Authority for PCT/US2018/021001 dated Jun. 20, 2018, 6 pages.

Janus Asbjørn Schatz-Jakobsen et al., 2016, "Structural Basis for Eculizumab-Mediated Inhibition of the Complement Terminal Pathway", J Immunol, 197:337-344.

Rudikoff et al., 1981, "Single Amino Acid Substitution Altering Antigen-binding Specificity", Proc. Natl. Acad. Sci., 79:1979-1983.

* cited by examiner

Nucleic acid and amino acid sequence of VH of mAb 2G1. Signal peptide is underlined and CDR1, CDR2 and CDR3 sequences are bolded and highlighted in gray.

VH

```
              AACAACATCTGTCCAATGTCCCTCTCCACAGGCACTGAACACACTGACTCTAACC
atggatggagctgtatcatcctcttcctgtcagtaactgcaggtgtcctctctgag
 M  G  W  S  W  I  F  L  F  L  L  S  G  T  A  G  V  L  S  E
gtccagctgcaacagtctggacctgaagctgtgaagcctggggcttcagtgaagatatcc
 V  Q  L  Q  Q  S  G  P  E  L  V  K  P  G  A  S  V  K  I  S
tgcaaggcttctggatacacattcactgactacaatatggactggtgaagcagagccat
 C  K  A  S  G  Y  T  F  T  D  Y  N  L  D  W  V  K  Q  S  H
ggaaagagccttgagtggattggagatattagtcctaactatggttatactatctacaac
 G  K  S  L  E  W  I  G  D  I  S  P  N  Y  G  Y  T  I  Y  N
cagaaattcaaggacaaggccacattgactgtagacagcagtagcactatgcctacatg
 Q  K  F  K  D  K  A  T  L  T  V  D  R  S  S  S  T  A  Y  M
gagctccgcagctgacatctgaggacactgcagtctattactgtgcaagaaggga cattcg 
 E  L  R  S  L  T  S  E  D  T  A  V  Y  Y  C  A  R  R  D  I
cgttactccgtaattcctacaaatggtacttcgatgtctgggggcacagggaccacggtc
 R  Y  S  G  N  S  Y  K  W  Y  F  D  V  W  G  T  G  T  T  V
accgtctcctcagccaaaacaacagcccatcggtctatccactggcc (SEQ ID NO: 1)
 T  V  S  S  (SEQ ID NO: 2)
```

CDR1 (SEQ ID NO: 3)
CDR2 (SEQ ID NO: 4)
CDR3 (SEQ ID NO: 5)

Nucleic acid and amino acid sequence of VL of mAb 2G1. Signal peptide is underlined and CDR1, CDR2 and CDR3 sequences are bolded and highlighted in gray.

```
tcagttcctgccaggacacagtttagatatgaggttccaggttctgggctcctt
                  M  R  F  Q  V  Q  V  L  G  L  L
ctgctctgatctcaggtgccagtgtgatgtccagataaccagtccagtcctcatcttatctt
 L  L  W  I  S  G  A  Q  C  D  V  Q  I  T  Q  S  P  S  Y  L
gctgcatcctctggagaaaccattactattgcaggagcaagtaagagcataagcaaa
 A  A  S  P  G  E  T  I  T  I  N  C  R  T  S  K  S  I  S  K
tattagcctggtatcaagagacaaactggaaaactaataagcttcttatctactctgga
 Y  L  A  W  Y  Q  E  K  P  G  K  T  N  K  L  L  I  Y  S  G
tccacccttgcaatctggaattcctcaaggttcaggggcagtggatctggtacagatttc
 S  T  L  Q  S  G  I  P  S  R  F  R  G  S  G  S  G  T  D  F
actctcaccatcagtagcctggagcctgaagatttgcaatgtattactgtcaacaacat
 T  L  T  I  S  S  L  E  P  E  D  F  A  M  Y  Y  C  Q  Q  H
aatgaataccctacacgttcggagggggacaggcaccgtggaaataaaacgggctgatgct (SEQ ID NO: 7)
 N  E  Y  P  Y  T  F  G  G  G  T  K  L  E  I  K
gcacca (SEQ ID NO: 6)
```

CDR1 (SEQ ID NO: 8)
CDR2 (SEQ ID NO: 9)
CDR3 (SEQ ID NO: 10)

Figure 13

Nucleic acid and amino acid sequence of VH of mAb 8E1. Signal peptide is underlined and CDR1, CDR2 and CDR3 sequences are bolded and highlighted in gray.

```
AGCCTCCATCAGAGCatggctgtcctgggctgcttctctgcgctgtgacttcccaagc
                M  A  V  L  G  L  L  L  C  L  V  T  F  P  S
tgtgtcctgtcccagtgcagctgaaggagtcaggacctggcctggtggcgccctcacag
 C  V  L  S  Q  C  Q  L  K  E  S  G  P  G  L  V  A  P  S  Q
agcctgtccatcacatgcaccgtctcagggtctccctttaaacaactatggaatacactgg   CDR1 (SEQ ID NO: 13)
 S  L  S  I  T  C  T  V  S  G  F  P  L  N  N  Y  G  I  H  W
gttcgccagcctccaggaaaggtctggagtggctggtcgcagtgatatggagtgatggaaga   CDR2 (SEQ ID NO: 14)
 V  R  Q  P  P  G  K  G  L  E  W  L  A  V  I  W  S  D  G  R
acaacctataattcagctctcaactcagactgagcatcagcaaggacaactccaagagc
 T  T  Y  N  S  A  L  N  S  R  L  S  I  S  K  D  N  S  K  S
caagtttcttttaaaatgaacagtctccaactgatgacagcacagccatgtactattgtgcc
 Q  V  F  F  K  M  N  S  L  Q  T  D  D  T  A  M  Y  Y  C  A
agacatgatcggggggactatagtatgactactggggtcaaggaacctcagtcacc   CDR3 (SEQ ID NO: 15)
 R  H  D  G  R  G  D  Y  S  M  D  Y  W  G  Q  G  T  S  V  T
Gtctcctcagccaaaacaacacccccatca (SEQ ID NO: 12)
 V  S  S
```

Nucleic acid and amino acid sequence of VL of mAb 8E1.

```
atggggaaagcatcctctcttcagtctcttagagatgagacagacactcctgttatgg
                 M  E  T  D  T  L  L  L  W
gtactgctgctctgggccccttagttccagctcgtgatgacacagtctctctgttccta
 V  L  L  W  A  L  S  S  E  L  V  M  T  Q  S  P  A  S  L
gttgtatctctggggcagagggccaccatcatgcaggcaaaggtgtcagtaca   CDR1 (SEQ ID NO: 18)
 V  V  S  L  G  Q  R  A  T  I  S  C  R  A  S  K  G  V  S  T
tctgtctacagttatatgcactggtaccaacagaaaccaggacagccaccaaactcctc
 S  V  Y  S  Y  M  H  W  Y  Q  Q  K  P  G  Q  P  P  K  L  L
atctatcttgcatccaactagaatctggggtccctgcagttcagtggcagtgggtct   CDR2 (SEQ ID NO: 19)
 I  Y  L  A  S  N  L  E  S  G  V  P  A  R  F  S  G  S  G  S
gggacagacttctcctcaacatcctgtggaggaggatgctcaacctattacy
 G  T  D  F  S  L  N  I  H  P  V  E  E  D  A  A  T  Y  Y
tgtcagcaaagtgggagtttccgctcacgttcggtgctgggaccaagctggagctgaaa   CDR3 (SEQ ID NO: 20)
 C  Q  Q  S  G  E  L  P  L  T  F  G  A  G  T  K  L  E  L  K
cgggctgatgctgcaccaacaagggc (SEQ ID NO: 16)
 R
```

Figure 14

Nucleic acid and amino acid sequence of VH of mAb 4E7. CDR1, CDR2 and CDR3 sequences are bolded and highlighted in gray.

```
atggggaaacaacatatgtccaatgtcctctcctcagacactgaacacactgactctaacc
               M  S  P  Q  T  N  T  L  T  L  T
atgggatggagctggatcttctctttcctcctgtcagaaactgcaggagtcctctctgag
M  G  W  S  W  I  F  L  F  L  L  S  E  T  A  G  V  L  S  E
gtccagctgcaacaggggcttcagtgaagatgtcctgtaagactcctgactactcattc
V  Q  L  Q  Q  G  A  S  V  K  M  S  C  K  T  S  R  Y  S  F       CDR1 (SEQ ID NO: 23)
actgactacatcatgcactgggtgaagcagagacctgagtggattgga
T  D  Y  I  M  H  W  V  K  L  S  H  G  K  S  L  E  W  I  G
tatattaaccctaacaatggtactatctacaaccagaagttcaaggacaaggccaca
Y  I  N  P  N  N  G  T  I  Y  N  Q  K  F  K  D  K  A  T        CDR2 (SEQ ID NO: 24)
ttgactgtaaacagtcctcagcagcacatgtaatgtttcccagcgacatcggag
L  T  V  N  K  S  S  S  T  A  Y  M  E  F  R  S  L  I  T  S  E
gattctgcagtctattctgttcaagaggggtttattacggggtttgcttactgg
D  S  A  V  Y  F  C  S  R  G  G  Y  Y  R  G  F  A  Y  W        CDR3 (SEQ ID NO: 25)
ggccaaggacactggtcactgtctctgcagccaaacgacaccccatct (SEQ ID NO:21)
G  Q  G  T  L  V  T  V  S  A  (SEQ ID NO: 22)
```

Nucleic acid and amino acid sequence of VL of mAb 4E7.

```
atggggggaccaatattgaaaagaatagacctggttgtgaattatggcctggatttcactt
                       M  A  W  I  S  L
atactctctctcctggctcctcagctccagggctgtgtgactcaggaa
I  L  S  L  L  A  L  S  S  G  A  I  S  Q  A  V  V  T  Q  E
tctgcactgactccaccggtgaaacagtcacttgtcgctcaagtactggg
S  A  L  T  T  S  P  G  E  T  V  T  F  T  C  R  S  S  T  G        CDR1 (SEQ ID NO: 28)
gctgttacaaacagtaactatgccaagtggtccaagaaaccagatcatttttcact
A  V  T  N  S  N  Y  A  N  W  V  Q  E  K  P  D  H  F  F  T
ggtctaataggtgttaccaacaaggtgcctcagtgttcctgccgattctcaggctcc
G  L  I  G  V  T  N  N  R  P  G  V  P  A  R  F  S  G  S        CDR2 (SEQ ID NO: 29)
ctgattggagacaaggctgcctcacctcacggggcacagactgaggaggcaata
L  I  G  D  K  A  A  L  T  I  T  G  A  Q  T  E  D  E  A  I
tatttctgtgctctatgtacagcagtcactttggttgtcgtgaggaaccaaactgac
Y  F  C  A  L  W  Y  S  N  H  L  G  V  R  W  R  N  Q  T  D
tgtcctaggccagccagtcttcgccatcagt (SEQ ID NO: 26)
C  P  R  P  A  Q  V  F  A  I  S  (SEQ ID NO: 27)
```

Figure 15

Nucleic acid and amino acid sequence of VH of mAb 9G6. CDR1, CDR2 and CDR3 sequences are bolded and highlighted in gray.

```
atggggaaggagtgaccagttagtcttcctgatagtcagctgagcccaaagtgtccaagtcttagacatcatg
                                                                      M
gattgggtgtgtggaccttggtattcctgatagtcagctgagcccaaagtgtccaagtcttagacatcatc
 D  W  V  T  L  V  F  L  I  A  A  Q  S  A  Q  A  Q  I
cagttggtgcagtctggacctgagctgaagaagcctggagagacagtcaagatctcctgc
 Q  L  V  Q  S  G  P  E  L  K  K  P  G  E  T  V  K  I  S  C
aaggcttctggatataccttcacagaatatccaatgcactgggtgaagcaggctccagga
 K  A  S  G  Y  T  F  T  E  Y  P  M  H  W  V  K  Q  A  P  G
aagagtttcaagtggatgggcatcctatacaccggagaccaacatatgctgaa
 K  S  F  K  W  M  G  I  L  Y  T  D  G  E  P  T  Y  A  E
gagttcaagggacggtttgctttctcttggagacctgccagactgctatttgcag
 E  F  K  G  R  F  A  F  S  L  E  T  S  A  S  T  A  Y  L  Q
atcaacaacctcaaaaatgaggacactgccacactctcacagtctcatcagccaaaacaacccccatca
 I  N  N  L  K  N  E  D  T  A  T  Y  F  C  V  H  S  G  Y  V
ggctactggggccaaggcaccactctcacagtctcctcag (SEQ ID NO: 30)
 G  Y  W  G  Q  G  T  T  L  T  V  S  S  (SEQ ID NO: 31)
```

G Y T F T E Y P M H      CDR1 (SEQ ID NO: 32)
I L Y T D G E P T Y A E  CDR2 (SEQ ID NO: 33)
S G Y V                  CDR3 (SEQ ID NO: 34)

Nucleic acid and amino acid sequence of VL of mAb 9G6. CDR1, CDR2 and CDR3 sequences are bolded and highlighted in gray.

```
atggggtctaatcagcatcacactgaaaacacagatgtgccactcaggtc
                                    M  S  V  P  T  Q  V
ctggggttgctgctgctgtggttacaggtgacatccagatgactgactcagtct
 L  G  L  L  L  L  W  L  T  G  A  R  C  D  I  Q  M  T  Q  S
ccagctcccctatcagtgtctgcaccttcaccttcggcaagtgag
 P  A  S  L  S  A  S  V  G  E  T  V  T  F  T  C  R  A  S  E
attattacagtgttagttggtatcagcagaaaatctcctccagtcctg
 I  I  T  S  Y  L  Y  W  Y  Q  Q  K  S  P  Q  L  L
gtctctaatgcaaaaacttagcagagagggtgccatcaagttcagtgcagtggatca
 V  S  N  A  K  T  L  A  E  G  V  P  S  R  F  S  G  S  G  S
ggcacagatttctctgaagatcaatagcctgcagcctgaagatttggagttattac
 G  T  Q  F  S  L  K  I  N  S  L  Q  P  E  D  F  G  S  Y  Y
tgtcaacattattgtaatgtccacgttcggagggggaccaagctggaaataaaa
 C  Q  H  Y  Y  G  N  P  T  F  G  G  G  T  K  L  E  I  K
cgg (SEQ ID NO: 35)
 R  (SEQ ID NO: 36)
```

R A S E I I T S Y L Y    CDR1 (SEQ ID NO: 37)
N A K T L A E            CDR2 (SEQ ID NO: 38)
Q H Y Y G N P T          CDR3 (SEQ ID NO: 39)

Figure 16

Nucleic acid and amino acid sequence of VH of mAb 11C5. CDR1, CDR2 and CDR3 sequences are bolded and highlighted in gray.

```
acatgggrgctctgacagagaggaggccgtcctgagttcctcactcagtgatg
                                                   M
agcactgaacacggaccctgcaccatgaacttcgggctcagctgatttcctttgtcctt
 S  T  E  H  G  P  L  T  M  N  F  G  L  S  L  I  F  L  V  L
gttttaaaagtgtccagtgtgaagtgcaggtagtgagtctgggggagggcttagtgaag
 V  L  K  G  V  Q  C  E  V  Q  L  V  E  S  G  G  G  L  V  K
cctggagggtccctgaaactctcctgtgcagcctctgggattcacttcactactatgcc
 P  G  G  S  L  K  L  S  C  A  A  S  G F T F T Y A
atgtctggttccgcagaccctgcgaaaagaggtgatgtgtgcaacattagtgct
 M  S  W  V  R  Q  T  P  E  K  R  L  E  W  V  A T I S A
ggtggtactatcactgacacctattcagaatgtaaagggccgattcaccatctccagagac
 G G T I T D N V K G  R  F  T  I  S  R  D
aatgccaagaacaacctgtacttgcaaatgagcatcatcgaagtctgaggacacagccatg
 N  A  K  N  N  L  Y  L  Q  M  S  H  L  K  S  E  D  T  A  M
ttttactgtgcaagagatccgattactacggctagcccgttcggttgttactgggccaa
 F  Y  C  A  R D P D Y Y G R S P F A Y  W  G  Q
gggactctggtcactgtctctgcagccaaaacaaccacccccatca (SEQ ID NO: 40)
 G  T  L  V  T  V  S  A (SEQ ID NO: 41)
```

CDR1 (SEQ ID NO: 42)
CDR2 (SEQ ID NO: 43)
CDR3 (SEQ ID NO: 44)

Nucleic acid and amino acid sequence of VL of mAb 11C5. CDR1, CDR2 and CDR3 sequences are bolded and highlighted in gray.

```
atggggtggagccactgcttttttggattcagctgcagagtgaagatggtgttccactcagatactt
                                        M  V  F  T  P  Q  I  L
ggacttatgctttttgtctgttgactccaggagctgaagctagagagatggtgcccactcagtctcca
 G  L  M  L  F  W  I  S  A  S  R  G  E  I  V  L  T  Q  S  P
gccaccctgtctgtgtcctccaggagagctcagtcttcctgttgccagccaaagt
 A  T  L  S  V  T  P  G  E  S  V  S  L  S  C R A S Q S
attagcaacaactacctacagtggtatcaacaaaatcacagatgtctccaagacttctcatc
 I S N N L Q  W  Y  Q  Q  K  S  H  E  S  P  R  L  L  I
aaatatgcttccatctctggatccctccaggttcagtgcagtggatcaggg
 K Y A S Q S I S  G  I  P  S  R  F  S  G  S  G
acagattcactctcatcaacacagtgatatcaacagtgaagatttggaatgatatttctgt
 T  D  F  T  L  S  I  N  S  V  E  T  E  D  F  G  M  Y  F  C
caacagagtaacagctggcctctcacgttcggtgttgggagcaaagtggagctgaaacgg (SEQ ID NO: 45)
 Q Q S N S W P L T  F  G  G  G  T  K  V  E  L  K  R
                          (SEQ ID NO: 46)
```

CDR1 (SEQ ID NO: 47)
CDR2 (SEQ ID NO: 48)
CDR3 (SEQ ID NO: 49)

Figure 17

Nucleic acid and amino acid sequence of VH of mAb 11D9. CDR1, CDR2 and CDR3 sequences are bolded and highlighted in gray.

```
atgggacatatgtcctcaccacagacactgaacactgactgactctaaccatggga
 M   G   H   M   S   P   Q   T   L   N   T   L   T   L   T   M   G
tggagctggatcttcctcttcctcctgtcaggaactgcaggtgtcctctctgaggtccag
 W   S   W   I   F   L   F   L   L   S   G   T   A   G   V   L   S   E   V   Q
ctgcaacaatctggacctgaggtggtgaagcctgggcttcagtgaagatatcctgtaag
 L   Q   Q   S   G   P   E   V   V   K   P   G   A   S   V   K   I   S   C   K
gcttctggatacacgttcactgactttyxatgaactgggtgaaacagagcacatgaaag     CDR1 (SEQ ID NO: 52)
 A   S   G   Y   T   F   T   D   F   Y   M   N   W   V   K   Q   S   H   G   K
agccttgagttgattggatatattaatcctaatgtgactagttacaacagaagaag        CDR2 (SEQ ID NO: 53)
 S   L   E   W   I   G   Y   I   N   P   N   N   G   D   T   S   Y   N   Q   K
ttcaagggcaaggccacatgactgtagacagcctctccaacagcctacatggagctc
 F   K   G   K   A   T   S   T   V   D   R   S   S   N   T   A   Y   M   E   L
cgcagctgacatctgaggactctgagtctattactgtgcaagactccatctctatggt       CDR3 (SEQ ID NO: 54)
 R   S   L   T   S   E   D   S   A   V   Y   Y   C   A   R   L   I   F   Y   G
aactggtactttgatgtctgggggacaggcaccacggtcaccgtctccagcaaaaca
 N   W   Y   F   D   V   W   G   T   G   T   T   V   T   V   S   S   A   K   T    (SEQ ID NO: 51)
acagccccatcg (SEQ ID NO: 50)
```

Nucleic acid and amino acid sequence of VL of mAb 11D9. CDR1, CDR2 and CDR3 sequences are bolded and highlighted in gray.

```
atgggaataattagccagagactgagatgaaacaaaatggattttcagatgcagatt
                                    M   D   F   Q   M   Q   I
atcagcttgctgctaatcagtgtcacagtcatagtgtctaatggagaaattgtgctcacc
 I   S   L   L   L   I   S   V   T   V   I   V   S   N   G   E   I   V   L   T
cagtctccaccatggctgtcatctccggggagaagatcactcacctgcagtgcc
 Q   S   P   P   M   A   A   S   P   G   E   K   I   T   I   T   C   S   A
agctcaagtataagttccaattacgtgcattggtatcagcagaagccagatttctcccct     CDR1 (SEQ ID NO: 57)
 S   S   S   I   S   S   N   Y   V   H   W   Y   Q   Q   K   P   G   F   S   P
aaactctgatttataggacctggacatccaatctctggagtccctgacttcgttcagtggc    CDR2 (SEQ ID NO: 58)
 K   L   L   I   Y   R   T   S   N   L   A   S   G   V   P   V   R   F   S   G
agtggtctgggacctcttactctctcactatatccgtgaagatgttgcc
 S   G   S   G   T   S   Y   S   L   T   I   G   T   M   E   A   E   D   V   A
acttactgtcagcaggtactagtataccgtccctggacgttcggtggaggcaccaaggtg      CDR3 (SEQ ID NO: 59)
 T   Y   Y   C   Q   Q   G   T   S   I   P   W   T   F   G   G   G   T   K   V
gaaattaatcgg (SEQ ID NO: 55)
 E   I   N   R (SEQ ID NO: 56)
```

Figure 18

These sequences were used to construct chimeric (mouse variable region + human constant region) and humanized (humanized mouse variable region + human constant region) anti-human C5 antibody (2G1).

Amino acid sequence of human IgG4 Constant Heavy chain region with S228P mutation. Proline residue at position 228 is highlighted in gray.

ASTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCP
APEFLGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSPG
K (SEQ ID NO: 60)

Amino acid sequence of human Kappa Constant Light region

TVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC (SEQ ID NO: 61)

Figure 19 humanized 2G1 VH-11801

```
cagcatatgatcagtgtcctctccaagtccttgaacatagactctaaccatgactggacc
                                              M  D  W  T
tgggtcttctctcctgtcagtaactgcaggtgtccactcccaggttcagctggtg
 W  V  F  L  L  S  V  T  A  G  V  H  S  Q  V  Q  L  V
cagtctggagctgaggtgaagaagcctgggcctcagtgaaggtctcctgcaaggcttct
 Q  S  G  A  E  V  K  K  P  G  A  S  V  K  V  S  C  K  A  S
ggatacacaatcacagactacaatttggactgggtgcgacaggcccctggacaagggctt    CDR1 (SEQ ID NO: 64)
 G  Y  T  I  T  D  Y  N  L  D  W  V  R  Q  A  P  G  Q  G  L
gagtggatgggagatattagtcctaactatggttatactatctacaaccagaaattcaag    CDR2 (SEQ ID NO: 65)
 E  W  M  G  D  I  S  P  N  Y  G  Y  T  I  Y  N  Q  K  F  K
gacagagtcaccatgaccacagaccacatccagcacacagcctacatggagctgagagc
 D  R  V  T  M  T  T  D  T  S  T  S  T  A  Y  M  E  L  R  S
ctgagatctgacgacacggccgtgtattactgtgcgagaagggacattcgttactccggt    CDR3 (SEQ ID NO: 66)
 L  R  S  D  D  T  A  V  Y  Y  C  A  R  R  D  I  R  Y  S  G
aattcctacaaatggtacttcgatgtctggggccaagggacaatggtcaccgtctcttca  (SEQ ID NO: 62)
 N  S  Y  K  W  Y  F  D  V  W  G  Q  G  T  M  V  T  V  S  S  (SEQ ID NO: 63)
```

Figure 22 humanized 2G1 VH-16901 cagcatatgatcagtgtcctctccaagtccttgaacatagactctaaccatgactggacc
                                                M   D   W   T
tgggtctttctcctcctgtcagtaactgcagtgtccactcccaggtgtcagctggtg
 W  V  F  L  F  L  L  S  V  T  A  G  V  H  S   Q  V  Q  L  V
cagtctggggctgaggtgaagaagcctggggtcctcggtgaaggtctcctgcaaggcttct
 Q  S  G  A  E  V  K  K  P  G  S  S  V  K  V   S  C  K  A  S
ggatacacaatcacagactacaatttggactggtgcgacaggcccctggacaagggctt
 G  Y  T  I  T  D  Y  N  L  D  W  V  R  Q  A   P  G  Q  G  L      CDR1 (SEQ ID NO: 69)
gagtggatgggagatattagtcctaactatggttatactatctacaaccagaaattcaag
 E  W  M  G  D  I  S  P  N  Y  G  Y  T  I  Y   N  Q  K  F  K      CDR2 (SEQ ID NO: 70)
gacagagtcacgattaccgcggacgaatccacgagcacctacatggagctgagcagc
 D  R  V  T  I  T  A  D  E  S  T  S  T  A  Y   M  E  L  S  S
ctgagatctgaggacacggctgtgtattactgtgcgagagggacattcgttactccggt
 L  R  S  E  D  T  A  V  Y  Y  C  A  R  R  D   I  R  Y  S  G      CDR3 (SEQ ID NO: 67)
aattcctacaaatggtacttctgggggcaagggacaatggtcaccgtctcttca (SEQ ID NO: 68)
 N  S  Y  K  W  Y  F  D  V  W  G  Q  G  T  M   V  T  V  S  S Nucleic acid and amino acid sequence of VL of the humanized 2G1. CDR1, CDR2 and CDR3 sequences are bolded and highlighted in gray.

Figure 23 humanized 2G1 VL-1901

```
gtcagagccctggggaggaactgctcagttaggaccagagaggaaccatgaagcccagct
                                         M  E  A  P  A
cagctctcttcctgctactctggcttctcctgggagacatccaccggagacatccagttgacc
 Q  L  F  L  L  W  L  P  D  T  G  D  I  Q  L  T
cagtctccatcctccgtctgcatctgtaggagacagagtcaccatcacttgccaggaca
 Q  S  P  S  S  L  S  A  S  V  G  D  R  V  T  I  T  C  R  T    CDR1 (SEQ ID NO: 74)
agtaagagcataagcaaatattagcctggtatcagcaaaaccagggaaagcccctaag
 S  K  S  I  S  K  Y  L  A  W  Y  Q  Q  K  P  G  K  A  P  K
ctcctgatctattctgggatccaacctctgggtcccatcaaggttcagcggcagt
 L  L  I  Y  S  G  S  T  L  Q  S  G  V  P  S  R  F  S  G  S    CDR2 (SEQ ID NO: 75)
ggatctgggacagaattcactctcacatcagcctgagcctgaagattttgcaact
 G  S  G  T  E  F  T  L  T  I  S  S  L  Q  P  E  D  F  A  T
tattactgtcaacaacatgaataccgtacacgttttggccaggggaccaagctggag
 Y  Y  C  Q  Q  H  N  E  Y  P  Y  T  F  G  Q  G  T  K  L  E    CDR3 (SEQ ID NO: 76)
atcaaa  (SEQ ID NO: 72)
 I  K   (SEQ ID NO: 73)
```

| MG1 | MG2 | MG3 | MG4 | MG5 | MG6 | C5a | MG7 | CUB | C5d | CUB | MG8 | C345C |
|-----|-----|-----|-----|-----|-----|-----|-----|-----|-----|-----|-----|-------|

C5 β-chain ──────────────────────────────  C5 α-chain ──────────────────────────────

B

MG1:
QEQTYVISAPKIERVGASENIVIQVYGYTEAFDATISIKSYPDKKFSYSSGHVHLSSENKFQNSAIL
TIQPKQLPGGQNPVSYVYLEVVSKHFSKSKRMPITYD (SEQ ID NO:84)

MG2:
NGFLFIHTDKPVYTPDQSVKVRVYSLNDDLKPAKRETVLTFIDPEGSEVDMVEEIDHIGIISFPDFK
IPSNPRYGMWTIKAKYKEDFSTTGTAYFEVKEYV (SEQ ID NO:85)

MG3:
LPHFSVSIEPEYNFIGYKNFKNEFEITIKARYFYNKVVTEADVYITFGIREDLKDDQKEMMQTAMQNT
MLINGIAQVTFDSETAVKELSYYSLEDLNNKYLYIAVTVIESTGGFSEEAEIPGIKYVLS (SEQ
ID NO:86)

MG4:
PYKLNLVATPLFLKPGIPYPIKVQVKDSLDQLVGGVPVTLNAQTIDVNQETSDLDPSKSVTRVDDGV
ASFVLNLPSGVTVLEFNVKTDAPDLPEENQAREGYRAIAYS (SEQ ID NO:87)

MG5:
SLSQSYLYIDWTDNHKALLVGEHLNIIVTPKSPYIDKITHYNYLILSKGKIIHFGTREKFSDASYQS
INIPVTQNMVPSSRLLVYYIVTGEQTAELVSDSVWLNIEEK (SEQ ID NO:88)

MG6:
CGNQLQVHLSPDADAYSPGQTVSLNMATGMDSWVALAAVDSAVYGVQRGAKKPLERVFQFLEKSDLG
CGAGGGLNNANVFHLAGLTFLTNANADDSQENDEPCKEIL (SEQ ID NO:89)

Figure 30

ANTI-C5 ANTIBODIES AND USES THEREOF

CROSS-REFERENCE TO RELATED APPLICATION

This application is a U.S. national phase application filed under 35 U.S.C. § 371 claiming benefit to International Patent Application No. PCT/US2018/021001, filed Mar. 6, 2018, which is entitled to priority under 35 U.S.C. § 119(e) to U.S. Provisional Patent Application No. 62/467,498, filed Mar. 6, 2017, each of which applications is hereby incorporated herein by reference in its entirety.

STATEMENT REGARDING FEDERALLY SPONSORED RESEARCH OR DEVELOPMENT

This invention was made with government support under NIH AI44970 awarded by the National Institutes of Health (NIH). The government has certain rights in the invention.

BACKGROUND OF THE INVENTION

The complement system is part of innate immunity that plays a key role in host defense. However, activated complement also has the potential to cause significant tissue injury and destruction and dysregulated complement activity has been found to be associated with a number of rare and common diseases such as paroxysmal nocturnal hemoglobinuria (PNH), atypical hemolytic uremic syndrome, rheumatoid arthritis, age-related macular degeneration etc. Thus, anti-complement therapy is a promising way of treating these human disorders.

Complement C5 is a critical protein in the terminal pathway of complement activation and is the precursor protein for generating the potent pro-inflammatory mediator C5a, as well as the cytolytic membrane attack complex (MAC).

A number of human inflammatory and autoimmune diseases are mediated by C5a and/or MAC, and blocking C5 activation should prevent C5a and MAC generation and be of therapeutic value. A humanized mouse anti-human C5 mAb, eculizumab, has been used to treat two complement-mediated diseases paroxysmal nocturnal hemoglobinuria (PNH) and atypical hemolytic uremic syndrome (aHUS). However, not all PNH patients are responsive to eculizumab treatments and one of the reasons for non-responsiveness is genetic polymorphism of human C5 with loss of epitope binding to eculizumab.

Thus, there is a need in the art for anti-human C5 mAbs that can inhibit terminal complement activity via different mechanisms and contact sites on C5 and thereby more effectively treat complement-dependent pathologies. The present invention addresses and meets these and other needs.

SUMMARY

In one embodiment, the invention comprises an antibody that specifically binds to C5. In one embodiment, the C5 is human C5. In one embodiment, the antibody is a monoclonal antibody. In one embodiment, the antibody is a humanized antibody. In one embodiment, the antibody is a chimeric antibody. In some embodiments, the antibody is a full-length antibody. In some embodiments, the antibody is an antibody fragment, which includes, but is not limited to, Fab, Fab', F(ab)2, F(ab')2, and scFv. In some embodiments, the antibody is part of a construct, for example a fusion construct comprising the antibody and a targeting moiety or an effector moiety. In some embodiments, the antibody is part of a conjugate construct, such as an antibody drug conjugate construct.

In one embodiment, the antibody comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody comprises the CDRs: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In one embodiment, the antibody comprises a heavy chain comprising the amino acid sequence of SEQ ID NO:2, or a variant thereof. In one embodiment, the antibody comprises a light chain comprising the amino acid sequence of SEQ ID NO:7, or a variant thereof. In one embodiment, the antibody comprises a heavy chain comprising the amino acid sequence of SEQ ID NO:2 and a light chain comprising the amino acid sequence of SEQ ID NO:7, or a variant or variants thereof.

In one embodiment, the antibody comprises at least one of the CDRs selected from the group consisting of: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20, or a variant or variants thereof. In one embodiment, the antibody comprises the CDRs: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20, or a variant or variants thereof.

In one embodiment, the antibody comprises a heavy chain comprising the amino acid sequence of SEQ ID NO:12, or a variant thereof. In one embodiment, the antibody comprises a light chain comprising the amino acid sequence of SEQ ID NO:17, or a variant thereof. In one embodiment, the antibody comprises a heavy chain comprising the amino acid sequence of SEQ ID NO:12 and a light chain comprising the amino acid sequence of SEQ ID NO:17, or a variant or variants thereof.

In one embodiment, the antibody comprises at least one of the CDRs selected from the group consisting of: VH-CDR1: SEQ ID NO:23; VH-CDR2: SEQ ID NO:24; VH-CDR3: SEQ ID NO:25; VL-CDR1: SEQ ID NO:28; and VL-CDR2: SEQ ID NO:29, or a variant or variants thereof. In one embodiment, the antibody comprises the CDRs: VH-CDR1: SEQ ID NO:23; VH-CDR2: SEQ ID NO:24; VH-CDR3: SEQ ID NO:25; VL-CDR1: SEQ ID NO:28; and VL-CDR2: SEQ ID NO:29, or a variant or variants thereof.

In one embodiment, the antibody comprises a heavy chain comprising the amino acid sequence of SEQ ID NO:22, or a variant thereof. In one embodiment, the antibody comprises a light chain comprising the amino acid sequence of SEQ ID NO:27, or a variant thereof. In one embodiment, the antibody comprises a heavy chain comprising the amino acid sequence of SEQ ID NO:22 and a light chain comprising the amino acid sequence of SEQ ID NO:27, or a variant or variants thereof.

In one embodiment, the antibody comprises at least one of the CDRs selected from the group consisting of: VH-CDR1: SEQ ID NO:32; VH-CDR2: SEQ ID NO:33; VH-CDR3: SEQ ID NO:34; VL-CDR1: SEQ ID NO:37; VL-CDR2: SEQ ID NO:38, VL-CDR3: SEQ ID NO:39, or a variant or variants thereof. In one embodiment, the antibody comprises the CDRs: VH-CDR1: SEQ ID NO:32; VH-CDR2: SEQ ID NO:33; VH-CDR3: SEQ ID NO:34; VL-CDR1: SEQ ID NO:37; VL-CDR2: SEQ ID NO:38, VL-CDR3: SEQ ID NO:39, or a variant or variants thereof.

In one embodiment, the antibody comprises a heavy chain comprising the amino acid sequence of SEQ ID NO:31, or a variant thereof. In one embodiment, the antibody comprises a light chain comprising the amino acid sequence of SEQ ID NO:36, or a variant thereof. In one embodiment, the antibody comprises a heavy chain comprising the amino acid sequence of SEQ ID NO:31 and a light chain comprising the amino acid sequence of SEQ ID NO:36, or a variant or variants thereof.

In one embodiment, the antibody comprises at least one of the CDRs selected from the group consisting of: VH-CDR1: SEQ ID NO:42; VH-CDR2: SEQ ID NO:43; VH-CDR3: SEQ ID NO:44; VL-CDR1: SEQ ID NO:47; VL-CDR2: SEQ ID NO:48, VL-CDR3: SEQ ID NO:49, or a variant or variants thereof. In one embodiment, the antibody comprises the CDRs: VH-CDR1: SEQ ID NO:42; VH-CDR2: SEQ ID NO:43; VH-CDR3: SEQ ID NO:44; VL-CDR1: SEQ ID NO:47; VL-CDR2: SEQ ID NO:48, VL-CDR3: SEQ ID NO:49, or a variant or variants thereof.

In one embodiment, the antibody comprises a heavy chain comprising the amino acid sequence of SEQ ID NO: 41, or a variant thereof. In one embodiment, the antibody comprises a light chain comprising the amino acid sequence of SEQ ID NO:46, or a variant thereof. In one embodiment, the antibody comprises a heavy chain comprising the amino acid sequence of SEQ ID NO:41 and a light chain comprising the amino acid sequence of SEQ ID NO:46, or a variant or variants thereof.

In one embodiment, the antibody comprises at least one of the CDRs selected from the group consisting of: VH-CDR1: SEQ ID NO:52; VH-CDR2: SEQ ID NO:53; VH-CDR3: SEQ ID NO:54; VL-CDR1: SEQ ID NO:57; VL-CDR2: SEQ ID NO:58, VL-CDR3: SEQ ID NO:59, or a variant or variants thereof. In one embodiment, the antibody comprises the CDRs: VH-CDR1: SEQ ID NO:52; VH-CDR2: SEQ ID NO:53; VH-CDR3: SEQ ID NO:54; VL-CDR1: SEQ ID NO:57; VL-CDR2: SEQ ID NO:58, VL-CDR3: SEQ ID NO:59, or a variant or variants thereof.

In one embodiment, the antibody comprises a heavy chain comprising the amino acid sequence of SEQ ID NO:51, or a variant thereof. In one embodiment, the antibody comprises a light chain comprising the amino acid sequence of SEQ ID NO:56, or a variant thereof. In one embodiment, the antibody comprises a heavy chain comprising the amino acid sequence of SEQ ID NO:51 and a light chain comprising the amino acid sequence of SEQ ID NO:56, or a variant or variants thereof.

In one embodiment, the antibody is at least one selected from the group consisting of 2G1, 8E1, 4E7, 9G6, 11C5 and 11D6.

In one embodiment, the present invention relates to a method of treating a complement pathway-mediated disease or disorder in an individual, comprising the step of administering to said individual the anti-C5 antibody of claim In one embodiment, the disease or disorder is at least selected from the group consisting of: macular degeneration (MD), age-related macular degeneration (AMD), ischemia reperfusion injury, arthritis, rheumatoid arthritis, asthma, allergic asthma, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the AP-mediated disease is C3 glomerulopathy. In some embodiments, the AP-mediated disease is macular degeneration, such as age-related macular degeneration. In one embodiment, administration of the anti-C5 antibody inhibits the generation of a C5a or C5b protein.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 3, SEQ ID NO: 4, SEQ ID NO: 5, SEQ ID NO: 8, SEQ ID NO: 9, and SEQ ID NO: 10, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 13, SEQ ID NO: 14, and SEQ ID NO: 15, SEQ ID NO: 18, SEQ ID NO: 19, and SEQ ID NO: 20, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 23, SEQ ID NO: 24, SEQ ID NO: 25, SEQ ID NO: 28, SEQ ID NO: 29, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 32, SEQ ID NO: 33, SEQ ID NO: 34, SEQ ID NO: 37, SEQ ID NO: 38, and SEQ ID NO: 39, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 42, SEQ ID NO: 43, SEQ ID NO: 44, SEQ ID NO: 47, SEQ ID NO: 48, and SEQ ID NO: 49, or a variant or variants thereof. In one embodiment, the antibody is an antibody fragment selected from the group consisting of a Fab, Fab', F(ab)2, F(ab')2, scFv, and combinations thereof.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 52, SEQ ID NO: 53, SEQ ID NO: 54, SEQ ID NO: 57, SEQ ID NO: 58, and SEQ ID NO: 59, or a variant or variants thereof. In one embodiment, the antibody is an antibody fragment selected from the group consisting of a Fab, Fab', F(ab)2, F(ab')2, scFv, and combinations thereof.

In some embodiments, the present invention is an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO: 2, or a variant thereof. In one embodiment, the antibody is an antibody fragment selected from the group consisting of a Fab, Fab', F(ab)2, F(ab')2, scFv, and combinations thereof.

In some embodiments, the present invention is an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO: 7, or a variant thereof. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO: 2, and wherein the vL region has an amino acid sequence that is more than about 90% (such as more than any of 91%, 92%, 93%, 94%, 95%, 96%, 97%, 98%, or 99%) identical to SEQ ID NO: 7. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO: 12. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO: 17. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO: 12, and wherein the vL region has an amino acid sequence that is more than about 90% (such as more than any of 91%, 92%, 93%, 94%, 95%, 96%, 97%, 98%, or 99%) identical to SEQ ID NO: 17. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO: 22. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO: 27. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO: 22, and wherein the vL region has an amino acid sequence that is more than about 90% (such as more than any of 91%, 92%, 93%, 94%, 95%, 96%, 97%, 98%, or 99%) identical to SEQ ID NO: 27. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO: 31. In one embodiment, the antibody is an antibody fragment selected from the group consisting of a Fab, Fab', F(ab)2, F(ab')2, scFv, and combinations thereof.

In one embodiment, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO: 36. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO: 31, and wherein the vL region has an amino acid sequence that is more than about 90% (such as more than any of 91%, 92%, 93%, 94%, 95%, 96%, 97%, 98%, or 99%) identical to SEQ ID NO: 36. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO: 41. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO: 46. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO: 41, and wherein the vL region has an amino acid sequence that is more than about 90% (such as more than any of 91%, 92%, 93%, 94%, 95%, 96%, 97%, 98%, or 99%) identical to SEQ ID NO: 46. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region that has an amino acid sequence that is more than about 90% (such as more than any of 91%, 92%, 93%, 94%, 95%, 96%, 97%, 98%, or 99%) identical to SEQ ID NO: 51. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a light chain variable (vL) region that has an amino acid sequence that is more than about 90% (such as more than any of 91%, 92%, 93%, 94%, 95%, 96%, 97%, 98%, or 99%) identical to SEQ ID NO: 56. In one embodiment, the antibody is an antibody fragment selected from the group consisting of a Fab, Fab', F(ab)2, F(ab')2, scFv, and combinations thereof.

In some embodiments, the present invention relates to an antibody against human C5, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, or 99%) identical to SEQ ID NO: 51, and wherein the vL region has an amino acid sequence that is more than about 90% (such as more than any of 91%, 92%, 93%, 94%, 95%, 96%, 97%, 98%, or 99%) identical to SEQ ID NO: 56. In one embodiment, the antibody is an antibody fragment selected from the group consisting of a Fab, Fab', F(ab)2, F(ab')2, scFv, and combinations thereof.

In one embodiment, the present invention relates to a cell comprising at least one of the antibodies described elsewhere herein. In some embodiments, the cell produces the antibody of at least one of the antibodies described elsewhere herein. In one embodiment, the cell is a hybridoma.

In one embodiment, the present invention is a cell line comprising at least one of the antibodies described elsewhere herein. In some embodiments, the cell line produces at least one of the antibodies described elsewhere herein. In some embodiments, the cell line is a hybridoma cell line.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings. In the drawings:

FIG. 9A and FIG. 9B, depicts the effects of anti-human C5 mAbs 4E7, 9G6, 11C5, 2G1, 11D9 and 8E1 on complement-mediated hemolysis. FIG. 9A illustrates red blood cells (RBC) lysis determined by measuring the absorbance at $OD_{405}$ after antibody-sensitized sheep RBCs were incubated with 50% NHS containing serial dilutions of each anti-C5 mAb at 37° C. for 1 hour. RBC lysis was determined by measuring the absorbance at $OD_{405}$ nm. At 120 µg/ml, all mAbs inhibited 50% NHS-mediated sheep erythrocyte lysis. At lower doses (e.g., 30-60 µg/ml), 9G6 was less potent in preventing hemolysis than other mAbs. FIG. 9B illustrates that at 30 µg/ml, mAb 2G1 and 8E1 were more potent at inhibiting complement-mediated hemolysis than 4E7, 9G6, 11C5 and 11D9.

FIG. 13 depicts the variable region sequences of heavy and light chains of mAb 2G1.

FIG. 14 depicts the variable region sequences of heavy and light chains of mAb 8E1.

FIG. 15 depicts the variable region sequences of heavy and light chains of mAb 4E7.

FIG. 16 depicts the variable region sequences of heavy and light chains of mAb 9G6.

FIG. 17 depicts the variable region sequences of heavy and light chains of mAb 11C5.

FIG. 18 depicts the variable region sequences of heavy and light chains of mAb 11D9.

FIG. 19 depicts amino acid sequences of human IgG4 heavy chain constant region, with a serine 228 to proline mutation (i.e., S228P) and human kappa light chain constant region. These sequences were used to construct chimeric (mouse variable region+human constant regions) and humanized (humanized mouse variable region+human constant regions) anti-human C5 antibody (2G1).

FIG. 22 depicts nucleotide and amino acid sequences of a humanized variable heavy chain (VH) of mAb 2G1 (humanized 2G1 VH-11801). Humanization was achieved by CDR grating from murine mAb 2G1 VH into a germline encoded human VH frame (11801). The amino acid sequence of signal peptide is underlined and that of CDR1, CDR2 and CDR3 is bolded and shaded.

FIG. 23 depicts nucleotide and amino acid sequences of another humanized VH of mAb 2G1 (humanized 2G1 VH-16901). Humanization was achieved by CDR grating from murine mAb 2G1 VH into a germline encoded human VH frame (16901). The amino acid sequence of signal peptide is underlined and that of CDR1, CDR2 and CDR3 is bolded shaded.

FIG. 24 depicts nucleotide and amino acid sequences of a humanized variable light chain (VL) of mAb 2G1 (humanized 2G1 VL-1901). Humanization was achieved by CDR grating from murine mAb 2G1 VL into a germline encoded human VL frame (1901). The amino acid sequence of signal peptide is underlined and that of CDR1, CDR2 and CDR3 is bolded and shaded.

FIGS. 29A and 29B, depicts results from experiments using Western blotting to detect human C5 using mAb 2G1-3 (FIG. 29A) and a control mAb QDC5 (FIG. 29B) showing that mAb 2G1-3 binds to the β chain of human C5. Human C5 (1 μg was used per lane, from Comptech, cat #A120) was run on SDS-PAGE under non-reducing (NR) or reducing (R) conditions SDS-PAGE. The control mAb QDC5 is a recombinant human IgG4 mAb bearing VH and VL sequences of a humanized mouse anti-human C5 mAb as described in Thomas et al. (Mol Immunol. 1996 December; 33(17-18):1389-401). This mAb is known to binds to an epitope in the α chain of human C5. As expected, both mAb 2G1-3 and QDC5 bound to non-reduced human C5 similarly. Under reducing condition, QDC5 bound to the α chain of human C5 as expected, whereas mAb 2G1-3 bound to a different band corresponding to the β chain of human C5. After SDS-PAGE, proteins were transferred on to PVDF membrane and blocked with 5% non-fat dry milk in TBS for 1 h at room temperature. The membranes were incubated with 10 μg/ml of 2G1-3 or QDC5 for 1 h at room temperature. After washing with TBS with 0.1% Tween-20 (TBST) for 6×5 min, 1:4000 dilution of Rabbit α-mouse IgG-HRP or α-human IgG-HRP were added to the membranes and incubated for 1 h at room temperature. After final washing, proteins were detected using Pierce™ ECL 2 Western Blotting substrate according to manufacturer's instructions.

FIG. 30, comprising FIGS. 30A and 30B, depicts the domain structure and sequences of human C5. Human C5 is composed of a and β chains separated by a small C5a segment that is released upon C5 activation (FIG. 30A). The human C5 β chain is in turn composed of 6 MG domains with amino acid sequences as listed (FIG. 30B).

FIGS. 31A and 31B, depicts the Western blot detection of human C5 β chain and human C5 β chain deletion mutants lacking individual MG domains. (FIG. 31A). Western blotting using a goat anti-human C5 polyclonal antibody detected the intact β chain and the 6 MG domain deletion mutants transiently expressed in HEK cells. Supernatants of transfected HEK cells were used for analysis. The numbers 1, 2, 3, 4, 5, 6 designates MG1, MG2, MG3, MG4, MG5 and MG6 deletion mutants. Supernatant from non-transfected HEK cells (Blank) was used as a negative control. These results demonstrated that all deletion mutants were expressed. (FIG. 31B) Calculated molecular weights in kDa of human C5 β chain and the 6 MG deletion mutants are consistent with the detected bands on Western blot.

FIG. 32 depicts the results of a Sandwich ELISA assay using polyclonal anti-C5 antibody for detection demonstrating that MG4 domain within human C5 β chain is critical for mAb 2G1-3 binding. 2G1-3 was coated onto 96-well plate and supernatants from non-transfected or transfected HEK cells were added. After incubation and washing, the bound β chain or deletion mutant e proteins in transfection supernatants were detected by a goat anti-human C5 polyclonal antibody. Signals were detected in normal human serum (NHS) and supernatants of intact human β chain and MG1 deletion mutant but not MG4 deletion mutant, suggesting that MG4 but not MG1 within the β chain is critical for 2G1-3 binding.

DETAILED DESCRIPTION OF THE INVENTION

Figure 1:
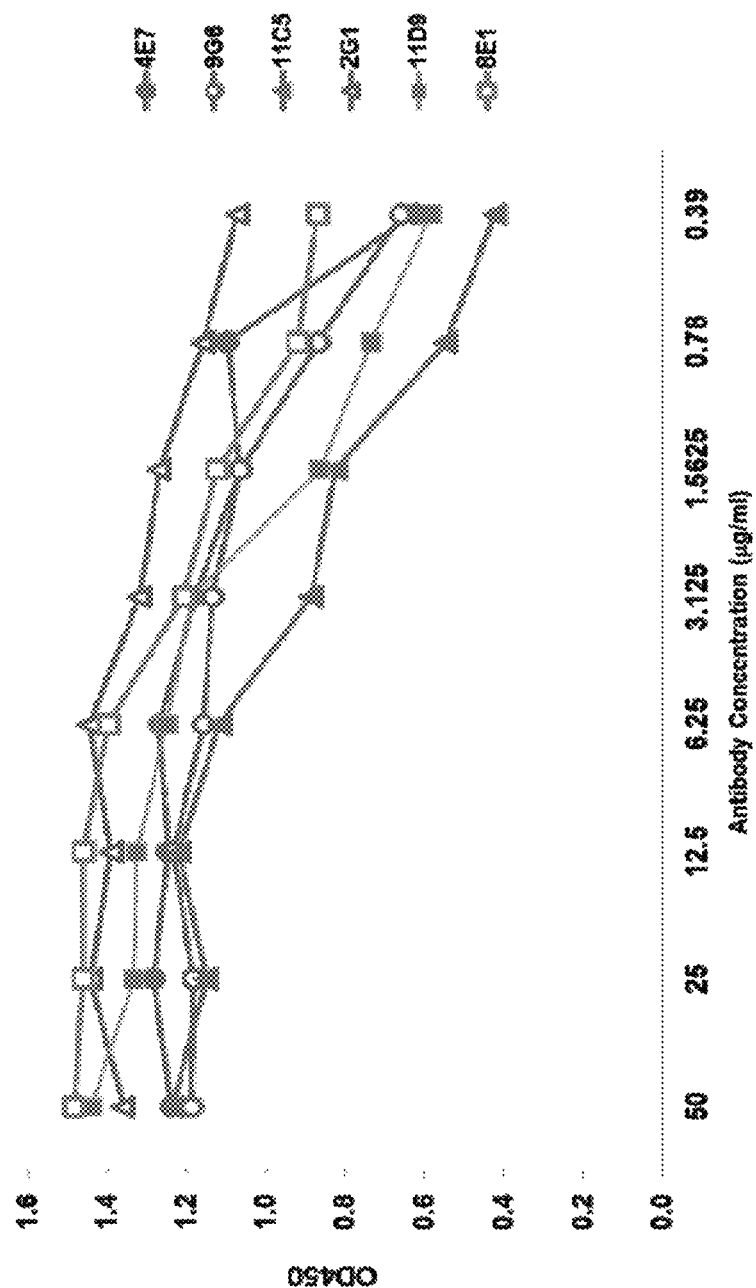
FIG. 1 depicts results from an ELISA assay demonstrating the binding of anti-human C5 mAbs 4E7, 9G6, 11C5, 2G1, 11D9 and 8E1 to human C5. Direct antigen binding ELISA in which mAbs are serially diluted across microtiter plates coated with purified human C5. All six mAbs showed high reactivity with human C5.
Figure 2:
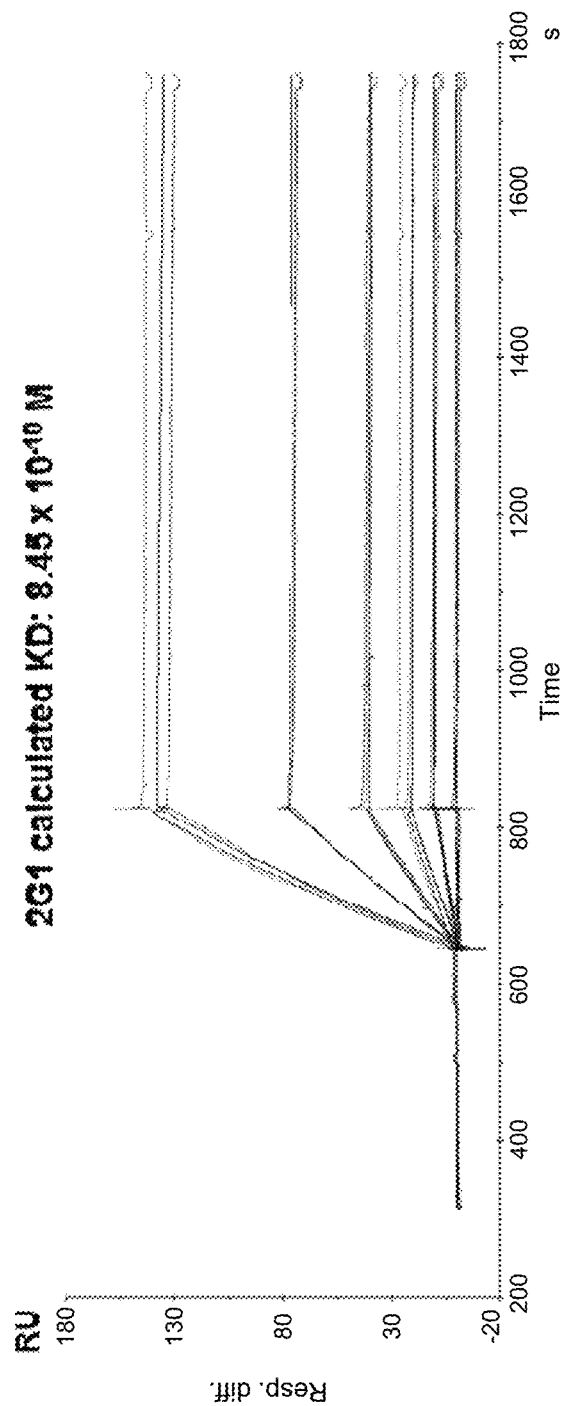
FIGS. 2-7 depict the results of experiments measuring binding affinities of anti-C5 mAb 2G1, 8E1, 4E7, 9G6, 11C5 and 11D9 to C5. Purified αmRabbit IgG (RAMFc) mAb was coupled onto a CM4 chip using the amine coupling method. Then, anti-C5 mAbs were captured on immobilized RAMFc. Biacore analyses were performed on a Biacore-2000 instrument.
Figure 3:
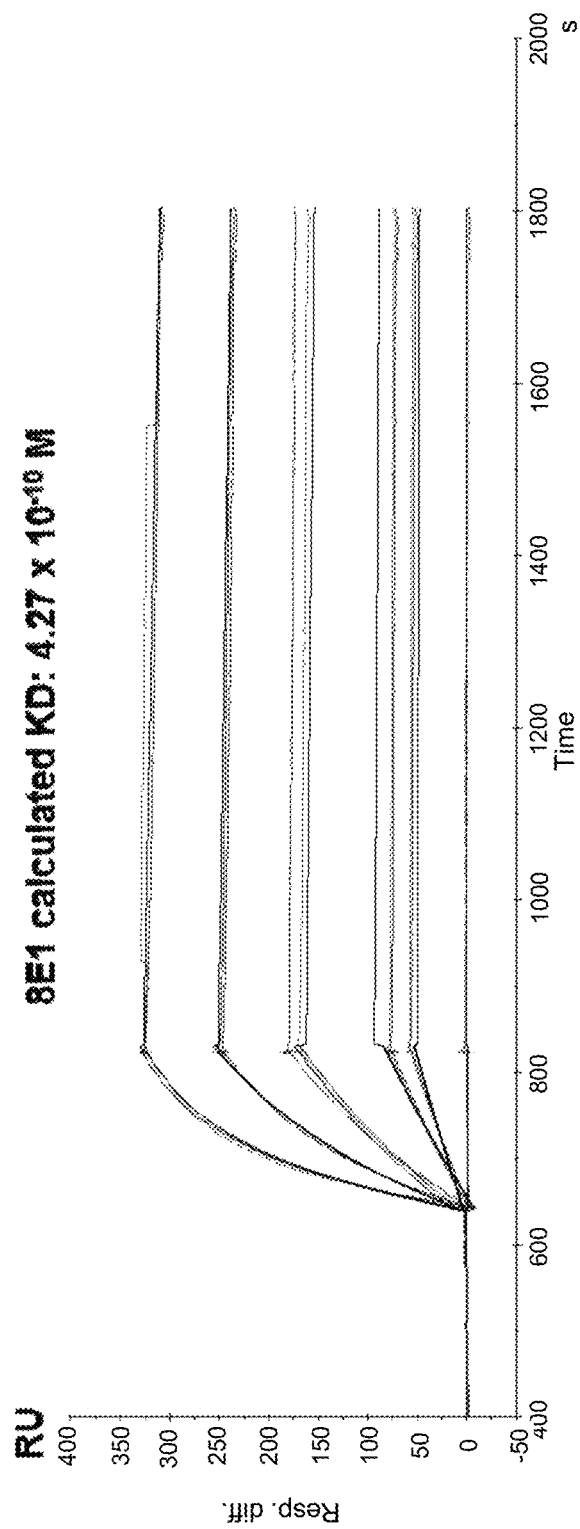
Figure 4:
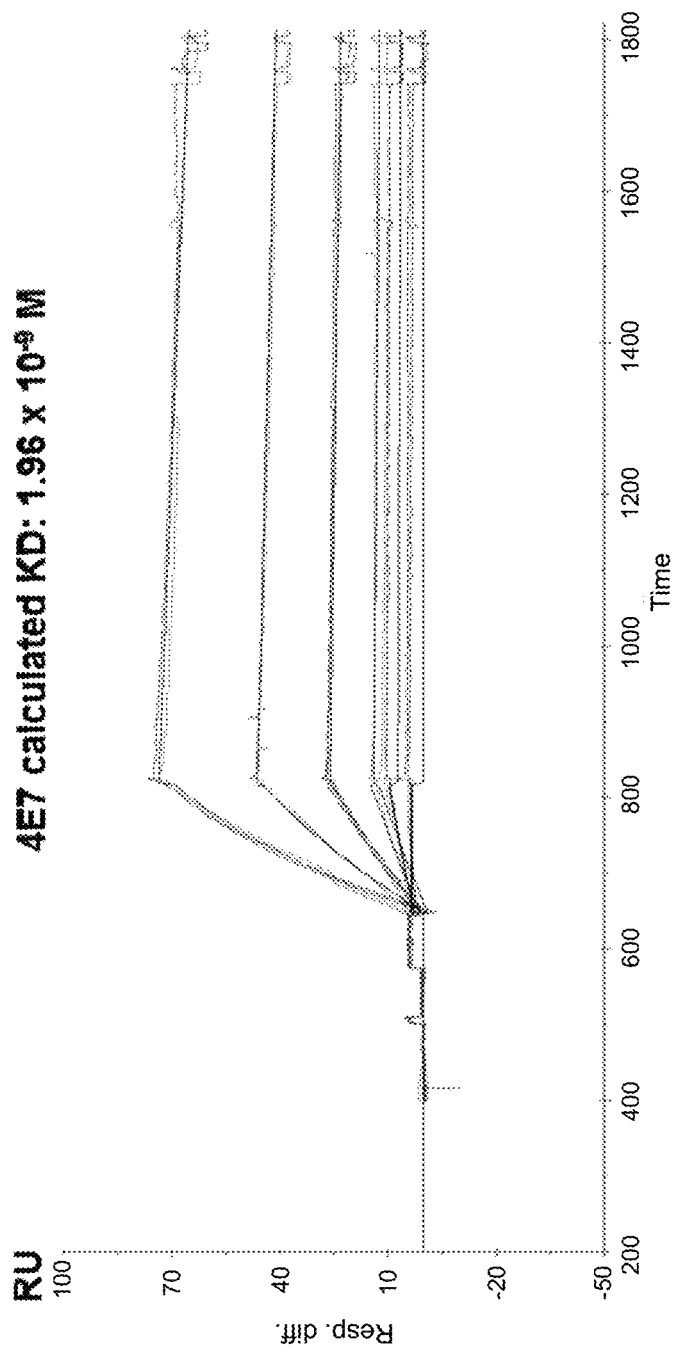
Figure 5:
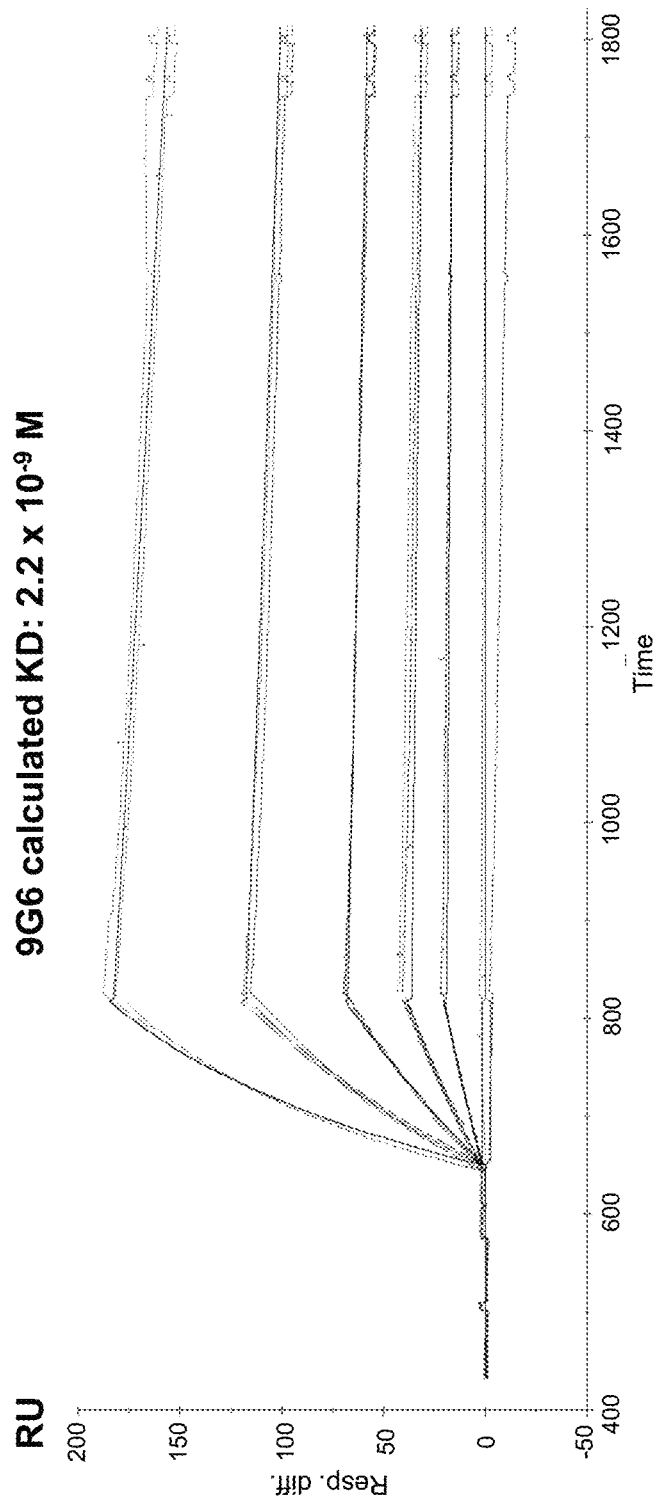
Figure 6:
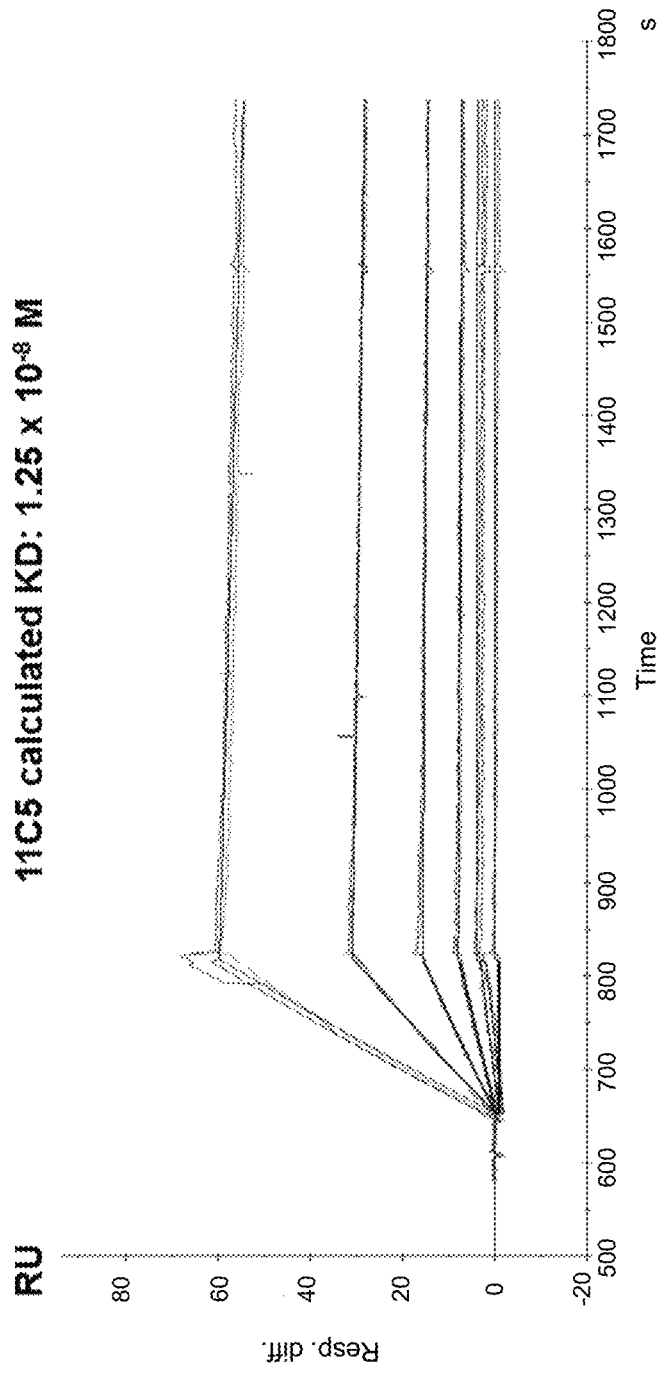
Figure 7:
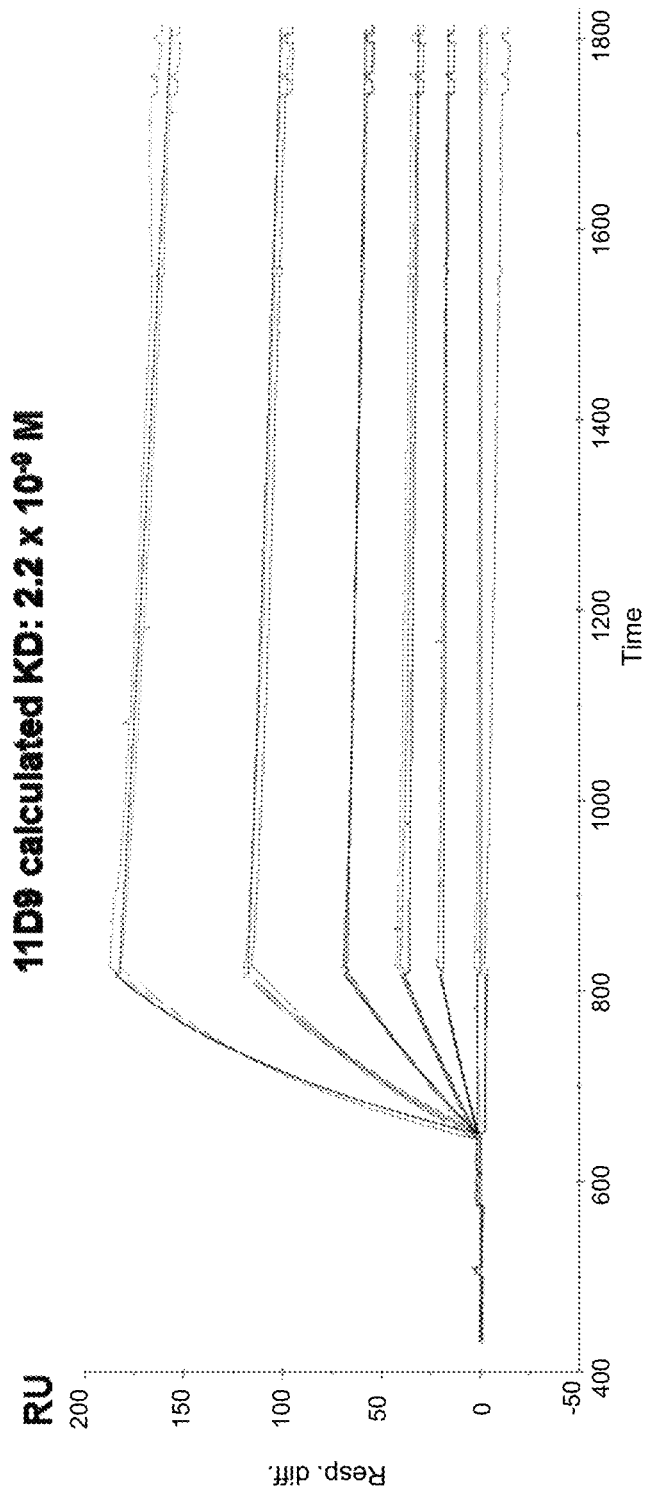

This invention relates to the inhibition of complement signaling using an anti-C5 antibody. In various embodiments, the invention is directed to compositions and methods for treating a complement-mediated disease or complement-mediated disorder in an individual by contacting the individual with an anti-C5 antibody. The complement-mediated pathologies and conditions that can be treated with the compositions and methods of the invention include, but are not limited to, macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "inhibit" and "inhibition," as used herein, means to reduce, suppress, diminish or block an activity or function by at least about 10% relative to a control value. In some embodiments, the activity is suppressed or blocked by at least about 50% compared to a control value. In some embodiments, the activity is suppressed or blocked by at least about 75%. In some embodiments, the activity is suppressed or blocked by at least about 95%.

The terms "effective amount" and "pharmaceutically effective amount" refer to a sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The terms "patient," "subject," "individual," and the like are used interchangeably herein, and refer to any animal, in some embodiments a mammal, and in some embodiments a human, having a complement system, including a human in need of therapy for, or susceptible to, a condition or its sequelae. The individual may include, for example, dogs, cats, pigs, cows, sheep, goats, horses, rats, monkeys, and mice and humans.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Operably linked" or "operatively linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "therapeutic treatment" is a treatment administered to a subject who exhibits signs of disease or disorder, for the purpose of diminishing or eliminating those signs.

As used herein, "treating a disease or disorder" means reducing the frequency and/or severity of a sign and/or symptom of the disease or disorder is experienced by a patient.

The phrase "biological sample", "sample" or "specimen" as used herein, is intended to include any sample comprising a cell, a tissue, or a bodily fluid in which expression of a nucleic acid or polypeptide can be detected. The biological sample may contain any biological material suitable for detecting the desired biomarkers, and may comprise cellular and/or non-cellular material obtained from the individual. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "antibody," as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from a subject with heavy chain disease, or prepared by the cloning and expression of VH (variable heavy chain immunoglobulin) genes from a subject.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes and binds to a specific target molecule, but does not substantially recognize or bind other molecules in a sample. In some instances, the terms "specific binding" or "specifically binding," is used to mean that the recognition and binding is dependent upon the presence of a particular structure (e.g., an antigenic determinant or epitope) on the target molecule. If, for example, an antibody specifically binds to epitope "A," the presence of an unlabelled molecule containing epitope A (or free, unlabeled A) in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and or at least about 75%, or at least about 90%, or at least about 95% of the nucleotide residues of the first portion are capable of base pairing with nucleotide residues in the second portion. In some embodiments, all nucleotide residues of the first portion are capable of base pairing with nucleotide residues in the second portion.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Isolated" means altered or removed from the natural state. For example, a nucleic acid or a peptide naturally present in its normal context in a living subject is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "progeny" as used herein refers to a descendent or offspring and includes the offspring of a mammal, and also included the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. In various embodiments, the variant sequence is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to the reference sequence.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "scanning window," as used herein, refers to a segment of a number of contiguous positions in which a sequence may be evaluated independently of any flanking sequence. A scanning window generally is shifted incrementally along the length of a sequence to be evaluated with each new segment being independently evaluated. An incremental shift may be of 1 or more than one position.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This invention relates to the inhibition of the complement signaling and complement-related disorders using an anti-human C5 antibody. In one embodiment, the invention is directed to inhibiting the complement signaling cascade by specifically targeting complement component C5 protein, or a fragment of the protein C5a or C5b. In one embodiment, the invention is directed to methods of treating and preventing inflammation and autoimmune diseases mediated by unwanted, uncontrolled, excessive complement activation. In one embodiment the invention is directed towards the treatment of complement-mediated disease or complement-mediated disorder in an individual by contacting the individual with an anti-C5 antibody.

In one embodiment, the invention is a method of treating a complement-mediated disease or disorder in an individual, comprising the step of administering to said individual an anti-C5 antibody, thereby inhibiting the generation of a C5a or C5b protein, and formation of MAC. Examples of complement-mediated pathologies that can be treated using the methods of the invention include, but are not limited to macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the compositions and methods of the invention are useful for treating subject, including subjects having PNH, who are not responsive to treatment with eculizumab. By way of non-limiting example, some subjects may have a mutation in the alpha chain of C5 that may render them resistant to treatment of eculizumab (see Genetic variants in C5 and poor response to eculizumab. Nishimura J, et al., N Engl J Med. 2014 Feb. 13; 370(7):632-9).

The ability of the immune system to discriminate between "self" and "non-self" antigens is vital to the functioning of the immune system as a specific defense against invading microorganisms. "Non-self" antigens are those antigens on substances entering or present in the body which are detectably different or foreign from the subject's own constituents, whereas "self" antigens are those which, in the healthy subject, are not detectably different or foreign from its own constituents. In various embodiments of the methods, the complement activation that is inhibited is that which was triggered by at least one of the group consisting of a microbial antigen, a non-biological foreign surface, altered self-tissue, or combinations thereof. One example of a non-biological foreign surface is blood tubing such as that used in cardio-pulmonary bypass surgery or kidney dialysis. Examples of altered self-tissues include apoptotic, necrotic and ischemia-stressed tissues and cells, or combinations thereof.

In some embodiments, the anti-C5 antibodies of the invention inhibit the downstream effects of activation of the alternative complement pathway (AP), the classical pathway (CP), or the lectin pathway (LP). Generally, the CP is initiated by antigen-antibody complexes, the LP is activated by binding of lectins to sugar molecules on microbial surfaces, while the AP is constitutively active at a low level but can be quickly amplified on bacterial, viral, and parasitic cell surfaces due to the lack of regulatory proteins. Host cells are usually protected from AP complement activation by regulatory proteins. But in some situations, such as when the regulatory proteins are defective or missing, the AP can also be activated uncontrollably on host cells, leading to complement-mediated disease or disorder. The CP consists of components C1, C2, C4 and converges with the AP at the C3 activation step. The LP consists of mannose-binding lectins (MBLs) and MBL-associated serine proteases (Masps) and shares with the CP the components C4 and C2. The AP consists of components C3 and several factors, such as factor B, factor D, properdin, C5 and the fluid phase regulator factor H. Complement activation consists of three stages: (a) recognition, (b) enzymatic activation, and (c) membrane attack leading to cell death. The first phase of CP complement activation begins with C1. C1 is made up of three distinct proteins: a recognition subunit, C1q, and the serine protease subcomponents, C1r and C1s, which are bound together in a calcium-dependent tetrameric complex, C1r2 s2. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, C4b2a, which in turn cleaves C3 to form C3a and C3b. Activation of the LP is initiated by MBL binding to certain sugars on the target surface and this triggers the activation of MBL-associated serine proteases (MASPs) which then cleave C4 and C2 in a manner analogous to the activity of C1s of the CP, resulting in the generation of the C3 convertase, C4b2a. Thus, the CP and LP are activated by different mechanisms but they share the same components C4 and C2 and both pathways lead to the generation of the same C3 convertase, C4b2a. The cleavage of C3 by C4b2a into C3b and C3a is a central event of the complement pathway for two reasons. It initiates the AP amplification loop because surface deposited C3b is a central intermediate of the AP. Both C3a and C3b are biologically important. C3a is proinflammatory and together with C5a are referred to as anaphylatoxins. C3b and its further cleavage products also bind to complement receptors present on neutrophils, eosinophils, monocytes and macrophages, thereby facilitating phagocytosis and clearance of C3b-opsonized particles. Finally, C3b can associate with C4b2a to form the C5 convertase of the CP and LP to activate the terminal complement sequence, leading to the production of C5a, a potent proinflammatory mediator, and the assembly of the lytic membrane attack complex (MAC), C5-C9.

In one embodiment, the activity of the complement pathway that is inhibited using a method of the invention is complement pathway activation induced by at least one of the group selected from a lipopolysacchride (LPS), lipooligosaccharide (LOS), pathogen-associated molecular patterns (PAMPs) and danger-associated molecular patterns (DAMPs). In another embodiment, the activity of complement signaling that is inhibited using a method of invention is the generation of C5a protein. In another embodiment, the activity of complement signaling that is inhibited using a method of invention is the generation of C5b protein. In another embodiment, the activity of complement signaling that is inhibited using a method of the invention is the formation of MAC. In another embodiment, the activity of the complement pathway that is inhibited using a method of the invention is C5 dependent.

In one embodiment, the invention is a method of inhibiting initiation of terminal complement activation in an individual, comprising the step of administering to said individual an anti-C5 antibody, thereby inhibiting initiation of terminal complement activation originating from CP, LP or AP activation in an individual. Examples of these embodiments are PNH patients who suffer from complement-mediated hemolysis and individuals suffering from complement-mediated aHUS, asthma, ischemic/reperfusion injury, rheumatoid arthritis and ANCA-mediated kidney diseases. In various embodiments of the invention, diseases and disorders that can be treated using the compositions and methods of the invention include, but are not limited to, complement-mediated hemolysis, complement-mediated aHUS, C3 glomerulopathy, neuromyelitis optica, myasthenia gravis, asthma, ischemic/reperfusion injury, rheumatoid arthritis and ANCA-mediated kidney diseases or disorders.

In various other embodiments, provided herein are methods of identifying a potential anti-C5 antibody having inhibitory effects on complement signaling. One such method includes the steps of: a) coating a plate with lipopolysaccharide (LPS); b) washing the plate to remove unbound LPS; c) adding bovine serum albumin (BSA) in phosphate buffered saline (PBS); d) washing the plate to remove unbound BSA; e) adding a mixture of a candidate anti-C5 antibody compound that has been pre-incubated with serum and is mixed into normal human serum; f) washing the plate; g) adding an HRP-conjugated anti-human C3 antibody; h) washing the plate to remove unbound antibody; i) adding HRP Substrate Reagent; j) adding sulphuric acid to stop the reaction; k) measuring the optical density at 450 nm; l) comparing the optical density of the plate containing the candidate anti-C5 antibody compound to the optical density of a positive comparator control and a negative comparator control; wherein when the optical density is diminished as compared with the positive comparator control, the anti-C5 antibody is identified.

Anti-C5 Antibodies

In some embodiments, the invention includes compositions comprising an antibody that specifically binds to C5. In one embodiment, the anti-C5 antibody is a polyclonal antibody. In another embodiment, the anti-C5 antibody is a monoclonal antibody. In some embodiments, the anti-C5 antibody is a chimeric antibody. In further embodiments, the anti-C5 antibody is a humanized antibody. In some embodiments, the antibody is an antibody fragment. In some embodiments, the C5 is human C5.

In some embodiments, binding of the antibody or the fragment of the antibody to human-C5 is associated with a reduction in the generation of C5a or C5b and the formation of MAC in the complement activation pathway in an intact organism. In some embodiments, the invention is a protein or a polypeptide capable of binding to human C5. In some embodiments, the antibody or antibody fragment; the protein or the polypeptide binds to a relevant portion or fraction or epitope of the human-C5; and the binding of the antibody, or the antibody fragment thereof, or the protein or the polypeptide to the relevant portion of the human-C5 is associated with a reduction in the generation of C5a or C5b and the formation of MAC in an intact organism.

In some embodiments, the human-C5 binding antibody or a C5 binding antibody fragment thereof, is further conjugated to a protein, a peptide or another compound. In some embodiments, the human-C5 binding antibody, or an antibody fragment thereof, is conjugated to a protein, a peptide or other compound. In some embodiments, the protein, peptide or other compound to which the human-C5 binding antibody or antibody fragment thereof is conjugated is a targeting moiety (i.e., the targeting moiety specifically binds to a molecule other than human-C5). In some embodiments, the protein, peptide, or other compound to which the human-C5 binding antibody or antibody fragment thereof is conjugated to is an effector molecule (e.g., a cytotoxic molecule).

In one embodiment, the anti-C5 antibody or an antigen-binding fragment thereof comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In some embodiments, the anti-C5 antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:3; and VL-CDR1: SEQ ID NO:8.

In some embodiments, the anti-C5 antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:4; and VL-CDR2: SEQ ID NO:9.

In some embodiments, the anti-C5 antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:5; and VL-CDR3: SEQ ID NO:10.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5 antibody or antigen-binding fragment thereof comprises: VH-CDR1 comprising the amino acid sequence of SEQ ID NO:3; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:10.

In some embodiments, the anti-C5 antibody or an antigen binding fragment thereof comprises a heavy chain comprising the amino acid sequence of SEQ ID NO:2, or a variant thereof. In other embodiments, the anti-C5 antibody comprises a light chain comprising the amino acid sequence of SEQ ID NO:7, or a variant thereof. In another embodiment, the anti-C5 antibody is mAb 2G1, or a variant thereof. The monoclonal anti-C5 antibody mAb 2G1 comprises a heavy chain comprising the amino acid sequence of SEQ ID NO:2 and a light chain comprising the amino acid sequence of SEQ ID NO:7. In some embodiments, the monoclonal anti-C5 antibody is humanized. In some embodiments the monoclonal anti-C5 antibody is a chimeric antibody.

In one embodiment, the anti-C5 antibody or an antigen binding fragment thereof comprises at least one of the CDRs selected from the group consisting of: VH-CDR1: SEQ ID NO:13; VH-CDR2: SEQ ID NO:14; VH-CDR3: SEQ ID NO:15, VL-CDR1: SEQ ID NO:18; VL-CDR2: SEQ ID NO:19; and VL-CDR3: SEQ ID NO:20, or a variant or variants thereof. In another embodiment, the anti-C5 antibody comprises all of the CDRs of the group consisting of: VH-CDR1: SEQ ID NO:13; VH-CDR2: SEQ ID NO:14; VH-CDR3: SEQ ID NO:15, VL-CDR1: SEQ ID NO:18; VL-CDR2: SEQ ID NO:19; and VL-CDR3: SEQ ID NO:20, or a variant or variants thereof.

In some embodiments, the anti-C5 antibody or antigen-binding fragment thereof comprises: VH-CDR1 comprising the amino acid sequence of SEQ ID NO:13 or a variant thereof comprising up to about 3 (such as about any of 1, 2, or 3) amino acid substitutions; and VL-CDR1: SEQ ID NO:18, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:13; and VL-CDR1: SEQ ID NO:18.

In some embodiments, the anti-C5 antibody or antigen-binding fragment thereof comprises: VH-CDR2 comprising the amino acid sequence of SEQ ID NO:14, or a variant thereof comprising up to about 3 (such as about any of 1, 2, or 3) amino acid substitutions; and VL-CDR2: SEQ ID NO:19, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:14; and VL-CDR2: SEQ ID NO:19.

In some embodiments, the anti-C5 antibody or antigen-binding fragment thereof comprises: VH-CDR3 comprising the amino acid sequence of SEQ ID NO:15, or a variant thereof comprising up to about 3 (such as about any of 1, 2, or 3) amino acid substitutions; and VL-CDR3: SEQ ID NO:20, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:15; and VL-CDR3: SEQ ID NO:20.

In some embodiments, the anti-C5 antibody or antigen-binding fragment thereof comprises: VH-CDR1 comprising the amino acid sequence of SEQ ID NO:13, or a variant thereof comprising up to about 3 (such as about any of 1, 2, or 3) amino acid substitutions; VH-CDR2 comprising the amino acid sequence of SEQ ID NO:14, or a variant thereof comprising up to about 3 (such as about any of 1, 2, or 3) amino acid substitutions; VH-CDR3 comprising the amino acid sequence of SEQ ID NO:15, or a variant thereof comprising up to about 3 (such as about any of 1, 2, or 3) amino acid substitutions; VL-CDR1 comprising the amino acid sequence of SEQ ID NO:18, or a variant thereof comprising up to about 3 (such as about any of 1, 2, or 3) amino acid substitutions; VL-CDR2 comprising the amino acid sequence of SEQ ID NO:19, or a variant thereof comprising up to about 3 (such as about any of 1, 2, or 3) amino acid substitutions; and VL-CDR3 comprising the amino acid sequence of SEQ ID NO:20, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:13, or a variant thereof comprising up to about 3 (such as about any of 1, 2, or 3) amino acid substitutions; VH-CDR2 comprising the amino acid sequence of SEQ ID NO:14, or a variant thereof comprising up to about 3 (such as about any of 1, 2, or 3) amino acid substitutions; VH-CDR3 comprising the amino acid sequence of SEQ ID NO:15; VL-CDR1 comprising the amino acid sequence of SEQ ID NO:18, or a variant thereof comprising up to about 3 (such as about any of 1, 2, or 3) amino acid substitutions; VL-CDR2 comprising the amino acid sequence of SEQ ID NO:19, or a variant thereof comprising up to about 3 (such as about any of 1, 2, or 3) amino acid substitutions; and VL-CDR3 comprising the amino acid sequence of SEQ ID NO:20.

In some embodiments, the anti-C5 antibody or antigen-binding fragment thereof comprises: VH-CDR1 comprising the amino acid sequence of SEQ ID NO:13; VH-CDR2 comprising the amino acid sequence of SEQ ID NO:14; VH-CDR3 comprising the amino acid sequence of SEQ ID NO:15; VL-CDR1 comprising the amino acid sequence of SEQ ID NO:18; VL-CDR2 comprising the amino acid sequence of SEQ ID NO:19; and VL-CDR3 comprising the amino acid sequence of SEQ ID NO:20.

In some embodiments, the anti-C5 antibody comprises a heavy chain comprising the amino acid sequence of SEQ ID NO:12, or a variant thereof. In other embodiments, the anti-C5 antibody comprises a light chain comprising the amino acid sequence of SEQ ID NO:17, or a variant thereof. In another embodiment, the anti-C5 antibody is mAb 8E1, or a variant thereof. The monoclonal anti-C5 antibody mAb 8E1 comprises a heavy chain comprising the amino acid sequence of SEQ ID NO:12 and a light chain comprising the amino acid sequence of SEQ ID NO:17. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:23; VH-CDR2: SEQ ID NO:24; VH-CDR3: SEQ ID NO:25, VL-CDR1: SEQ ID NO:28; and VL-CDR3: SEQ ID NO:29, or a variant or variants thereof. In another embodiment, the anti-C5 antibody comprises all of the CDRs of the group consisting of: VH-CDR1: SEQ ID NO:23; VH-CDR2: SEQ ID NO:24; VH-CDR3: SEQ ID NO:25; VL-CDR1: SEQ ID NO:28; and VL-CDR3: SEQ ID NO:29, or a variant or variants thereof.

In some embodiments, the anti-C5 antibody or antigen-binding fragment thereof comprises: VH-CDR1 comprising the amino acid sequence of SEQ ID NO:23 or a variant thereof comprising up to about 3 (such as about any of 1, 2, or 3) amino acid substitutions; and VL-CDR1: SEQ ID NO:28, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:23; and VL-CDR1: SEQ ID NO:28.

In some embodiments, the anti-C5 antibody or antigen-binding fragment thereof comprises: VH-CDR2 comprising the amino acid sequence of SEQ ID NO:24, or a variant thereof comprising up to about 3 (such as about any of 1, 2, or 3) amino acid substitutions; and VL-CDR2: SEQ ID NO:29, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:24; and VL-CDR2: SEQ ID NO:29.

In some embodiments, the anti-C5 antibody or antigen-binding fragment thereof comprises: VH-CDR3 comprising the amino acid sequence of SEQ ID NO:25, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:25.

In some embodiments, the anti-C5 antibody or antigen-binding fragment thereof comprises: VH-CDR1 comprising the amino acid sequence of SEQ ID NO:23, or a variant thereof comprising up to about 3 (such as about any of 1, 2, or 3) amino acid substitutions; VH-CDR2 comprising the amino acid sequence of SEQ ID NO:24, or a variant thereof comprising up to about 3 (such as about any of 1, 2, or 3) amino acid substitutions; VH-CDR3 comprising the amino acid sequence of SEQ ID NO:25, or a variant thereof comprising up to about 3 (such as about any of 1, 2, or 3) amino acid substitutions; VL-CDR1 comprising the amino acid sequence of SEQ ID NO:28, or a variant thereof comprising up to about 3 (such as about any of 1, 2, or 3) amino acid substitutions; VL-CDR2 comprising the amino acid sequence of SEQ ID NO:29, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:23, or a variant thereof comprising up to about 3 (such as about any of 1, 2, or 3) amino acid substitutions; VH-CDR2 comprising the amino acid sequence of SEQ ID NO:24, or a variant thereof comprising up to about 3 (such as about any of 1, 2, or 3) amino acid substitutions; VH-CDR3 comprising the amino acid sequence of SEQ ID NO:15; VL-CDR1 comprising the amino acid sequence of SEQ ID NO:28, or a variant thereof comprising up to about 3 (such as about any of 1, 2, or 3) amino acid substitutions; and VL-CDR2 comprising the amino acid sequence of SEQ ID NO:29, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:23; VH-CDR2 comprising the amino acid sequence of SEQ ID NO:24; VH-CDR3 comprising the amino acid sequence of SEQ ID NO:25; VL-CDR1 comprising the amino acid sequence of SEQ ID NO:28; and VL-CDR2 comprising the amino acid sequence of SEQ ID NO:29.

In some embodiments, the anti-C5 antibody or an antigen binding fragment thereof comprises a heavy chain comprising the amino acid sequence of SEQ ID NO:22, or a variant thereof. In other embodiments, the anti-C5 antibody comprises a light chain comprising the amino acid sequence of SEQ ID NO:27, or a variant thereof. In another embodiment, the anti-C5 antibody is mAb 4E7, or a variant thereof. The monoclonal anti-C5 antibody mAb 4E7 comprises a heavy chain comprising the amino acid sequence of SEQ ID NO:22 and a light chain comprising the amino acid sequence of SEQ ID NO:27. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:32; VH-CDR2: SEQ ID NO:33; VH-CDR3: SEQ ID NO:34; VL-CDR1: SEQ ID NO:37; VL-CDR2: SEQ ID NO:38; and VL-CDR3: SEQ ID NO:39, or a variant or variants thereof. In another embodiment, the anti-C5 antibody comprises all of the CDRs of the group consisting of VH-CDR1: SEQ ID NO:32; VH-CDR2: SEQ ID NO:33; VH-CDR3: SEQ ID NO:34; VL-CDR1: SEQ ID NO:37; VL-CDR2: SEQ ID NO:38; and VL-CDR3: SEQ ID NO:39, or a variant or variants thereof.

In some embodiments, the anti-C5 antibody or antigen-binding fragment thereof comprises: VH-CDR1 comprising the amino acid sequence of SEQ ID NO:32 or a variant thereof comprising up to about 3 (such as about any of 1, 2, or 3) amino acid substitutions; and VL-CDR1: SEQ ID NO:37, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:32; and VL-CDR1: SEQ ID NO:37.

In some embodiments, the anti-C5 antibody or antigen-binding fragment thereof comprises: VH-CDR2 comprising the amino acid sequence of SEQ ID NO:33, or a variant thereof comprising up to about 3 (such as about any of 1, 2, or 3) amino acid substitutions; and VL-CDR2: SEQ ID NO:38, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:33; and VL-CDR2: SEQ ID NO:38.

In some embodiments, the anti-C5 antibody or antigen-binding fragment thereof comprises: VH-CDR3 comprising the amino acid sequence of SEQ ID NO:34, or a variant thereof comprising up to about 3 (such as about any of 1, 2, or 3) amino acid substitutions; and VL-CDR3: SEQ ID NO:39, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:34; and VL-CDR3: SEQ ID NO:39.

In some embodiments, the anti-C5 antibody or antigen-binding fragment thereof comprises: VH-CDR1 comprising the amino acid sequence of SEQ ID NO:32, or a variant thereof comprising up to about 3 (such as about any of 1, 2, or 3) amino acid substitutions; VH-CDR2 comprising the amino acid sequence of SEQ ID NO:33, or a variant thereof comprising up to about 3 (such as about any of 1, 2, or 3) amino acid substitutions; VH-CDR3 comprising the amino acid sequence of SEQ ID NO:34, or a variant thereof comprising up to about 3 (such as about any of 1, 2, or 3) amino acid substitutions; VL-CDR1 comprising the amino acid sequence of SEQ ID NO:37, or a variant thereof comprising up to about 3 (such as about any of 1, 2, or 3) amino acid substitutions; VL-CDR2 comprising the amino acid sequence of SEQ ID NO:38, or a variant thereof comprising up to about 3 (such as about any of 1, 2, or 3) amino acid substitutions; and VL-CDR3 comprising the amino acid sequence of SEQ ID NO:39, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:32, or a variant thereof comprising up to about 3 (such as about any of 1, 2, or 3) amino acid substitutions; VH-CDR2 comprising the amino acid sequence of SEQ ID NO:33, or a variant thereof comprising up to about 3 (such as about any of 1, 2, or 3) amino acid substitutions; VH-CDR3 comprising the amino acid sequence of SEQ ID NO:34; VL-CDR1 comprising the amino acid sequence of SEQ ID NO:37, or a variant thereof comprising up to about 3 (such as about any of 1, 2, or 3) amino acid substitutions; VL-CDR2 comprising the amino acid sequence of SEQ ID NO:38, or a variant thereof comprising up to about 3 (such as about any of 1, 2, or 3) amino acid substitutions; and VL-CDR3 comprising the amino acid sequence of SEQ ID NO:39.

In some embodiments, the anti-C5 antibody or antigen-binding fragment thereof comprises: VH-CDR1 comprising the amino acid sequence of SEQ ID NO:32; VH-CDR2 comprising the amino acid sequence of SEQ ID NO:33; VH-CDR3 comprising the amino acid sequence of SEQ ID NO:34; VL-CDR1 comprising the amino acid sequence of SEQ ID NO:37; VL-CDR2 comprising the amino acid sequence of SEQ ID NO:38; and VL-CDR3 comprising the amino acid sequence of SEQ ID NO:39.

In some embodiments, the anti-C5 antibody or an antigen binding fragment thereof comprises a heavy chain comprising the amino acid sequence of SEQ ID NO:31, or a variant thereof. In other embodiments, the anti-C5 antibody comprises a light chain comprising the amino acid sequence of SEQ ID NO:36, or a variant thereof. In another embodiment, the anti-C5 antibody is mAb 9G6, or a variant thereof. The monoclonal anti-C5 antibody mAb 9G6 comprises a heavy chain comprising the amino acid sequence of SEQ ID NO:31 and a light chain comprising the amino acid sequence of SEQ ID NO:36. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO: 42; VH-CDR2: SEQ ID NO:43; VH-CDR3: SEQ ID NO:44; VL-CDR1: SEQ ID NO:47; VL-CDR2: SEQ ID NO:48; and VL-CDR3: SEQ ID NO:49, or a variant or variants thereof. In another embodiment, the anti-C5 antibody comprises all of the CDRs of the group consisting of: VH-CDR1: SEQ ID NO:42; VH-CDR2: SEQ ID NO:43; VH-CDR3: SEQ ID NO:44; VL-CDR1: SEQ ID NO:47; VL-CDR2: SEQ ID NO:48; and VL-CDR3: SEQ ID NO:49, or a variant or variants thereof.

In some embodiments, the anti-C5 antibody or antigen-binding fragment thereof comprises: VH-CDR1 comprising the amino acid sequence of SEQ ID NO:42 or a variant thereof comprising up to about 3 (such as about any of 1, 2, or 3) amino acid substitutions; and VL-CDR1: SEQ ID NO:47, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:42; and VL-CDR1: SEQ ID NO:47.

In some embodiments, the anti-C5 antibody or antigen-binding fragment thereof comprises: VH-CDR2 comprising the amino acid sequence of SEQ ID NO:43, or a variant thereof comprising up to about 3 (such as about any of 1, 2, or 3) amino acid substitutions; and VL-CDR2: SEQ ID NO:48, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:43; and VL-CDR2: SEQ ID NO:48.

In some embodiments, the anti-C5 antibody or antigen-binding fragment thereof comprises: VH-CDR3 comprising the amino acid sequence of SEQ ID NO:44, or a variant thereof comprising up to about 3 (such as about any of 1, 2, or 3) amino acid substitutions; and VL-CDR3: SEQ ID NO:49, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:44; and VL-CDR3: SEQ ID NO:49.

In some embodiments, the anti-C5 antibody or antigen-binding fragment thereof comprises: VH-CDR1 comprising the amino acid sequence of SEQ ID NO:42, or a variant thereof comprising up to about 3 (such as about any of 1, 2, or 3) amino acid substitutions; VH-CDR2 comprising the amino acid sequence of SEQ ID NO:43, or a variant thereof comprising up to about 3 (such as about any of 1, 2, or 3) amino acid substitutions; VH-CDR3 comprising the amino acid sequence of SEQ ID NO:44, or a variant thereof comprising up to about 3 (such as about any of 1, 2, or 3) amino acid substitutions; VL-CDR1 comprising the amino acid sequence of SEQ ID NO:47, or a variant thereof comprising up to about 3 (such as about any of 1, 2, or 3) amino acid substitutions; VL-CDR2 comprising the amino acid sequence of SEQ ID NO:48, or a variant thereof comprising up to about 3 (such as about any of 1, 2, or 3) amino acid substitutions; and VL-CDR3 comprising the amino acid sequence of SEQ ID NO:49, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:42, or a variant thereof comprising up to about 3 (such as about any of 1, 2, or 3) amino acid substitutions; VH-CDR2 comprising the amino acid sequence of SEQ ID NO:43, or a variant thereof comprising up to about 3 (such as about any of 1, 2, or 3) amino acid substitutions; VH-CDR3 comprising the amino acid sequence of SEQ ID NO:44; VL-CDR1 comprising the amino acid sequence of SEQ ID NO:47, or a variant thereof comprising up to about 3 (such as about any of 1, 2, or 3) amino acid substitutions; VL-CDR2 comprising the amino acid sequence of SEQ ID NO:48, or a variant thereof comprising up to about 3 (such as about any of 1, 2, or 3) amino acid substitutions; and VL-CDR3 comprising the amino acid sequence of SEQ ID NO:49.

In some embodiments, the anti-C5 antibody or antigen-binding fragment thereof comprises: VH-CDR1 comprising the amino acid sequence of SEQ ID NO:42; VH-CDR2 comprising the amino acid sequence of SEQ ID NO:43; VH-CDR3 comprising the amino acid sequence of SEQ ID NO:44; VL-CDR1 comprising the amino acid sequence of SEQ ID NO:47; VL-CDR2 comprising the amino acid sequence of SEQ ID NO:48; and VL-CDR3 comprising the amino acid sequence of SEQ ID NO:49.

In some embodiments, the anti-C5 antibody or an antigen binding fragment thereof comprises a heavy chain comprising the amino acid sequence of SEQ ID NO: 41, or a variant thereof. In other embodiments, the anti-C5 antibody comprises a light chain comprising the amino acid sequence of SEQ ID NO:46, or a variant thereof. In another embodiment, the anti-C5 antibody is mAb 1105, or a variant thereof. The monoclonal anti-C5 antibody designated mAb 1105 comprises a heavy chain comprising the amino acid sequence of SEQ ID NO:41 and a light chain comprising the amino acid sequence of SEQ ID NO:46. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:52; VH-CDR2: SEQ ID NO:53; VH-CDR3: SEQ ID NO:54; VL-CDR1: SEQ ID NO:57; VL-CDR2: SEQ ID NO:58; and VL-CDR3: SEQ ID NO:59, or a variant or variants thereof. In another embodiment, the anti-C5 antibody comprises all of the CDRs of the group consisting of: VH-CDR1: SEQ ID NO:52; VH-CDR2: SEQ ID NO:53; VH-CDR3: SEQ ID NO:54; VL-CDR1: SEQ ID NO:57; VL-CDR2: SEQ ID NO:58; and VL-CDR3: SEQ ID NO:59, or a variant or variants thereof.

In some embodiments, the anti-C5 antibody or antigen-binding fragment thereof comprises: VH-CDR1 comprising the amino acid sequence of SEQ ID NO:52 or a variant thereof comprising up to about 3 (such as about any of 1, 2, or 3) amino acid substitutions; and VL-CDR1: SEQ ID NO:57, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:52; and VL-CDR1: SEQ ID NO:57.

In some embodiments, the anti-C5 antibody or antigen-binding fragment thereof comprises: VH-CDR2 comprising the amino acid sequence of SEQ ID NO:53, or a variant thereof comprising up to about 3 (such as about any of 1, 2, or 3) amino acid substitutions; and VL-CDR2: SEQ ID NO:58, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:53; and VL-CDR2: SEQ ID NO:58.

In some embodiments, the anti-C5 antibody or antigen-binding fragment thereof comprises: VH-CDR3 comprising the amino acid sequence of SEQ ID NO:54, or a variant thereof comprising up to about 3 (such as about any of 1, 2, or 3) amino acid substitutions; and VL-CDR3: SEQ ID NO:59, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:54; and VL-CDR3: SEQ ID NO:59.

In some embodiments, the anti-C5 antibody or antigen-binding fragment thereof comprises: VH-CDR1 comprising the amino acid sequence of SEQ ID NO:52, or a variant thereof comprising up to about 3 (such as about any of 1, 2, or 3) amino acid substitutions; VH-CDR2 comprising the amino acid sequence of SEQ ID NO:53, or a variant thereof comprising up to about 3 (such as about any of 1, 2, or 3) amino acid substitutions; VH-CDR3 comprising the amino acid sequence of SEQ ID NO:54, or a variant thereof comprising up to about 3 (such as about any of 1, 2, or 3) amino acid substitutions; VL-CDR1 comprising the amino acid sequence of SEQ ID NO:57, or a variant thereof comprising up to about 3 (such as about any of 1, 2, or 3) amino acid substitutions; VL-CDR2 comprising the amino acid sequence of SEQ ID NO:58, or a variant thereof comprising up to about 3 (such as about any of 1, 2, or 3) amino acid substitutions; and VL-CDR3 comprising the amino acid sequence of SEQ ID NO:59, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:52, or a variant thereof comprising up to about 3 (such as about any of 1, 2, or 3) amino acid substitutions; VH-CDR2 comprising the amino acid sequence of SEQ ID NO:53, or a variant thereof comprising up to about 3 (such as about any of 1, 2, or 3) amino acid substitutions; VH-CDR3 comprising the amino acid sequence of SEQ ID NO:54; VL-CDR1 comprising the amino acid sequence of SEQ ID NO:57, or a variant thereof comprising up to about 3 (such as about any of 1, 2, or 3) amino acid substitutions; VL-CDR2 comprising the amino acid sequence of SEQ ID NO:58, or a variant thereof comprising up to about 3 (such as about any of 1, 2, or 3) amino acid substitutions; and VL-CDR3 comprising the amino acid sequence of SEQ ID NO:59.

In some embodiments, the anti-C5 antibody or antigen-binding fragment thereof comprises: VH-CDR1 comprising the amino acid sequence of SEQ ID NO:52; VH-CDR2 comprising the amino acid sequence of SEQ ID NO:53; VH-CDR3 comprising the amino acid sequence of SEQ ID NO:54; VL-CDR1 comprising the amino acid sequence of SEQ ID NO:57; VL-CDR2 comprising the amino acid sequence of SEQ ID NO:58; and VL-CDR3 comprising the amino acid sequence of SEQ ID NO:59.

In some embodiments, the anti-C5 antibody or an antigen binding fragment thereof comprises a heavy chain comprising the amino acid sequence of SEQ ID NO:51, or a variant thereof. In other embodiments, the anti-C5 antibody comprises a light chain comprising the amino acid sequence of SEQ ID NO:56, or a variant thereof. In another embodiment, the anti-C5 antibody is mAb 11D9, or a variant thereof. The monoclonal anti-C5 antibody designated mAb 11D9 comprises a heavy chain comprising the amino acid sequence of SEQ ID NO:51 and a light chain comprising the amino acid sequence of SEQ ID NO:56. In some embodiments, the monoclonal anti-C5 antibody is humanized. In some embodiments the monoclonal anti-C5 antibody is a chimeric antibody.

In one embodiment, the anti-C5 antibody or an antigen-binding fragment thereof comprises at least one of the CDRs selected from the group consisting of: VH-CDR1: SEQ ID NO:64; VH-CDR2: SEQ ID NO:65; VH-CDR3: SEQ ID NO:66; VL-CDR1: SEQ ID NO:74; VL-CDR2: SEQ ID NO:75; and VL-CDR3: SEQ ID NO:76, or a variant or variants thereof. In another embodiment, the anti-C5 antibody comprises all of the CDRs of the group consisting of: VH-CDR1: SEQ ID NO:64; VH-CDR2: SEQ ID NO:65; VH-CDR3: SEQ ID NO:66; VL-CDR1: SEQ ID NO:74; VL-CDR2: SEQ ID NO:75; and VL-CDR3: SEQ ID NO:76, or a variant or variants thereof.

In some embodiments, the anti-C5 antibody or antigen-binding fragment thereof comprises: VH-CDR1 comprising the amino acid sequence of SEQ ID NO:64 or a variant thereof comprising up to about 3 (such as about any of 1, 2, or 3) amino acid substitutions; and VL-CDR1: SEQ ID NO:74, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:64; and VL-CDR1: SEQ ID NO:74.

In some embodiments, the anti-C5 antibody or antigen-binding fragment thereof comprises: VH-CDR2 comprising the amino acid sequence of SEQ ID NO:65, or a variant thereof comprising up to about 3 (such as about any of 1, 2, or 3) amino acid substitutions; and VL-CDR2: SEQ ID NO:75, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:65; and VL-CDR2: SEQ ID NO:75.

In some embodiments, the anti-C5 antibody or antigen-binding fragment thereof comprises: VH-CDR3 comprising the amino acid sequence of SEQ ID NO:66, or a variant thereof comprising up to about 3 (such as about any of 1, 2, or 3) amino acid substitutions; and VL-CDR3: SEQ ID NO:76, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:66; and VL-CDR3: SEQ ID NO:76.

In some embodiments, the anti-C5 antibody or antigen-binding fragment thereof comprises: VH-CDR1 comprising the amino acid sequence of SEQ ID NO:64, or a variant thereof comprising up to about 3 (such as about any of 1, 2, or 3) amino acid substitutions; VH-CDR2 comprising the amino acid sequence of SEQ ID NO:65, or a variant thereof comprising up to about 3 (such as about any of 1, 2, or 3) amino acid substitutions; VH-CDR3 comprising the amino acid sequence of SEQ ID NO:66, or a variant thereof comprising up to about 3 (such as about any of 1, 2, or 3) amino acid substitutions; VL-CDR1 comprising the amino acid sequence of SEQ ID NO:74, or a variant thereof comprising up to about 3 (such as about any of 1, 2, or 3)

amino acid substitutions; VL-CDR2 comprising the amino acid sequence of SEQ ID NO:75, or a variant thereof comprising up to about 3 (such as about any of 1, 2, or 3) amino acid substitutions; and VL-CDR3 comprising the amino acid sequence of SEQ ID NO:76, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:64, or a variant thereof comprising up to about 3 (such as about any of 1, 2, or 3) amino acid substitutions; VH-CDR2 comprising the amino acid sequence of SEQ ID NO:65, or a variant thereof comprising up to about 3 (such as about any of 1, 2, or 3) amino acid substitutions; VH-CDR3 comprising the amino acid sequence of SEQ ID NO:66; VL-CDR1 comprising the amino acid sequence of SEQ ID NO:74, or a variant thereof comprising up to about 3 (such as about any of 1, 2, or 3) amino acid substitutions; VL-CDR2 comprising the amino acid sequence of SEQ ID NO:75, or a variant thereof comprising up to about 3 (such as about any of 1, 2, or 3) amino acid substitutions; and VL-CDR3 comprising the amino acid sequence of SEQ ID NO:76.

In some embodiments, the anti-C5 antibody or antigen-binding fragment thereof comprises: VH-CDR1 comprising the amino acid sequence of SEQ ID NO:64; VH-CDR2 comprising the amino acid sequence of SEQ ID NO:65; VH-CDR3 comprising the amino acid sequence of SEQ ID NO:66; VL-CDR1 comprising the amino acid sequence of SEQ ID NO:74; VL-CDR2 comprising the amino acid sequence of SEQ ID NO:75; and VL-CDR3 comprising the amino acid sequence of SEQ ID NO:76.

In one embodiment, the anti-C5 antibody or an antigen-binding fragment thereof comprises at least one of the CDRs selected from the group consisting of: VH-CDR1: SEQ ID NO:69; VH-CDR2: SEQ ID NO:70; VH-CDR3: SEQ ID NO:71; VL-CDR1: SEQ ID NO:74; VL-CDR2: SEQ ID NO:75; and VL-CDR3: SEQ ID NO:76, or a variant or variants thereof. In another embodiment, the anti-C5 antibody comprises all of the CDRs of the group consisting of: VH-CDR1: SEQ ID NO:69; VH-CDR2: SEQ ID NO:70; VH-CDR3: SEQ ID NO:71; VL-CDR1: SEQ ID NO:74; VL-CDR2: SEQ ID NO:75; and VL-CDR3: SEQ ID NO:76, or a variant or variants thereof.

In some embodiments, the anti-C5 antibody or antigen-binding fragment thereof comprises: VH-CDR1 comprising the amino acid sequence of SEQ ID NO:69 or a variant thereof comprising up to about 3 (such as about any of 1, 2, or 3) amino acid substitutions; and VL-CDR1: SEQ ID NO:74, or a variant thereof comprising up to about 3 (such as about any of 1, 2, or 3) amino acid substitutions. In some embodiments, the anti-C5 antibody or an antigen-binding fragment thereof comprises: VH-CDR1 comprising the amino acid sequence of SEQ ID NO:69; and VL-CDR1: SEQ ID NO:74.

In some embodiments, the anti-C5 antibody or antigen-binding fragment thereof comprises: VH-CDR2 comprising the amino acid sequence of SEQ ID NO:70, or a variant thereof comprising up to about 3 (such as about any of 1, 2, or 3) amino acid substitutions; and VL-CDR2: SEQ ID NO:75, or a variant thereof comprising up to about 3 (such as about any of 1, 2, or 3) amino acid substitutions. In some embodiments, the anti-C5 antibody or an antigen-binding fragment thereof comprises: VH-CDR2 comprising the amino acid sequence of SEQ ID NO:70; and VL-CDR2: SEQ ID NO:75.

In some embodiments, the anti-C5 antibody or antigen-binding fragment thereof comprises: VH-CDR3 comprising the amino acid sequence of SEQ ID NO:71, or a variant thereof comprising up to about 3 (such as about any of 1, 2, or 3) amino acid substitutions; and VL-CDR3: SEQ ID NO:76, or a variant thereof comprising up to about 3 (such as about any of 1, 2, or 3) amino acid substitutions. In some embodiments, the anti-C5 antibody or an antigen-binding fragment thereof comprises: VH-CDR3 comprising the amino acid sequence of SEQ ID NO:71; and VL-CDR3: SEQ ID NO:76.

In some embodiments, the anti-C5 antibody or antigen-binding fragment thereof comprises: VH-CDR1 comprising the amino acid sequence of SEQ ID NO:69, or a variant thereof comprising up to about 3 (such as about any of 1, 2, or 3) amino acid substitutions; VH-CDR2 comprising the amino acid sequence of SEQ ID NO:70, or a variant thereof comprising up to about 3 (such as about any of 1, 2, or 3) amino acid substitutions; VH-CDR3 comprising the amino acid sequence of SEQ ID NO:71, or a variant thereof comprising up to about 3 (such as about any of 1, 2, or 3) amino acid substitutions; VL-CDR1 comprising the amino acid sequence of SEQ ID NO:74, or a variant thereof comprising up to about 3 (such as about any of 1, 2, or 3) amino acid substitutions; VL-CDR2 comprising the amino acid sequence of SEQ ID NO:75, or a variant thereof comprising up to about 3 (such as about any of 1, 2, or 3) amino acid substitutions; and VL-CDR3 comprising the amino acid sequence of SEQ ID NO:76, or a variant thereof comprising up to about 3 (such as about any of 1, 2, or 3) amino acid substitutions.

In some embodiments, the anti-C5 antibody or antigen-binding fragment thereof comprises: VH-CDR1 comprising the amino acid sequence of SEQ ID NO:69, or a variant thereof comprising up to about 3 (such as about any of 1, 2, or 3) amino acid substitutions; VH-CDR2 comprising the amino acid sequence of SEQ ID NO:70, or a variant thereof comprising up to about 3 (such as about any of 1, 2, or 3) amino acid substitutions; VH-CDR3 comprising the amino acid sequence of SEQ ID NO:71; VL-CDR1 comprising the amino acid sequence of SEQ ID NO:74, or a variant thereof comprising up to about 3 (such as about any of 1, 2, or 3) amino acid substitutions; VL-CDR2 comprising the amino acid sequence of SEQ ID NO:75, or a variant thereof comprising up to about 3 (such as about any of 1, 2, or 3) amino acid substitutions; and VL-CDR3 comprising the amino acid sequence of SEQ ID NO:76.

In some embodiments, the anti-C5 antibody or antigen-binding fragment thereof comprises: VH-CDR1 comprising the amino acid sequence of SEQ ID NO:69; VH-CDR2 comprising the amino acid sequence of SEQ ID NO:70; VH-CDR3 comprising the amino acid sequence of SEQ ID NO:71; VL-CDR1 comprising the amino acid sequence of SEQ ID NO:74; VL-CDR2 comprising the amino acid sequence of SEQ ID NO:75; and VL-CDR3 comprising the amino acid sequence of SEQ ID NO:76.

In some embodiments, the anti-C5 antibody or an antigen binding fragment thereof comprises a heavy chain comprising the amino acid sequence of SEQ ID NO:68, or a variant thereof. In other embodiments, the anti-C5 antibody comprises a light chain comprising the amino acid sequence of SEQ ID NO:73, or a variant thereof. In another embodiment, the anti-C5 antibody is mAb 2G1, or a variant thereof. The monoclonal anti-C5 antibody mAb 2G1 comprises a heavy chain comprising the amino acid sequence of SEQ ID NO:68 and a light chain comprising the amino acid sequence of SEQ ID NO:73. In some embodiments, the monoclonal anti-C5 antibody is humanized. In some embodiments the monoclonal anti-C5 antibody is a chimeric antibody. In some embodiments, the anti-C5 antibody or an antigen binding fragment thereof comprises a heavy chain comprising the amino acid sequence of SEQ ID NO:63, or a variant thereof. In other embodiments, the anti-C5 antibody comprises a light chain comprising the amino acid sequence of SEQ ID NO:73, or a variant thereof. In another embodiment, the anti-C5 antibody is mAb 2G1, or a variant thereof. The monoclonal anti-C5 antibody mAb 2G1 comprises a heavy chain comprising the amino acid sequence of SEQ ID NO:63 and a light chain comprising the amino acid sequence of SEQ ID NO:73. In some embodiments, the monoclonal anti-C5 antibody is humanized. In some embodiments the monoclonal anti-C5 antibody is a chimeric antibody.

In some embodiments the antibodies are chimeric antibodies. In some embodiments the anti-human C5 antibody may comprise human light chain and human heavy chain constant regions in combination with the variable region CDR sequences described in the specification above. One of skill in the art would be able to prepare and obtain a chimeric antibody using known techniques of swapping relevant domains of specific antibodies of interest. Such an antibody is easily prepared by grafting heterogeneous antibody domains, incorporating one or more CDR sequences described in this application. Using known recombinant technology, it is possible to obtain and prepare a recombinant antibody comprising heavy and light chain constant regions encoded by nucleic acid sequences of human heavy and light chain constant regions; and the heavy and light chain variable regions comprising CDRs encoded by nucleic acid sequences corresponding to the CDR sequences set forth in the disclosure. One of skill in the art can prepare an anti-human C5 antibody comprises one or more CDR sequences described in this disclosure, wherein portions of the light chain alone or portions of the heavy chain alone are replaced with regions from an antibody belonging to another species, such as, for example, human. A human anti-human-C5 antibody comprising variable regions having one or more CDR sequences selected from SEQ ID NOs: 3-5, 8-10, 13-15, 18-20, 23-25, 28-29, 32-34, 37-39, 42-44, 47-49, 52-54 and 57-59, or a variant or variants thereof, in combination with murine or non-murine antibody structural elements outside the CDR regions can be prepared by routine methods known in the art. In some embodiments, the antibodies or antibody fragments are further humanized using known techniques in the art.

In various embodiments, any of the antibodies of the invention described herein, having any of the variable regions described herein, may comprise a human IgG4 constant heavy chain. SEQ ID NO: 104 is an example amino acid sequence of a human IgG4 constant heavy chain. In some embodiments, the antibody of the invention comprises a human IgG4 constant heavy chain having an S228P mutation. SEQ ID NO: 60 is an example amino acid sequence of a human IgG4 constant heavy chain having an S228P mutation.

In some embodiments the anti-C5 antibody comprises an antibody having at least about 85% (such as at least about any of 85%, 86%, 87%, 88%, 89%, 90%, 91%, 92%, 93%, 94%, 95%, 96%, 97%, 98%, 99%, or 100%) amino acid identity with the CDR sequence described herein, listed in SEQ ID NOs 3-5, 8-10, 13-15, 18-20, 23-25, 28-29, 32-34, 37-39, 42-44, 47-49, 52-54 and 57-59.

In one embodiment, the current disclosure encompasses an anti-C5 antibody having CDR sequences of at least about 85% (such as at least about any of 85%, 86%, 87%, 88%, 89%, 90%, 91%, 92%, 93%, 94%, 95%, 96%, 97%, 98%, 99%, or 100%) identity to the CDR sequences described above. In one embodiment, the antibody against human C5 has a heavy chain variable (vH) region and a light chain variable (vL) region, wherein the vH region has an amino acid sequence that is more than about 90% (such as more than about any of 90%, 91%, 92%, 93%, 94%, 95%, 96%, 97%, 98%, 99%, or 100%) identical to one selected from SEQ ID NOs 2, 12, 22, 31, 41, 51, 63, and 68 and wherein the vL region has an amino acid sequence that is more than about 90% (such as more than about any of 90%, 91%, 92%, 93%, 94%, 95%, 96%, 97%, 98%, 99%, or 100%) identical to one selected from SEQ ID NOs 7, 17, 27, 36, 46, 56 and 73.

In some embodiments the antibody or the antibody fragment is modified. In some embodiments the modifications include fusion of the antibody or the antigen-binding fragment thereof with portions of another protein, or a protein fragment. In some embodiments the antibody or the antibody fragment thereof of the invention is modified to increase the circulating half-life of the same in vivo. For example, the antibody of the fragment may be fused with an FcRn molecule, which is also known as neonatal Fc receptor to stabilize the antibody in vivo. (Nature Reviews Immunology 7:715-725). In some embodiments, the antibody or antigen-binding fragment thereof is conjugated (e.g., fused) to an effector molecule and/or another targeting moiety (such as an antibody or antibody fragment recognizing a different molecule, different antigen or a different epitope).

One of skill in the art would be able to prepare human-C5 binding single chain variable fragment (scFv), comprising at least one specific CDR sequence selected from SEQ ID NOs 3-5, 8-10, 13-15, 18-20, 23-25, 28-29, 32-34, 37-39, 42-44, 47-49, 52-54 and 57-59, or a variant or variants thereof. An scFv may comprise heavy chain variable region sequences designated in SEQ ID NOs 3-5, or a variant or variants thereof, and light chain variable regions designated in SEQ ID NOs 8-10, or a variant or variants thereof. An scFv may comprise heavy chain variable region sequences designated in SEQ ID NOs 13-15, or a variant or variants thereof, and light chain variable regions designated in SEQ ID NOs 18-20, or a variant or variants thereof. An scFv may comprise heavy chain variable region sequences designated in SEQ ID NOs 23-25, or a variant or variants thereof, and light chain variable regions designated in SEQ ID NOs 28-29, or a variant or variants thereof. An scFv may comprise heavy chain variable region sequences designated in SEQ ID NOs 32-34, or a variant or variants thereof, and light chain variable regions designated in SEQ ID NOs 37-39, or a variant or variants thereof. An scFv may comprise heavy chain variable region sequences designated in SEQ ID NOs 42-44, or a variant or variants thereof, and light chain variable regions designated in SEQ ID NOs 47-49, or a variant or variants thereof. An scFv may comprise heavy chain variable region sequences designated in SEQ ID NOs 52-54, or a variant or variants thereof, and light chain variable regions designated in SEQ ID NOs 57-59, or a variant or variants thereof. CDR sequences incorporated within the scFv having amino acid sequence identity of at least about 85% 86%, 87%, 88%, 89%, 90%, 91%, 92%, 93%, 94%, 95%, 96%, 97%, 98%, or 99% to the CDR sequences described in the present disclosure are encompassed within the scope of the present disclosure.

In some embodiments, the isolated antibody binds to human C5, wherein the antibody binds to an epitope of human C5. In some embodiments, the human C5 antibody of the invention is one that binds to a specific epitope of human C5. In some embodiments, the epitope includes at least one amino acid in the α-chain of C5. In some embodiments, the epitope includes at least one amino acid in the β-chain of C5.

In some embodiments, the epitope includes at least one amino acid in the MG7 domain of the α-chain of C5. In some embodiments, the epitope includes at least one amino acid in the CUB domain of the α-chain of C5. In some embodiments, the epitope includes at least one amino acid in the C5d domain of the α-chain of C5. In some embodiments, the epitope includes at least one amino acid in the MG8 domain of the α-chain of C5. In some embodiments, the epitope includes at least one amino acid in the C345C domain of the α-chain of C5.

In some embodiments, the epitope includes at least one amino acid in the MG1 domain of the β-chain of C5. In some embodiments, the epitope includes at least one amino acid in the MG2 domain of the β-chain of C5. In some embodiments, the epitope includes at least one amino acid in the MG3 domain of the β-chain of C5. In some embodiments, the epitope includes at least one amino acid in the MG4 domain of the β-chain of C5. In some embodiments, the epitope includes at least one amino acid in the MG5 domain of the β-chain of C5. In some embodiments, the epitope includes at least one amino acid in the MG6 domain of the β-chain of C5.

In some embodiments, the antibody, or binding portion thereof, binds to at least one amino acid in the MG7 domain of the α-chain of C5. In some embodiments, the antibody, or binding portion thereof, binds to at least one amino acid in the CUB domain of the α-chain of C5. In some embodiments, the antibody, or binding portion thereof, binds to at least one amino acid in the C5d domain of the α-chain of C5. In some embodiments, the antibody, or binding portion thereof, binds to at least one amino acid in the MG8 domain of the α-chain of C5. In some embodiments, the antibody, or binding portion thereof, binds to at least one amino acid in the C345C domain of the α-chain of C5.

In some embodiments, the antibody, or binding portion thereof, binds to at least one amino acid in the MG1 domain of the β-chain of C5. In some embodiments, the antibody, or binding portion thereof, binds to at least one amino acid in the MG2 domain of the β-chain of C5. In some embodiments, the antibody, or binding portion thereof, binds to at least one amino acid in the MG3 domain of the β-chain of C5. In some embodiments, the antibody, or binding portion thereof, binds to at least one amino acid in the MG4 domain of the β-chain of C5. In some embodiments, the antibody, or binding portion thereof, binds to at least one amino acid in the MG5 domain of the β-chain of C5. In some embodiments, the antibody, or binding portion thereof, binds to at least one amino acid in the MG6 domain of the β-chain of C5.

In one embodiment, at least one (such as at least 1, 2, 3, or 4) of the amino acids of SEQ ID NO: 84 is in the epitope of the human C5 antibody. In one embodiment, at least one (such as at least 1, 2, 3, or 4) of the amino acids of SEQ ID NO: 85 is in the epitope of the human C5 antibody. In one embodiment, at least one (such as at least 1, 2, 3, or 4) of the amino acids of SEQ ID NO: 86 is in the epitope of the human C5 antibody. In one embodiment, at least one (such as at least 1, 2, 3, or 4) of the amino acids of SEQ ID NO: 87 is in the epitope of the human C5 antibody. In one embodiment, at least one (such as at least 1, 2, 3, or 4) of the amino acids of SEQ ID NO: 88 is in the epitope of the human C5 antibody. In one embodiment, at least one (such as at least 1, 2, 3, or 4) of the amino acids of SEQ ID NO: 89 is in the epitope of the human C5 antibody.

In one embodiment, the antibody, or binding fragment thereof, of the invention binds to at least one (such as at least 1, 2, 3, or 4) of the amino acids of SEQ ID NO: 84. In one embodiment, the antibody, or binding fragment thereof, of the invention binds to at least one (such as at least 1, 2, 3, or 4) of the amino acids of SEQ ID NO: 85. In one embodiment, the antibody, or binding fragment thereof, of the invention binds to at least one (such as at least 1, 2, 3, or 4) of the amino acids of SEQ ID NO: 86. In one embodiment, the antibody, or binding fragment thereof, of the invention binds to at least one (such as at least 1, 2, 3, or 4) of the amino acids of SEQ ID NO: 87. In one embodiment, the antibody, or binding fragment thereof, of the invention binds to at least one (such as at least 1, 2, 3, or 4) of the amino acids of SEQ ID NO: 88 In one embodiment, the antibody, or binding fragment thereof, of the invention binds to at least one (such as at least 1, 2, 3, or 4) of the amino acids of SEQ ID NO: 89.

Screening Assays

The present invention has application in various screening assays, including, determining whether a candidate anti-C5 antibody can inhibit complement activity.

In some embodiments, the level of complement activity in the presence of the candidate anti-C5 antibody is compared with complement activity detected in a positive comparator control. The positive comparator control comprises complement activation in the absence of added test compound. In some embodiments, the candidate anti-C5 antibody is identified as an inhibitor of the complement when the complement activity in the presence of the candidate anti-C5 antibody is less than about 70% of the complement activity detected in a positive comparator control; this corresponds to greater than about 30% inhibition of complement activity in the presence of the test compound. In other embodiments, the candidate anti-C5 antibody is identified as an inhibitor of the complement when the complement activity in the presence of the candidate anti-C5 antibody is less than about 80% of the complement activity detected in a positive comparator control; this corresponds to greater than about 20% inhibition of complement activity in the presence of the test compound. In still other embodiments, the candidate anti-C5 antibody is identified as an inhibitor of the complement when the complement activity in the presence of the candidate anti-C5 antibody is less than about 90% of the complement activity detected in a positive comparator control; this corresponds to greater than about 10% inhibition of complement activity in the presence of the test compound. In some embodiments, the level of complement inhibition by the candidate anti-C5 antibody is compared with the level of inhibition detected in a negative comparator control.

A variety of immunoassay formats, including competitive and non-competitive immunoassay formats, antigen capture assays, two-antibody sandwich assays, and three-antibody sandwich assays are useful methods of the invention (Self et al., 1996, Curr. Opin. Biotechnol. 7:60-65). The invention should not be construed to be limited to any one type of known or heretofor unknown assay, provided that the assay is able to detect the inhibition of complement.

Enzyme-linked immunosorbent assays (ELISAs) are useful in the methods of the invention. An enzyme such as, but not limited to, horseradish peroxidase (HRP), alkaline phosphatase, beta-galactosidase or urease can be linked, for example, to an anti-C3 antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Chemiluminescent detection is also useful for detecting the inhibition of the AP. Chemiluminescent secondary antibodies may be obtained from any number of commercial sources.

Fluorescent detection is also useful for detecting the inhibition of the AP. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antibodies.

Radioimmunoassays (RIAs) are also useful in the methods of the invention. Such assays are well known in the art, and are described for example in Brophy et al. (1990, Biochem. Biophys. Res. Comm. 167:898-903) and Guechot et al. (1996, Clin. Chem. 42:558-563). Radioimmunoassays are performed, for example, using Iodine-125-labeled primary or secondary antibody (Harlow et al., supra, 1999).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis is performed using a spectrophotometer. It is understood that the assays of the invention can be performed manually or, if desired, can be automated and that the signal emitted from multiple samples can be detected simultaneously in many systems available commercially.

The methods of the invention also encompass the use of capillary electrophoresis based immunoassays (CEIA), which can be automated, if desired. Immunoassays also may be used in conjunction with laser-induced fluorescence as described, for example, in Schmalzing et al. (1997, Electrophoresis 18:2184-2193) and Bao (1997, J. Chromatogr. B. Biomed. Sci. 699:463-480). Liposome immunoassays, such as flow-injection liposome immunoassays and liposome immunosensors, may also be used according to the methods of the invention (Rongen et al., 1997, J. Immunol. Methods 204:105-133).

Quantitative western blotting may also be used to determine the level of complement inhibition in the methods of the invention. Western blots are quantified using well known methods such as scanning densitometry (Parra et al., 1998, J. Vasc. Surg. 28:669-675).

Methods of Administration

The methods of the invention comprise administering a therapeutically effective amount of at least one anti-C5 antibody, or binding fragment thereof (such as any of the antibodies or fragments thereof described elsewhere herein), to an individual identified as having a complement-mediated disease or disorder. In one embodiment the individual is a mammal having a complement system. In one embodiment the individual is a human. In various embodiments, the at least one anti-C5 antibody, or binding fragment thereof, is administered locally, regionally, or systemically.

In various embodiments, the disease or disorder is at least selected from the group consisting of: macular degeneration (MD), age-related macular degeneration (AMD), ischemia reperfusion injury, arthritis, rheumatoid arthritis, asthma, allergic asthma, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the AP-mediated disease is C3 glomerulopathy. In some embodiments, the AP-mediated disease is macular degeneration, such as age-related macular degeneration. In one embodiment, administration of the anti-C5 antibody inhibits the generation of a C5a or C5b protein. In some embodiments, the compositions and methods of the invention are useful for treating subject, including subjects having PNH, who are not responsive to treatment with eculizumab. By way of non-limiting example, some subjects may have a mutation in the alpha chain of C5 that may render them resistant to treatment of eculizumab (see Genetic variants in C5 and poor response to eculizumab. Nishimura J, et al., N Engl J Med. 2014 Feb. 13; 370(7):632-9).

The methods of the invention can comprise the administration of at least one anti-C5 antibody, or binding fragment thereof, but the present invention should in no way be construed to be limited to the anti-C5 antibodies described herein, but rather should be construed to encompass any anti-C5 antibody, both known and unknown, that diminish and reduce complement activation.

The method of the invention comprises administering a therapeutically effective amount of at least one anti-C5 antibody, or binding fragment thereof, to an individual wherein a composition of the present invention comprising at least one anti-C5 antibody, or binding fragment thereof, either alone or in combination with at least one other therapeutic agent. The invention can be used in combination with other treatment modalities, such as, for example anti-inflammatory therapies, and the like. Examples of anti-inflammatory therapies that can be used in combination with the methods of the invention include, for example, therapies that employ steroidal drugs, as well as therapies that employ non-steroidal drugs.

The method of the invention comprises administering a therapeutically effective amount of an anti-C5 antibody, or an antigen-binding fragment thereof, to a subject. In some embodiments, the invention encompasses a method of treatment of C5 related diseases involving dysregulation of the complement signaling by administering a therapeutically effective amount of an antibody of the invention, or a therapeutically effective amount of an antibody fragment thereof, such that a reduction of C5a or C5b or MAC formation is effected in the subject. In some embodiments the invention encompasses a method of treatment of C5 related diseases involving dysregulation of complement signaling by administering a therapeutically effective amount of an antibody or an antibody fragment. In some embodiments the invention encompasses a method of treatment of C5 related diseases involving dysregulation of complement signaling by administering to a subject an effective amount of an antibody, an antibody fragment, a polypeptide, a peptide, a conjugated peptide, such that the complement activation pathway activation is reduced in the subject. In some embodiments, the method of treatment encompasses administering to a subject a systemically effective dose of an antibody or an antibody fragment, whereby systemic reduction of C5a or C5b or MAC formation is effected in the subject.

The pharmaceutical compositions useful for practicing the invention may be administered to deliver a dose of at least about 1 ng/kg, at least about 5 ng/kg, at least about 10 ng/kg, at least about 25 ng/kg, at least about 50 ng/kg, at least about 100 ng/kg, at least about 500 ng/kg, at least about 1 µg/kg, at least about 5 µg/kg, at least about 10 µg/kg, at least about 25 µg/kg, at least about 50 µg/kg, at least about 100 µg/kg, at least about 500 µg/kg, at least about 1 mg/kg, at least about 5 mg/kg, at least about 10 mg/kg, at least about 25 mg/kg, at least about 50 mg/kg, at least about 100 mg/kg, at least about 200 mg/kg, at least about 300 mg/kg, at least about 400 mg/kg, and at least about 500 mg/kg of body weight of the subject. In one embodiment, the invention administers a dose which results in a concentration of the anti-C5 antibody of the present invention of at least about 1 pM, at least about 10 pM, at least about 100 pM, at least about 1 nM, at least about 10 nM, at least about 100 nM, at least about 1 µM, at least about 2 µM, at least about 3 µM, at least about 4 µM, at least about 5 µM, at least about 6 µM, at least about 7 µM, at least about 8 µM, at least about 9 µM and at least about 10 µM in an individual. In another embodiment, the invention envisions administration of a dose which results in a concentration of the anti-C5 antibody of the present invention between at least about 1 pM, at least about 10 pM, at least about 100 pM, at least about 1 nM, at least about 10 nM, at least about 100 nM, at least about 1 µM, at least about 2 µM, at least about 3 µM, at least about 4 µM, at least about 5 µM, at least about 6 µM, at least about 7 µM, at least about 8 µM, at least about 9 µM and at least about 10 µM in the plasma of an individual.

In some embodiments, the pharmaceutical compositions useful for practicing the invention may be administered to deliver a dose of no more than about 1 ng/kg, no more than about 5 ng/kg, no more than about 10 ng/kg, no more than about 25 ng/kg, no more than about 50 ng/kg, no more than about 100 ng/kg, no more than about 500 ng/kg, no more than about 1 µg/kg, no more than about 5 µg/kg, no more than about 10 µg/kg, no more than about 25 µg/kg, no more than about 50 µg/kg, no more than about 100 µg/kg, no more than about 500 µg/kg, no more than about 1 mg/kg, no more than about 5 mg/kg, no more than about 10 mg/kg, no more than about 25 mg/kg, no more than about 50 mg/kg, no more than about 100 mg/kg, no more than about 200 mg/kg, no more than about 300 mg/kg, no more than about 400 mg/kg, and no more than about 500 mg/kg of body weight of the subject. In one embodiment, the invention administers a dose which results in a concentration of the anti-C5 antibody of the present invention of no more than about 1 pM, no more than about 10 pM, no more than about 100 pM, no more than about 1 nM, no more than about 10 nM, no more than about 100 nM, no more than about 1 µM, no more than about 2 µM, no more than about 3 µM, no more than about 4 µM, no more than about 5 µM, no more than about 6 µM, no more than about 7 µM, no more than about 8 µM, no more than about 9 µM and no more than about 10 µM in an individual. In another embodiment, the invention envisions administration of a dose which results in a concentration of the anti-C5 antibody of the present invention between no more than about 1 pM, no more than about 10 pM, no more than about 100 pM, no more than about 1 nM, no more than about 10 nM, no more than about 100 nM, no more than about 1 µM, no more than about 2 µM, no more than about 3 µM, no more than about 4 µM, no more than about 5 µM, no more than about 6 µM, no more than about 7 µM, no more than about 8 µM, no more than about 9 µM and no more than about 10 µM in the plasma of an individual. Also contemplated are dosage ranges between any of the doses disclosed herein.

Typically, dosages which may be administered in a method of the invention to a subject, in some embodiments a human, range in amount from 0.5 µg to about 50 mg per kilogram of body weight of the subject. While the precise dosage administered will vary depending upon any number of factors, including but not limited to, the type of subject and type of disease state being treated, the age of the subject and the route of administration. In some embodiments, the dosage of the compound will vary from about 1 µg to about 10 mg per kilogram of body weight of the subject. In other embodiments, the dosage will vary from about 3 µg to about 1 mg per kilogram of body weight of the subject.

The antibody may be administered to a subject as frequently as several times daily, or it may be administered less frequently, such as once a day, twice a day, thrice a day, once a week, twice a week, thrice a week, once every two weeks, twice every two weeks, thrice every two weeks, once a month, twice a month, thrice a month, or even less frequently, such as once every several months or even once or a few times a year or less. The frequency of the dose will be readily apparent to the skilled artisan and will depend upon any number of factors, such as, but not limited to, the type and severity of the disease being treated, the type and age of the subject, etc. The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various subjects is well understood, and the ordinarily skilled veterinary pharmacologist can design and perform such modification with merely ordinary, if any, experimentation. Individuals to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intraocular, intravitreal, intramuscular, intradermal and intravenous routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to an individual or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the individual treated and further depending upon the route by which the composition is to be administered. By way of example, the composition may comprise between 0.1% and 100% (w/w) active ingredient. In various embodiments, the composition comprises at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Parenteral administration of a pharmaceutical composition includes any route of administration characterized by physical breaching of a tissue of an individual and administration of the pharmaceutical composition through the breach in the tissue. Parental administration can be local, regional or systemic. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraocular, intravitreal, subcutaneous, intraperitoneal, intramuscular, intradermal, intrasternal injection, and intratumoral.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and in some embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. In some embodiments, dry powder compositions include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. In some embodiments, the droplets provided by this route of administration have an average diameter in the range from about 0.1 to about 200 nanometers.

The formulations are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more additional ingredients.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more additional ingredients. Alternately, formulations suitable for buccal administration may comprise a powder or an aerosolized or atomized solution or suspension comprising the active ingredient. In some embodiments, such powdered, aerosolized, or aerosolized formulations, when dispersed, have an average particle or droplet size in the range from about 0.1 to about 200 nanometers, and may further comprise one or more additional ingredients.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Cells Producing Antibodies and Antigen Binding Fragments Thereof

In some embodiments, the invention is a cell or cell line (such as host cells) that produces at least one of the anti-C5 antibodies, or antigen binding fragments, described herein. In one embodiment, the cell or cell line is a genetically modified cell that produces at least one of the anti-C5 antibodies, or antigen binding fragments, described herein. In one embodiment, the cell or cell line is a hybridoma that produces at least one of the anti-C5 antibodies, or antigen binding fragments, described herein.

Hybrid cells (hybridomas) are generally produced from mass fusions between murine splenocytes, which are highly enriched for B-lymphocytes, and myeloma "fusion partner cells" (Alberts et al., Molecular Biology of the Cell (Garland Publishing, Inc. 1994); Harlow et al., Antibodies. A Laboratory Manual (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are referred to as monoclonal antibodies.

Also provided are nucleic acids encoding any of the antibodies, or antibody fragments, disclosed herein, as well as vectors comprising the nucleic acids. Thus, the antibodies and fragments of the invention can be generated by expressing the nucleic acid in a cell or a cell line, such as the cell lines typically used for expression of recombinant or humanized immunoglobulins. Thus, the antibodies and fragments of the invention can also be generated by cloning the nucleic acids into one or more expression vectors, and transforming the vector into a cell line such as the cell lines typically used for expression of recombinant or humanized immunoglobulins.

The genes encoding the heavy and light chains of immunoglobulins, or fragments thereof, can be engineered according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al., 1992, J. Immunol. 148:1149). For example, genes encoding heavy and light chains, or fragments thereof, can be cloned from an antibody secreting cell's genomic DNA, or cDNA is produced by reverse transcription of the cell's RNA. Cloning is accomplished by conventional techniques including the use of PCR primers that hybridize to the sequences flanking or overlapping the genes, or segments of genes, to be cloned.

Nucleic acids encoding the antibody of the invention, or the heavy chain or light chain or fragments thereof, can be obtained and used in accordance with recombinant nucleic acid techniques for the production of the specific immunoglobulin, immunoglobulin chain, or a fragment or variant thereof, in a variety of host cells or in an in vitro translation system. For example, the antibody-encoding nucleic acids, or fragments thereof, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

In some embodiments, the heavy and light chains, or fragments thereof, can be assembled in two different expression vectors that can be used to co-transfect a recipient cell. In some embodiments, each vector can contain two or more selectable genes, one for selection in a bacterial system and one for selection in a eukaryotic system. These vectors allow for the production and amplification of the genes in a bacterial system, and subsequent co-transfection of eukaryotic cells and selection of the co-transfected cells. The selection procedure can be used to select for the expression of antibody nucleic acids introduced on two different DNA vectors into a eukaryotic cell.

Alternatively, the nucleic acids encoding the heavy and light chains, or fragments thereof, may be expressed from one vector. Although the light and heavy chains are coded for by separate genes, they can be joined, using recombinant methods. For example, the two polypeptides can be joined by a synthetic linker that enables them to be made as a single protein chain in which the $V_L$ and $V_H$ regions pair to form monovalent molecules (known as single chain Fv (scFv); see e.g., Bird et al., 1988, Science 242: 423-426; and Huston et al., 1988, Proc. Natl. Acad. Sci. USA 85:5879-5883).

The invention provides for an isolated nucleic acid molecule comprising a nucleic acid sequence encoding a heavy chain and/or a light chain, as well as fragments thereof. A nucleic acid molecule comprising sequences encoding both the light and heavy chain, or fragments thereof, can be engineered to contain a synthetic signal sequence for secretion of the antibody, or fragment, when produced in a cell. Furthermore, the nucleic acid molecule can contain specific DNA links which allow for the insertion of other antibody sequences and maintain the translational reading frame so to not alter the amino acids normally found in antibody sequences.

In accordance with the present invention, antibody-encoding nucleic acid sequences can be inserted into an appropriate expression vector. In various embodiments, the expression vector comprises the necessary elements for transcription and translation of the inserted antibody-encoding nucleic acid so as to generate recombinant DNA molecules that direct the expression of antibody sequences for the formation of an antibody, or a fragment thereof.

The antibody-encoding nucleic acids, or fragments thereof, can be subjected to various recombinant nucleic acid techniques known to those skilled in the art such as site-directed mutagenesis.

A variety of methods can be used to express nucleic acids in a cell. Nucleic acids can be cloned into a number of types of vectors. However, the present invention should not be construed to be limited to any particular vector. Instead, the present invention should be construed to encompass a wide variety of vectors which are readily available and/or known in the art. For example, the nucleic acid of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Viral vector technology is well known in the art and is described, for example, in Sambrook et al. (2012), and in Ausubel et al. (1999), and in other virology and molecular biology manuals. Viruses, which are useful as vectors include, but are not limited to, retroviruses, adenoviruses, adeno-associated viruses, herpes viruses, and lentiviruses. In some embodiments, a murine stem cell virus (MSCV) vector is used to express a desired nucleic acid. MSCV vectors have been demonstrated to efficiently express desired nucleic acids in cells. However, the invention should not be limited to only using a MSCV vector, rather any retroviral expression method is included in the invention. Other examples of viral vectors are those based upon Moloney Murine Leukemia Virus (MoMuLV) and HIV. In some embodiments, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

Additional regulatory elements, e.g., enhancers, can be used modulate the frequency of transcriptional initiation. A promoter may be one naturally associated with a gene or nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high-level expression of the introduced DNA segment, such as is advantageous in the large-scale production of recombinant proteins and fragments thereof.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter or cell-type specific promoter, which is a promoter that is active only in a desired tissue or cell. Tissue-specific promoters are well known in the art and include, but are not limited to, the HER-2 promoter and the PSA associated promoter sequences.

In order to assess the expression of the nucleic acids, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate nucleic acid and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing nucleic acids into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, laserporation and the like. Methods for producing cells comprising vectors and/or exogenous nucleic acids are well-known in the art. See, for example, Sambrook et al. (2012) and Ausubel et al. (1999).

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The preparation and use of such systems is well known in the art.

Regardless of the method used to introduce exogenous nucleic acids into a host cell or otherwise expose a cell to the nucleic acid of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Kits

The invention also includes a kit comprising an anti-C5 antibody, or combinations thereof, of the invention and an instructional material which describes, for instance, administering the anti-C5 antibody, or combinations thereof, to an individual as a therapeutic treatment or a non-treatment use as described elsewhere herein. In an embodiment, this kit further comprises a (optionally sterile) pharmaceutically acceptable carrier suitable for dissolving or suspending the therapeutic composition, comprising an anti-C5 antibody, or combinations thereof, of the invention, for instance, prior to administering the antibody to an individual. Optionally, the kit comprises an applicator for administering the antibody.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore and are not to be construed as limiting in any way the remainder of the disclosure.

Example 1

The complement system is part of innate immunity that plays a key role in host defense. However, activated complement also has the potential to cause significant tissue injury and destruction and dysregulated complement activity has been found to be associated with a number of rare and common diseases such as paroxysmal nocturnal hemoglobinuria (PNH), atypical hemolytic uremic syndrome, rheumatoid arthritis, age-related macular degeneration etc. Thus, anti-complement therapy is a promising way of treating these human disorders.

Complement C5 is a critical protein in the terminal pathway of complement activation and is the precursor protein for generating the potent pro-inflammatory mediator C5a, as well as the cytolytic membrane attack complex (MAC).

Six 6 murine anti-human C5 monoclonal antibodies have been generated, and have characterized and confirmed them to be function-blocking mAbs against human C5, they blocked both C5a production and MAC formation when complement is activated by either the classical, lectin or alternative pathways. The identities of these mAbs are as follows: mAbs 4E7, 9G6, 11C5, 2G1, 11D9 and 8E1.

Furthermore, the Ig subtypes of the heavy and light chains of the above mentioned antibodies have been determined, and have cloned the cDNAs of the variable regions of the heavy chains of the 6 mAbs.

The methods and material used in this example are now described.

Affinity Analysis of Anti-C5 mAbs:

Surface Plasmon resonance analysis was used to measure the association and dissociation rate constant for binding of human C5 to anti-C5 mAbs using BIAcore 3000 instrument (Biacore AB, Uppsala, Sweden) and all Biacore experiments were performed at 25° C. The carboxylated dextran matrix of a CM5 sensor chip was used to couple the purified αmRabbit IgG (RAMFc) mAb by amine coupling chemistry to obtain 1000 RU surface density, anti-C5 mAbs were captured on immobilized RAMFc. After stabilization of anti-C5 mAb binding, varying concentration of human C5 ranging from 100, 50, 25, 12.5, 6.25 and 0 nM was injected on to the surface in HBSET (HEPES buffer saline EDTA with Tween 20) buffer and the samples were injected on the antibody surface at 30 μl/min (60 μl injection) for 180 s and dissociation of bound analyte was allowed to proceed for 900 s. The data were analyzed by the BIA evaluation software 3.2 assuming 1:1 binding model. Regeneration of the surface was achieved with a 50 μl injection (50 μl/min) of 10 mM Glycone HCl pH 1.5.

LPS-Induced C5a Production Assay:

10% normal human serum (NHS) was pre incubated with different concentration of 4E7, 9G6, 11C5, 2G1, 11D9 and 8E1 at 4° C. for 1 hr. The antibody-treated samples were incubated with LPS in the Mg-EGTA GVB2+ at 37 □C for 1 hour, and then stopped with 40 mM EDTA in PBS.

Sandwich ELISA for Detection of Human C5a:

96-well plates were coated with a mouse anti-human C5a-specific antibody (R&D systems #MAB2037) at a final concentration of 1 μg/ml at 4° C. overnight. Following three washes with PBS containing 0.05% Tween-20, the plates were incubated with ⅛ diluted serum samples (from LPS-induced C5a production assay) at room temperature for 1 hr. After another wash, the plates were incubated with the corresponding biotinylated anti-human C5a mAb (R&D systems #BAM20371) at room temperature for 1 h, washed again and incubated with streptavidin conjugated to horseradish peroxidase (BD pharmagen #554058) at room temperature for 1 hr. After final washing, the plate was developed with HRP substrate for 6-10 min. The reaction was stopped with 2N $H_2SO_4$ and plate was read at 450 nm in a micro plate Human C5 and mAb Binding Assay:

Polystyrene microtiter plates were coated with purified human C5 (50 ng/well) in PBS at 37° C. for 1 hr. After aspirating the C5 solution, wells were blocked with PBS containing 1% BSA in PBS at room temperature for 1 hr. Wells without C5 coating served as background controls. Different concentration of 4E7, 9G6, 11C5, 2G1, 11D9 and 8E1, 50 μl/well in blocking solution, were added to the wells. Following a 1 hour incubation at room temperature, the wells were extensively washed with PBST. Human C5-bound mAb was detected by the addition of anti-mouse IgG HRP or anti-human IgG4 HRP 1:4000 dilution in blocking solution, which was allowed to incubate for 1 h at RT. After washing with PBST, the plate was developed with HRP substrate for 6-10 min. The reaction was stopped with 2N H2SO4 and plate was read at 450 nm in a micro plate reader.

Generation of Anti-Human C5 mAbs:

B10.D2/oSnJ female (Stock #000461, Jackson laboratory) mice were immunized with 30 μg of purified human C5 (#A120, Complement Technology Inc.) emulsified with adjuvant. At day 14, the mice were again immunized with 30 μg of purified human C5 emulsified with adjuvant. Mice were boosted with 33 μg of purified human C5 three times before fusion. Then, mice were sacrificed by cervical dislocation and spleen was isolated for preparation of single cell suspension by mechanical disruption. The spleen cell suspension was washed once with HYB-SFM (Invitrogen)+ 10% FBS medium and cells were counted, and mixed with X63-Ag8.653 myeloma cells (ATCC) in a 2:1 ratio. Cell mixture was again washed with HYB-SFM medium, and the cell pellet was prepared by centrifugation (1000 rpm×5 min). The cell pellet was gently disturbed and loosened and then cell fusion was induced by slowly adding poly ethylene glycol (PEG 1500) (1.5 ml PEG for 3×108 cells). The cells were left for 1 min at 37° C. and then 20 ml HYB-SFM medium were added to the cells in 3 min (1 ml for the first minute, 3 ml for the second minute and 16 ml for the third minute). The mixture was centrifuged at 1000 rpm for 5 min and the cells were plated in 24 well plates in HAT medium (10 ml HAT [Sigma H0262], 5 ml Pen/Strep, 500 μl Gentamicin and 10% FBS in 500 ml HYB-SFM medium). After 2 weeks, supernatants from wells with visible colonies were withdrawn for screening of reactivity with purified human C5 by ELISA, Positive clones were picked up and plated in 96 well plates by limiting dilution method to obtain single clones after second round screening by ELISA. Positive clones were expanded in HT-medium (10 ml HT, 5 ml Pen/Strep 500 μl Gentamicin and 10% FBS in 500 ml HYB-SFM medium). Before antibody collection, the hybridoma cells were switched to serum-free medium (HYB-SFM) for 2-3 days. Cell culture medium was collected for mAb purification by protein G affinity chromatography.

mAb Cloning:

To clone the cDNAs of 4E7, 9G6, 11C5, 2G1, 11D9 and 8E1, total RNAs were isolated from the hybridoma cells by TRizol reagent (Sigma). First-strand cDNAs were synthesized by reverse transcription using Oligo(dT) primer, To amplify the heavy chain cDNAs (for IgG1, IgG2a/b), the following primers were used in PCR reactions: 5'-GAGGTGAAGCTGGTGGAG(T/A)C(T/A)GG-3' (SEQ ID NO: 77) and 5'-GGGGCCAGTGGATAGAC-3' (SEQ ID NO; 78). To amplify the k light chain, the following primers were used: mixture of 4 upstream primers: 5'-CCAGTTCCGAGCTCCAGATGACCCAGACTCCA-3' (SEQ ID NO: 79); 5'-CCAGTTCCGAGCTCGTGCTCACCCAGTCTCCA-3' (SEQ ID NO:80); 5'-CCAGTTCCGAGCTCCAGATGACCCAGTCTCCA-3' (SEQ ID NO:81); 5'-CCAGTTCCGAGCTCGTGATGACACAGTCTCCA-3' (SEQ 1D NO:82); downstream primer: 5'-GTTGGTGCAGCATCAGC-3, (SEQ ID NO:83). The PCR amplicons were cloned into pCR TOPO TA 2.1 vector (Invitrogen) and sequenced. To obtain the signal peptide (leader) sequence of the mAbs, the 5'-RACE method was used with a kit (GeneRacer) from Invitrogen. The complete variable region cDNAs were amplified using specific primers determined from the 5'-RACE and the initial sequencing data.

Construction and Expression of Chimeric 2G1 mAb

Chimeric 2G1 heavy chain cDNA was constructed by cloning the variable region of mAb 2G1 into the pFUSE-CHIg-hG4 vector (from InvivoGen, containing the human IgG4 heavy chain constant region, with Serine 229 mutated to Proline (SEQ ID NO:60) using EcoRI/NheI sites. Chimeric 2G1 light chain cDNA was constructed by cloning the variable region of mAb 2G1 into the pFUSE2-CLIg-hk vector (from invivoGen, containing the human k light chain constant region (SEQ ID NO 61)) using AgeI/BsiWI sites. CHO cells were co-transfected with chimeric heavy and light chains of 2G1 or humanized heavy and light chains of 2G1 (the two humanized heavy chains were paired with the same humanized light chain) using Lipofectamine reagent. After transfection, CHO cells were selected with Geocine (1 mg/ml) and Blastcidine (10 □g/ml) for approximately 7 days. Drug-resistant cell colonies were picked up, trypsinized and subjected to limited dilution culture in 96-well plates in the presence of the same selection drugs. After ceils became confluent in the 96-well plates, the medium was tested for reactivity with human C5 by ELISA and positive clones were expanded. For antibody production, stable lines of transfected CHO cells were grown in DMEM: F 12 medium with 10% FBS in 150 cm culture flasks and after reaching confluence, they were switched to serum free CD-CHO medium (Invitrogen), After 3 days, the medium was collected and Abs were purified by protein G chromatography. Aliquots of the purified Abs were analyzed by SDS-PAGE.

Construction and Expression of Humanized 2G1 mAb mAb 2G1 CDRs of VH and VL were grafted onto the frameworks of germline variable and joining (V, J) gene segments of human Ig heavy and light chains, respectively by which were chosen based on the CDR similarities between human immunoglobulins and mAb 2G1 (Hwang et al, Method, 2005). The advantage of this approach is to generate humanized Abs that retain their binding affinity to their cognate antigen and is to highly reduce the potential immunogenicity of non-human Abs since all residues in frameworks are from human Ab germline sequences. Humanized 2G1 heavy chain cDNAs were constructed by cloning the humanized heavy chain variable region of 2G1 (Synthesized by Genescript) into the pFUSE-CHIg-hG4 vector (from InvivoGen, containing the human IgG4 heavy chain constant region, with Serine 229 mutated to Proline (SEQ ID NO 60)) using EcoRI/NheI sites. Humanized 2G1 light chain cDNA was constructed by cloning the humanized light chain variable region of 2G1 (Synthesized by Genescript) into the pFUSE2-CLIg-hk vector (from InvivoGen, containing the human kappa light chain constant region (SEQ ID NO 61)) using AgeI/BsiWI sites. CHO cells were co-transfected with chimeric heavy and light chains of 2G1 or humanized heavy and light chains of 2G1 (the two humanized heavy chains were paired with the same humanized light chain) using Lipofectamine reagent. After transfection, CHO cells were selected with Geocine (1 mg/ml) and Blastcidine (10 µg/ml) for approximately 7 days. Drug-resistant cell colonies were picked up, trypsinized and subjected to limited dilution culture in 96-well plates in the presence of the same selection drugs. After ceils became confluent in the 96-well plates, the medium was tested for reactivity with human C5 by ELISA and positive clones were expanded. For antibody production, stable lines of transfected CHO cells were grown in DMEM: F 12 medium with 10% FBS in 150 cm culture flasks and after reaching confluence, they were switched to serum free CD-CHO medium (Invitrogen), After 3 days, the medium was collected and Abs were purified by protein G chromatography. Aliquots of the purified Abs were analyzed by SDS-PAGE.

Hemolysis Assay:

Sheep red blood cell (RBCs) lysis assay: Sheep RBCs ($1\times10^7$ or $1\times10^8$ cells, Complement Technology Inc.) were incubated at 37° C. for 20 min with 10% or 50% NHS (Complement Technology Inc.) in gelatin veronal buffer (GVB2+, Sigma). Before addition to the sheep RBCs, NHS was pre-incubated with mAb (4E7, 9G6, 11C5, 2G1, 11D9, 8E1 and a control mAb 7A12) or chimeric 2G1 and 7A12, or humanized 2G1 for 1 hour at 4° C. Lysis reaction was stopped by addition of ice-cold 40 mM EDTA in PBS. The incubation mixtures were centrifuged for 5 min at 1500 rpm and the supernatant was collected and measured for $OD_{405}$ nm. Samples without NHS or with EDTA added were used as negative lysis controls, and a sample of sheep RBCs lysed completely with distilled water was used as a positive control (100% lysis) against which % lysis in other samples was normalized.

Chicken RBCs lysis assay: Chicken RBCs ($1\times10^7$ or $1\times10^8$ cells, Complement Technology Inc.) were incubated at 37° C. for 1 hour with 50% serum (Complement Technology Inc.) in GVB2+. Before addition to the chicken RBCs, sera from different animal species including human, dog, rabbit hamster, goat, pig, sheep, Rhesus monkey or Cynomolgus monkey, was pre-incubated with 50 µg/ml of 4E7, 9G6, 11C5, 2G1, 11D9, or 8E1 for 1 hour at 4° C. In some experiments, NHS was pre-incubated with serial diluted 2G1 or 8E1 for 1 hour at 4° C. Lysis reaction was stopped by addition of ice-cold 40 mM EDTA in PBS. The incubation mixtures were centrifuged for 5 min at 1500 rpm and the supernatant was collected and measured for $OD_{405}$ nm. The collected data were normalized against serum plus EDTA as negative control (0%) and against serum plus no antibody as positive control (100%).

PNH RBCs lysis assay: NHS were diluted with GVB2+ buffer and acidified to pH 6.4 (acidified normal human serum: aNHS) and used for assays with PNH RBCs. $5\times10^6$ cells were added in 50% aNHS. Incubated at 37° C., and after 30 min, reaction was stopped by adding 200 µl of cold 20 mM EDTA in PBS. mAb 2G1 were incubated with aNHS for 30 min in 4C before adding to the PNH RBCs. The RBCs were pelleted by centrifugation, and the optical density at 405 nm of an aliquot of the recovered supernatant was used to calculate the percentage lysis. PNH RBCs lysed in water used as 100% lysis standard.

Expression of Human C5 β Chain and Domain Deletion Mutants:

Human C5 (hC5) cDNA in pGEM-T vector was purchased from Sino Biologicals Inc. (Cat #HG13416-G). The C5 nucleotide sequence obtained from the Sino Biologicals Inc. was confirmed with gene and vector specific primers. hC5 β-chain nucleotide and protein sequence was identified with PubMed (NM_001735.2) and Uniprot Id-P01031. β-chain from hC5 was amplified and cloned into the pCAGGS vector. Macroglobulin (MG) domain deletion mutants (MG1, MG, MG3, MG4, MG5 and MG6) of β-chain were carried out in hC5-pGEM-T vector by inverse PCR and deletion was confirmed by sequencing. MG domain mutants of hC5 β chain were similarly cloned into the pCAGGS vector. Primers used for MG deletion mutants construction and cloning are listed in Table 1 below.

TABLE 1

Primers used for MG mutants construction and cloning

| SEQ ID NO: | Primer | Sequence (5'-3') |
|---|---|---|
| 90 | hC5β-MG1delReverse | TCCCCAGGTTTTCCCCAGGAAGAT |
| 91 | hC5β-MG1delForward | AATGGATTTCTCTTCATTCATAC |
| 92 | hC5β-MG2delReverse | GTCATAGGTTATTGGCATTCTT |
| 93 | hC5β-MG2delForward | TTGCCACATTTTTCTGTCTCAATC |
| 94 | hC5β-MG3delReverse | GACATATTCTTTAACTTCAAAATATG |
| 95 | hC5β-MG3delForward | CCCTACAAACTGAATTTGGTTG |
| 96 | hC5β-MG4delReverse | AGAGAGGACATATTTGATGCCAG |
| 97 | hC5β-MG4delForward | TCTCTCAGCCAAAGTTACCTT |
| 98 | hC5β-MG5delReverse | TGAGTATGCTATTGCTCGGTAAC |
| 99 | hC5β-MG5delForward | TGTGGCAACCAGCTCCAGGTTC |
| 100 | hC5β-MG6delReverse | TTTTTCTTCAATATTTAACCAG |
| 101 | hC5β-MG6delForward | AGGCCAAGAAGAACGCTGCAAAAG |
| 102 | hC5infF | TTTTGGCAAAGAATTCGCCACCATGGGCCTTTTGGGAATAC |
| 103 | hC5βinfR | CCTGAGGAGTGAATTCTTAATGGTGATGGTGGAGAATTTCTTTACAAGGTTC |

Transfection of hC5β and hC5β-MG Deletions:

The intact β chain and various MG domain deletion mutant cDNAs were transfected into HEK cells using Lipofectamine 2000 (Invitrogen). After 48 hours, supernatants were collected and used for assay.

SDS-PAGE and Western Blotting:

For Western blot analysis, 40 µl supernatant from hC5 β chain- and MG domain deletion mutant-transfected HEK cells or non-transfected HEK cell supernatant (negative control) was added to the tubes containing sample buffer and β-mercaptoethanol. Purified human C5 was used as a positive control. The samples were boiled at 100° C. for 7 min and loaded onto 4-12% gradient gel and proteins were transferred onto 0.2 µm pore size PVDF membrane. The membrane was blocked with 5% non-fat dry milk in TBS for 1 hour at room temperature. The membrane was then incubated with primary antibody (goat anti-hC5 polyclonal from Comptech, cat #A220 or biotinylated mAb 2G1-3 or QDC5) in 5% non-fat dry milk in TBST at 4° C. overnight. The membrane was washed with TBS with 0.1% Tween-20 (TBST) for 6×5 min and incubated with 1:4000 dilution of rabbit anti-goat-HRP (Bio-Rad, Cat #172-1034) for 1 hr at room temperature. Proteins were detected using Pierce™ ECL 2 Western Blotting substrate according to manufacturer's instructions. The mAb QDC5 is a recombinant human IgG4 mAb bearing VH and VL sequences of a humanized mouse anti-human C5 mAb as described in Thomas et al. (Mol Immunol., 1996 December; 33(17-18):1389-401). It was expressed in Expi-CHO cells (Invitrogen) and purified by protein A affinity chromatography.

Sandwich ELISA for Detection of hC5 β Chain and MG Deletion Mutants:

For Sandwich ELISA, 96-well plates were coated with 2G1-3 mAb at a final concentration of 2 µg/ml at 4° C. overnight. Following three washes with PBS containing 0.05% Tween-20, the plates were blocked with 3% bovine serum albumin (BSA) for 1 hour at room temperature. After washing, the plates were incubated with 200 µl of transfected HEK cell supernatants or 20% NHS for 1 h at room temperature. After another wash, the plates were incubated with the detection antibody SKY59 at a final concentration of 2 µg/ml at room temperature for 1 h, washed again and incubated with HRP-conjugated secondary human IgG4-specific antibody (Invitrogen #MA1-34437) at room temperature for 1 hr. The mAb SKY59 was expressed as an IgG4 recombinant mAb based on published VH/VL sequences (Fukuzawa et al., Sci Rep., 2017 Apr. 24; 7(1): 1080. doi: 10.1038/s41598-017-01087-7). In the case of Western blotting using a polyclonal goat anti-human C5 antibody, the antibody was used at 1:500 dilution at room temperature for 1 hr. After further washing, the wells were incubated with rabbit anti-goat IgG HRP (1:4000) for 1 hr. Plates were developed with HRP substrate for 6-10 min. The reaction was stopped with 2N H2SO4 and plate was read at 450 nm in a micro plate reader.

The results of this example are now described.

Results from an ELISA assay demonstrating the binding of anti-human C5 mAbs 4E7, 9G6, 11C5, 2G1, 11D9 and 8E1 to human C5 are shown in FIG. 1. Direct antigen binding ELISA in which mAbs are serially diluted across microtiter plates coated with purified human C5. All six mAbs showed high reactivity with human C5.

Results of experiments demonstrating binding affinities of anti-C5 mAbs 2G1, 8E1, 4E7, 9G6, 11C5 and 11D9 to C5 are shown in FIG. 2-7. Purified αmRabbit IgG (RAMFc) mAb was coupled onto a CM4 chip using the amine coupling method. Then, anti-C6 mAbs were captured on immobilized RAMFc. Biacore analyses were performed on a Biacore-2000 instrument.

Figure 8:
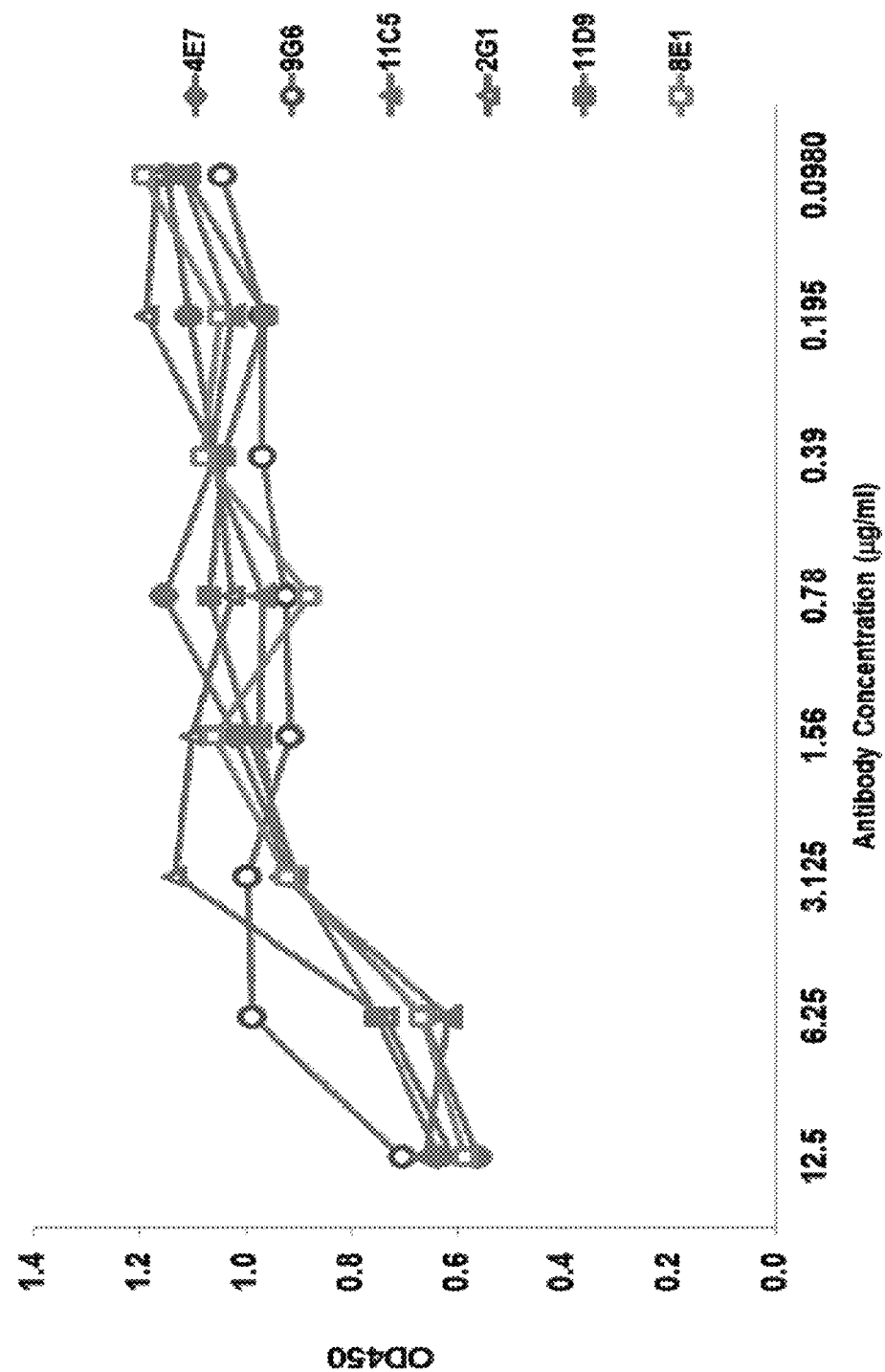
FIG. 8 depicts dose-dependent inhibition of LPS-induced C5a production by anti-human C5 mAbs 4E7, 9G6, 11C5, 2G1, 11D9 and 8E1. To assess the effect of anti-human C5 mAbs on LPS-induced C5a production, a combination of two assays was used: LPS-induced C5a production and human C5a sandwich ELISA. All six mAbs effectively inhibited LPS-induced C5a production when added to 10% normal human serum (NHS) at a final concentration of 12.5 µg/ml.

The dose-dependent inhibition of LPS-induced C5a production by anti-human C5 mAbs 4E7, 9G6, 11C5, 2G1, 11D9 and 8E1 is illustrated in FIG. 8. To assess the effect of anti-human C5 mAbs on LPS-induced C5a production, a combination of two assays was used: LPS-induced C5a production and human C5a sandwich ELISA. All six mAbs effectively inhibited LPS-induced C5a production when added to 10% normal human serum (NHS) at a final concentration of 12.5 μg/ml.

Figure 9:
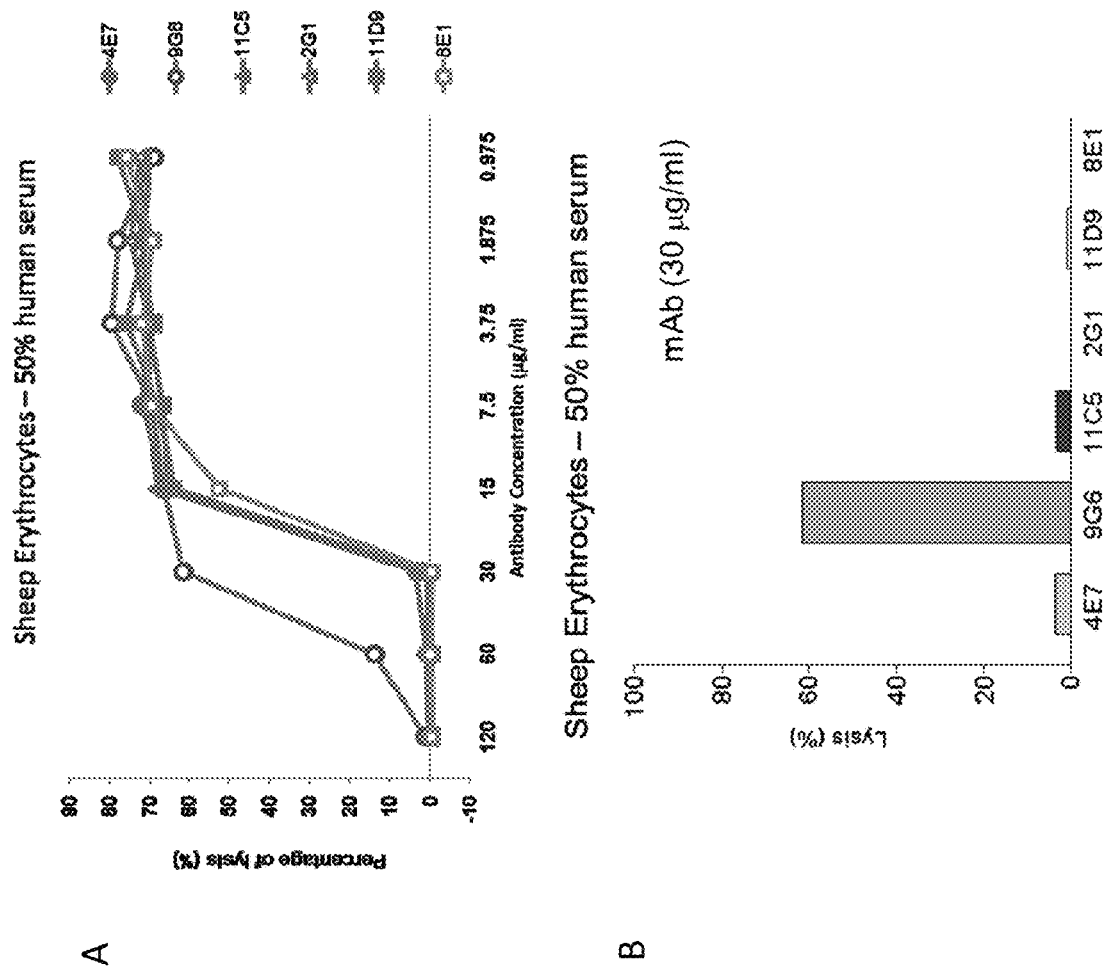
FIG. 9, comprising

The effects of anti-human C5 mAbs 4E7, 9G6, 11C5, 2G1, 11D9 and 8E1 on complement-mediated hemolysis are shown in FIG. 9. FIG. 9A illustrates RBC lysis determined by measuring the absorbance at OD405 nm after sheep RBCs were incubated with 50% NHS containing serial dilutions of each anti-C5 mAb at 37° C. for 1 hour. RBC lysis was determined by measuring the absorbance at OD405 nm. At 120 μg/ml, all mAbs inhibited 50% NHS-mediated sheep erythrocyte lysis. At lower doses (e.g., 30-60 μg/ml), 9G6 was less potent in preventing hemolysis than other mAbs. FIG. 9B illustrates that at 30 μg/ml, mAb 2G1 and 8E1 were more potent at inhibiting complement-mediated hemolysis than 4E7, 11C5 and 11D9.

Figure 10:
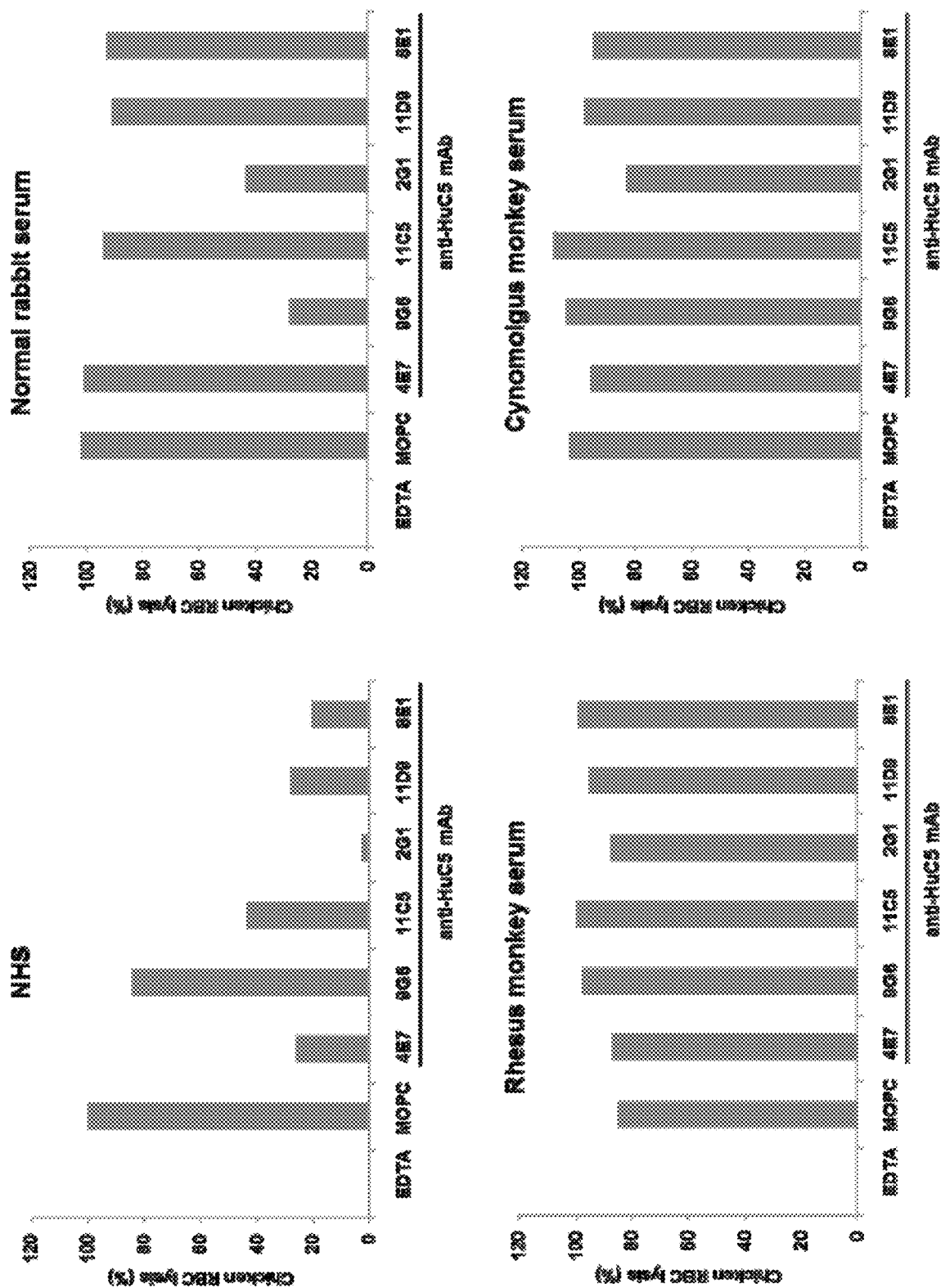
FIG. 10 depicts the results of experiments assessing the effects of anti-human C5 mAbs 4E7, 9G6, 11C5, 2G1, 11D9, 8E1 on complement-mediated hemolysis using sera from different animal species. Antibody-sensitized chicken RBCs were incubated with 50% NHS, normal rabbit serum, Rhesus monkey serum or Cynomolgus monkey serum containing each anti-C5 mAb (final concentration: 50 µg/ml) at 37° C. for 1 hour. RBC lysis was determined by measuring the absorbance at OD405 nm, and normalized against serum plus EDTA as negative control (0%), and against serum plus no antibody as positive control (100%). In the hemolytic assay using NHS, five of six anti-human C5 mAbs inhibited hemolysis significantly, i.e. by more than 50%. Especially, NHS samples containing 2G1 showed almost complete inhibition of hemolysis. When treated with mAb 9G6 or 2G1, hemolytic activity in rabbit serum was significantly reduced. On the other hand, all mAbs did not significantly inhibit complement-mediated hemolysis using monkey (Rhesus and Cynomolgus) sera.

The effects of anti-human C5 mAbs 4E7, 9G6, 11C5, 2G1, 11D9, 8E1 on complement-mediated hemolysis using sera from different animal species are shown in FIG. 10. Chicken RBCs were incubated with 50% NHS, normal rabbit serum, Rhesus monkey serum or Cynomolgus monkey serum containing each anti-C5 mAb (final 50 μg/ml) at 37° C. for 1 hour. RBC lysis was determined by measuring the absorbance at OD405 nm, and normalized against serum plus EDTA as negative control (0%), and against serum plus no antibody as positive control (100%). In the hemolytic assay using NHS, five of six anti-human C5 mAbs inhibited hemolysis significantly, i.e. by more than 50%. Especially, NHS samples containing 2G1 showed almost complete inhibition of hemolysis. When treated with mAb 9G6 or 2G1, hemolytic activity in rabbit serum was significant reduced. On the other hand, all mAbs failed to inhibit complement-mediated hemolysis using sera of monkey (Rhesus and Cynomolgus), goat, pig and sheep.

Figure 11:
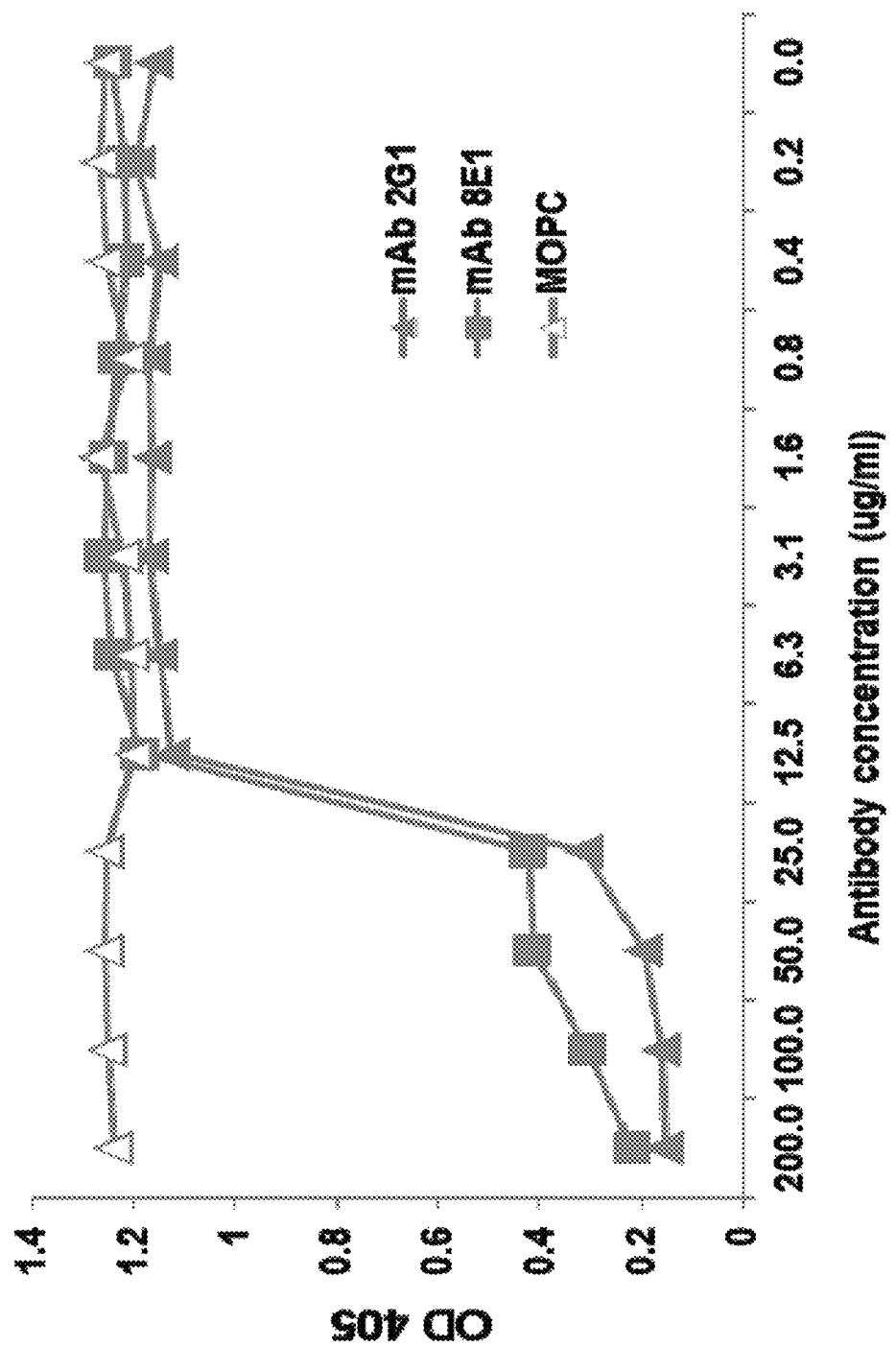
FIG. 11 depicts the results of an experiment assessing the effects of anti-human C5 mAbs 2G1 and 8E1 on complement-mediated hemolysis. Antibody-sensitized chicken RBCs were incubated with 50% NHS containing serial dilutions of 2G1 or 8E1 or control mAb (MOPC, mouse IgG1) at 37° C. for 1 hr. RBC lysis was determined by measuring the absorbance at OD405 nm. mAb 2G1 and 8E1 had similar activities in this assay.

The effects of anti-human C5 mAbs 2G1 and 8E1 on complement-mediated hemolysis are depicted in FIG. 11. Chicken RBCs were incubated with 50% NHS containing serial dilutions of 2G1 or 8E1 or control mAb (MOPC, mouse IgG1) at 37° C. for 1 hour. RBC lysis was determined by measuring the absorbance at OD405 nm.

Figure 12:
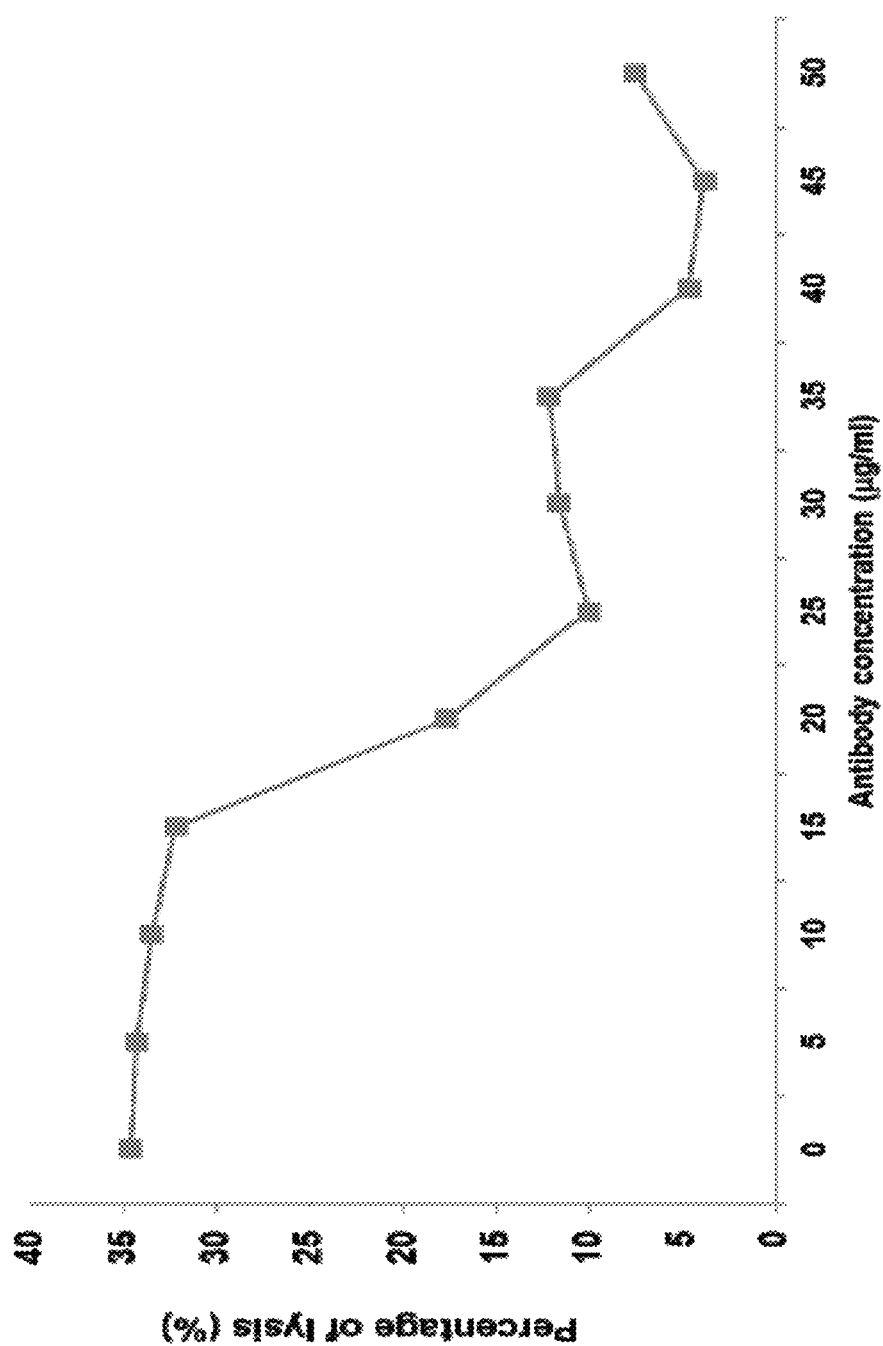
FIG. 12 depicts the results of experiments assessing the effect of anti-human C5 mAb 2G1 on hemolysis of PNH RBCs. RBCs from paroxysmal nocturnal hemoglobinuria (PNH) patients were subjected to Ham's acidified serum test in the presence or absence of mAb 2G1. RBCs were incubated with 50% NHS containing serial dilutions of 2G1 at 37° C. for 1 hour. RBC lysis was determined by measuring the absorbance at $OD_{405}$ nm. In the absence of mAb, about 35% of RBCs were lysed by acidified serum, while mAb 2G1 treatment caused 70% reduction of hemolytic activity at 25 µg/ml and 85% reduction at 40 µg/ml.

The effect of anti-human C5 mAb 2G1 on hemolysis of PNH RBCs is presented in FIG. 12. RBCs from paroxysmal nocturnal hemoglobinuria (PNH) patients were subjected to Ham's acidified serum test in the presence or absence of mAb 2G1. RBCs were incubated with 50% NHS containing serial dilutions of 2G1 at 37° C. for 1 hour. RBC lysis was determined by measuring the absorbance at OD405 nm. In the absence of mAb, about 35% of RBCs were lysed by acidified serum, while mAb 2G1 treatment caused 70% reduction of hemolytic activity at 25 μg/ml and 85% reduction at 40 μg/ml.

Antibody sequences for the six antibodies are shown in FIG. 13 through FIG. 18. FIG. 13 depicts the variable region sequences of heavy and light chains of mAb 2G1. FIG. 14 depicts the variable region sequences of heavy and light chains of mAb 8E1. FIG. 15 depicts the variable region sequences of heavy and light chains of mAb 4E7. FIG. 16 depicts the variable region sequences of heavy and light chains of mAb 9G6. FIG. 17 depicts the variable region sequences of heavy and light chains of mAb 11C5. FIG. 18 depicts the variable region sequences of heavy and light chains of mAb 11D9.

The amino acid sequences of human IgG4 constant heavy region, with a serine 228 to proline mutation (i.e., S228P) and human kappa constant light region are shown in FIG. 19. These sequences were used to construct chimeric (mouse variable region+human constant region) and humanized (humanized mouse variable region+human constant region) anti-human C5 antibody (2G1).

Figure 20:
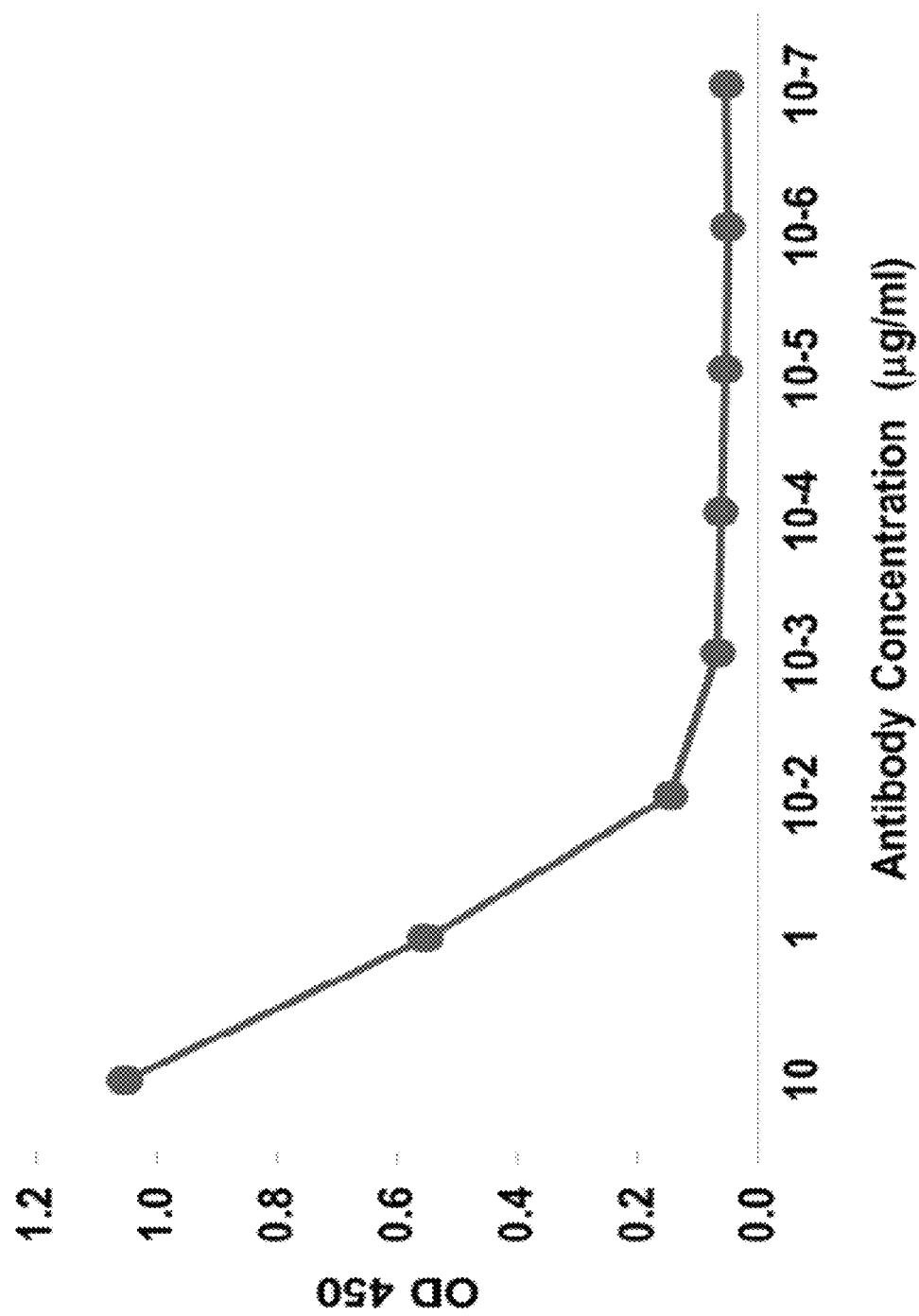
FIG. 20 depicts results from experiments evaluating the reactivity of 2G1 human IgG4 chimeric mAb with human C5. Chimeric 2G1 was made by joining the variable regions of mAb 2G1 with human IgG4 heavy chain constant region carrying a S228P mutation and human kappa light chain constant region. A plate was coated with human C5. After incubation with serially diluted chimeric 2G1 mAb, bound chimeric mAb was detected by HRP-conjugated anti-human IgG4. Chimeric 2G1 bound to human C5 in a dose-dependent manner.

The reactivity of 2G1 human IgG4 chimeric mAb with human C5 is shown in FIG. 20. Chimeric 2G1 was made by joining the variable regions of mAb 2G1 with human IgG4 heavy chain constant region carrying a S228P mutation and human kappa light chain constant region. A plate was coated with human C5. After incubation with serially diluted chimeric 2G1, bound chimeric mAb was detected by HRP-conjugated anti-human IgG4. Chimeric 2G1 bound to human C5 in a dose dependent manner.

Figure 21:
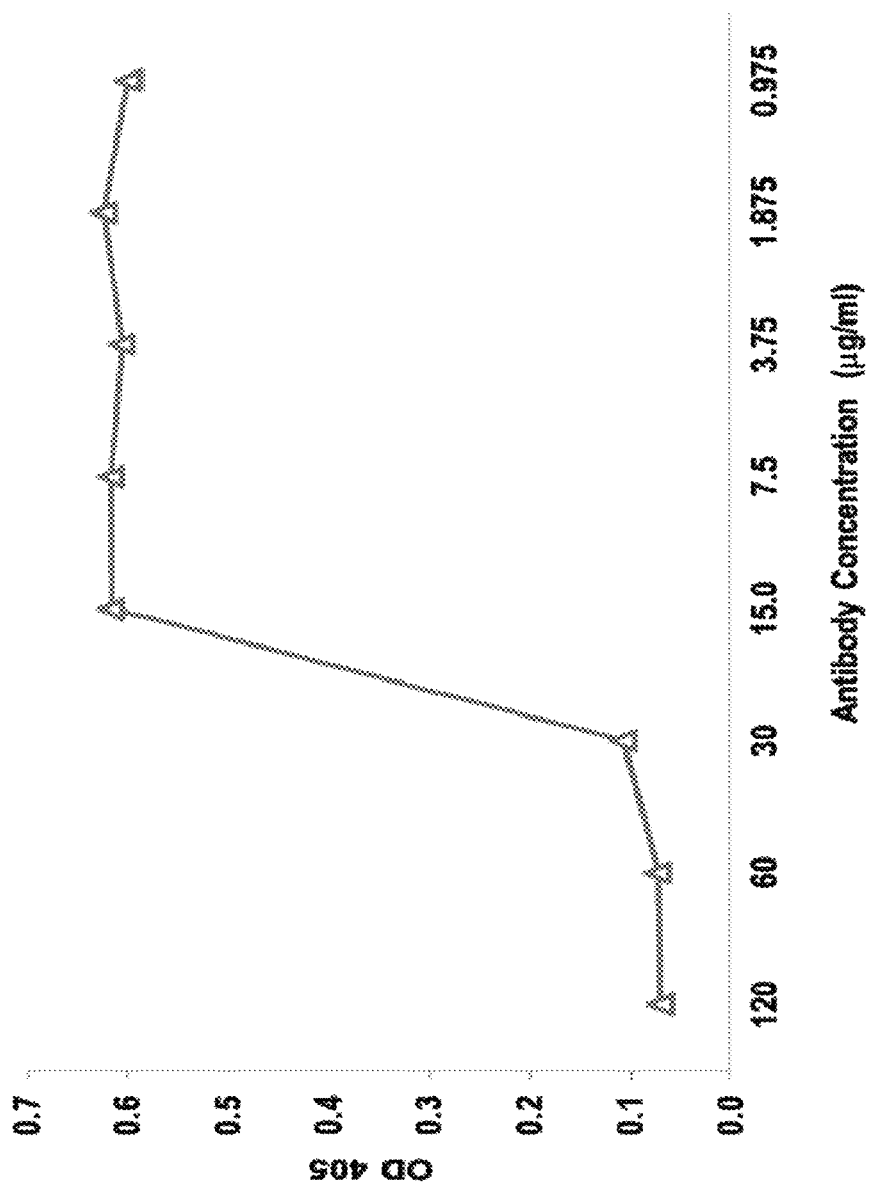
FIG. 21 depicts results from experiments evaluating the effects of human IgG4-2G1 chimeric mAb on classical pathway complement-mediated hemolysis. Sensitized sheep RBCs were incubated with 50% NHS containing serially diluted chimeric 2G1 at 37° C. for 1 hour. RBC lysis was determined by measuring the absorbance at $OD_{405}$ nm. The result shows that at 30 µg/ml and higher concentrations, chimeric 2G1 mAb effectively inhibited NHS-mediated sheep erythrocyte lysis.

The effects of 2G1 human IgG4 chimeric mAb on classical pathway complement-mediated hemolysis is shown in FIG. 21. Sensitized sheep RBCs were incubated with NHS containing serially diluted chimeric 2G1 at 37° C. for 1 hour. RBC lysis was determined by measuring the absorbance at OD405 nm. The result shows that at 30 μg/ml and higher concentrations, chimeric 2G1 mAb inhibited 50% of NHS-mediated sheep erythrocyte lysis.

The nucleotide and amino acid sequences of a humanized variable heavy chain (VH) of mAb 2G1 (humanized 2G1 VH-11801) are illustrated in FIG. 22. Humanization was achieved by CDR grating from murine mAb 2G1 VH into a germline encoded human VH frame (11801). The amino acid sequence of signal peptide is underlined and that of CDR1, CDR2 and CDR3 is bolded and shaded.

The nucleotide and amino acid sequences of another humanized VH of mAb 2G1 (humanized 2G1 VH-16901) are illustrated in FIG. 23. Humanization was achieved by CDR grating from murine mAb 2G1 VH into a germline encoded human VH frame (16901). The amino acid sequence of signal peptide is underlined and that of CDR1, CDR2 and CDR3 is bolded shaded.

The nucleotide and amino acid sequences of a humanized variable light chain (VL) of mAb 2G1 (humanized 2G1 VL-1901) are illustrated in FIG. 24. Humanization was achieved by CDR grating from murine mAb 2G1 VL into a germline encoded human VL frame (1901). The amino acid sequence of signal peptide is underlined and that of CDR1, CDR2 and CDR3 is bolded and shaded.

Figure 25:
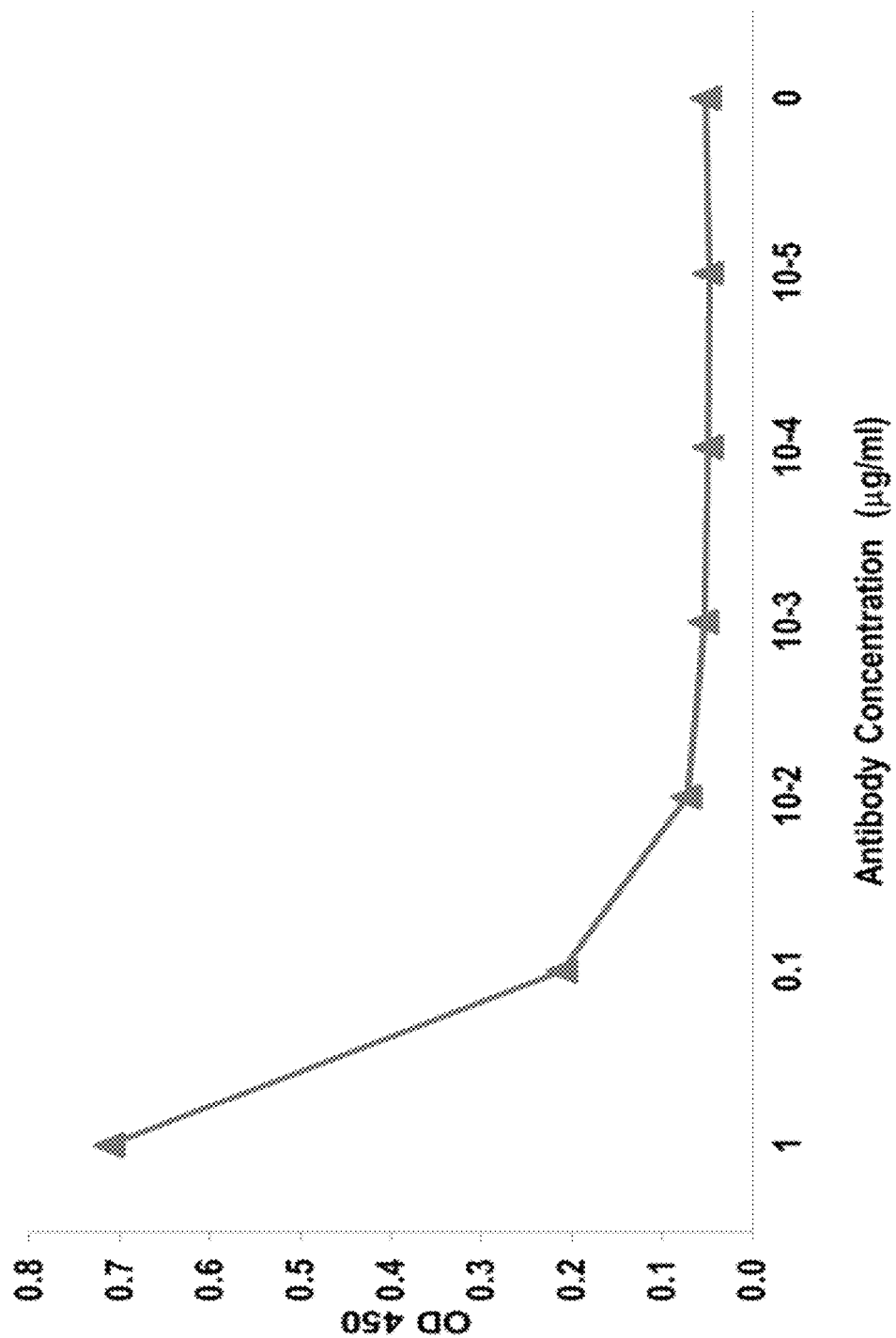
FIG. 25 depicts results from experiments evaluating the reactivity of humanized 2G1 (VH-11801/VL-1901) with human C5. Humanized 2G1 (VH-11801/VL-1901) was expressed as a human IgG4 mAb with S228P mutation in the Fc domain. A plate was coated with human C5. After incubation with serially diluted humanized 2G1 (VH-11801/VL-1901), bound mAb was detected by HRP-conjugated anti-human IgG4. Humanized 2G1 (VH-11801/VL-1901) bound human C5 in a dose-dependent manner.

The reactivity of humanized 2G1 (VH-11801/VL-1901) with human C5 is shown in FIG. 25. Humanized 2G1 (VH-11801/VL-1901) was expressed as a human IgG4 mAb with S228P mutation in the Fc domain. A plate was coated with human C5. After incubation with serially diluted humanized 2G1 (VH-11801/VL-1901), bound mAb was detected by HRP-conjugated anti-human IgG4. Humanized 2G1 (VH-11801/VL-1901) bound human C5 in a dose dependent manner.

Figure 26:
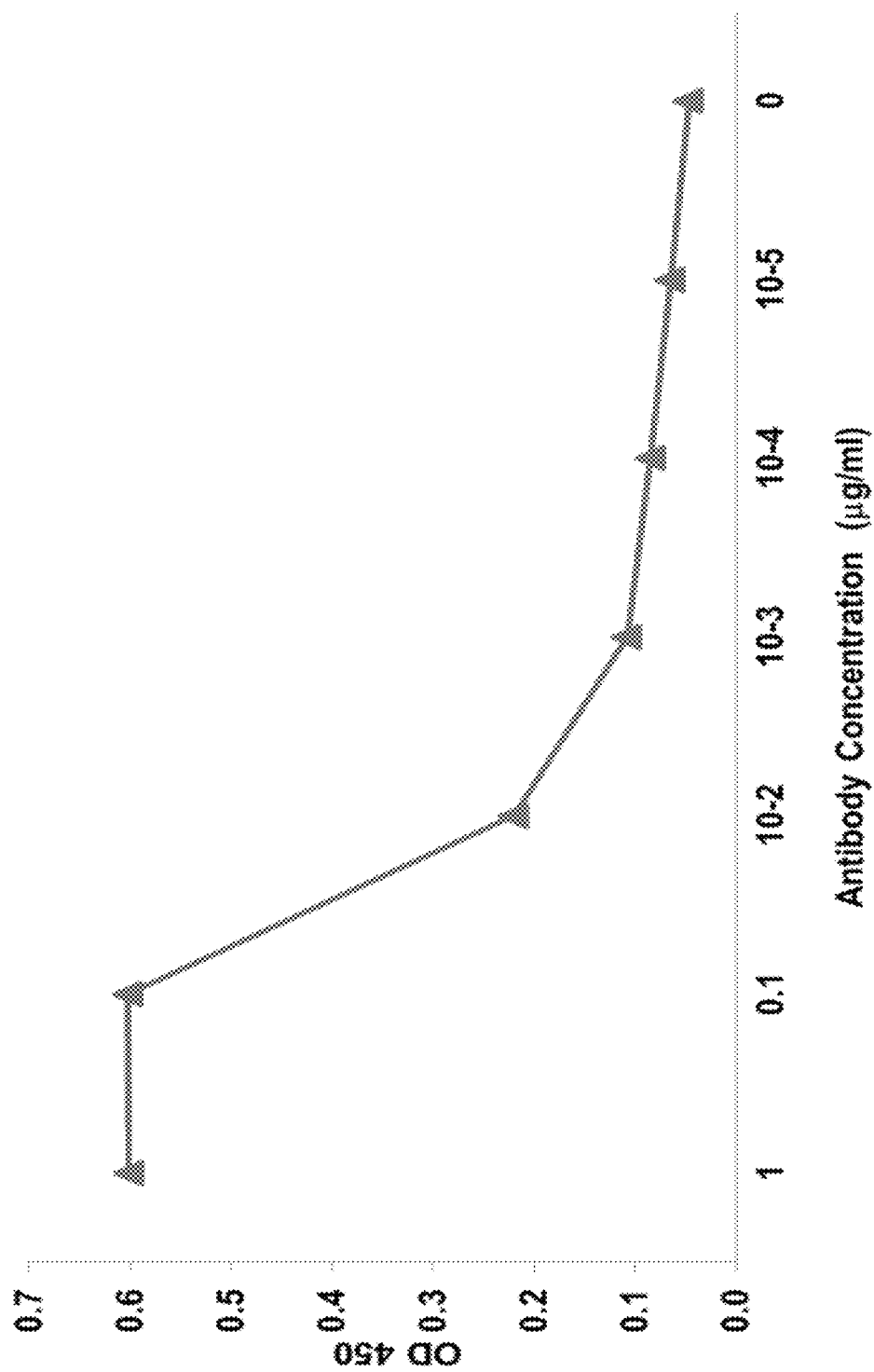
FIG. 26 depicts results from experiments evaluating the reactivity of humanized 2G1 (VH-16901/VL-1901) with human C5. Humanized 2G1 (VH-16901/VL-1901) was expressed as a human IgG4 mAb with S228P mutation in the Fc domain. A plate was coated with human C5. After incubation with serially diluted humanized 2G1 (VH-16901/VL-1901), bound Ab was detected by HRP-conjugated anti-human IgG4. Humanized 2G1 (VH-16901/VL-1901) bound human C5 in a dose-dependent manner.

The reactivity of humanized 2G1 (VH-16901/VL-1901) with human C5 is shown in FIG. 26. Humanized 2G1 (VH-16901/VL-1901) was expressed as a human IgG4 mAb with S228P mutation in the Fc domain. A plate was coated with human C5. After incubation with serially diluted humanized 2G1 (VH-16901/VL-1901), bound Ab was detected by HRP-conjugated anti-human IgG4. Humanized 2G1 (VH-16901/VL-1901) bound human C5 in a dose dependent manner.

Figure 27:
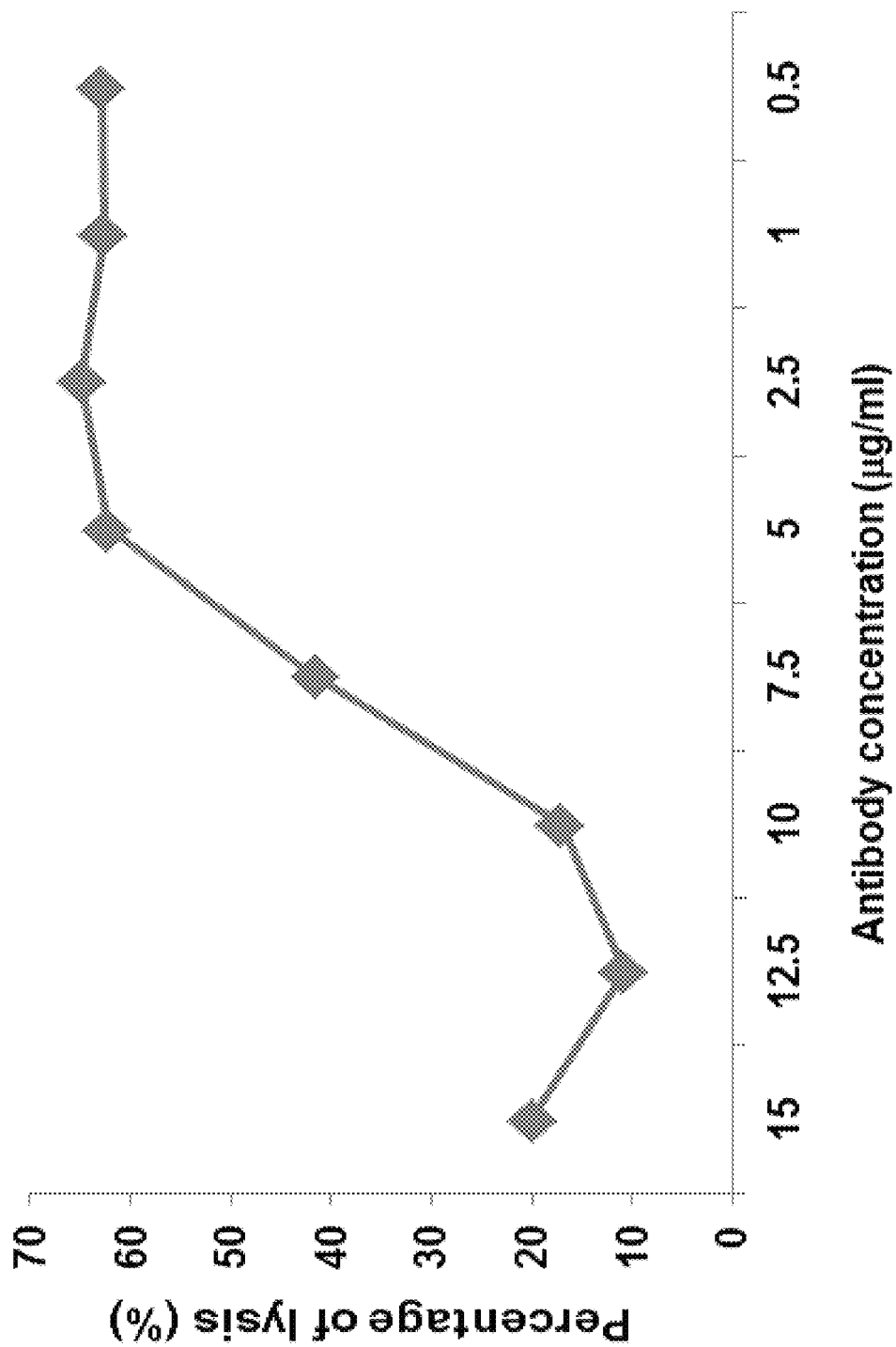
FIG. 27 depicts results from experiments evaluating the effects of the humanized 2G1 (VH-11801/VL-1901) on classical pathway complement-mediated hemolysis. Humanized 2G1 (VH-11801/VL-1901) was expressed as a human IgG4 mAb with S228P mutation in the Fc domain. Antibody-sensitized sheep RBCs were incubated with 10% NHS containing serially diluted humanized 2G1 (VH-11801/VL-1901) at 37° C. for 1 hour. RBC lysis was determined by measuring the absorbance at $OD_{405}$ nm. Humanized 2G1 (VH-11801/VL-1901) significantly inhibited 10% NHS-mediated sheep erythrocyte lysis at 10 µg/ml and higher mAb concentrations.

The effects of the humanized 2G1 (VH-11801/VL-1901) on classical pathway complement-mediated hemolysis is shown in FIG. 27. Humanized 2G1 (VH-11801/VL-1901) was expressed as a human IgG4 mAb with S228P mutation in the Fc domain. Sensitized sheep RBCs were incubated with 10% NHS containing serially diluted humanized 2G1 (VH-11801/VL-1901) at 37° C. for 1 hour. RBC lysis was determined by measuring the absorbance at OD405 nm. Humanized 2G1 (VH-11801/VL-1901) significantly inhibited 10% NHS-mediated sheep erythrocyte lysis at 10 μg/ml and higher mAb concentrations.

Figure 28:
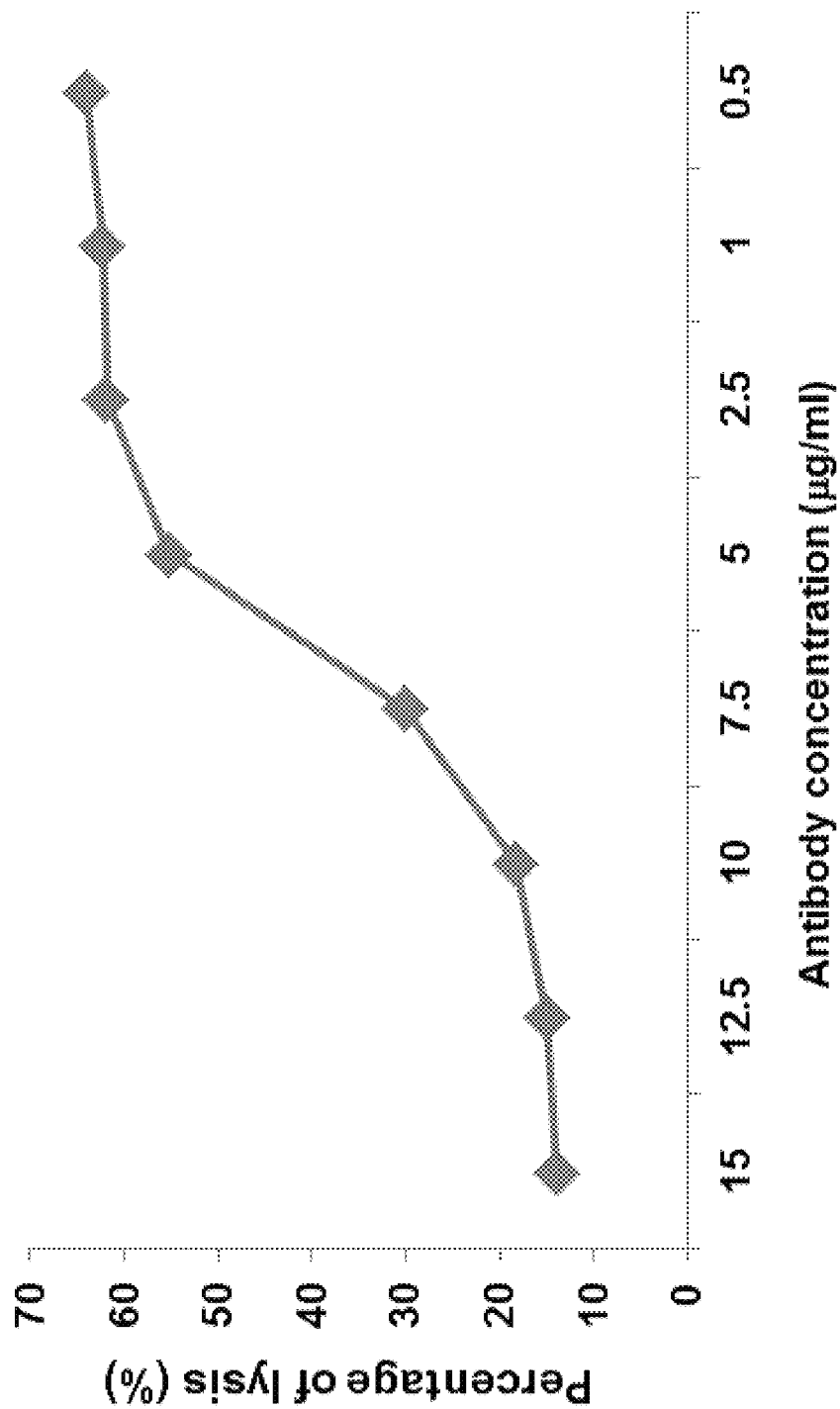
FIG. 28 depicts results from experiments evaluating the effects of the humanized 2G1 (VH-16901/VL-1901) on classical pathway complement-mediated hemolysis. Humanized 2G1 (VH-16901/VL-1901) was expressed as a human IgG4 mAb with S228P mutation in the Fc domain. Antibody-sensitized sheep RBCs were incubated with 10% NHS containing serially diluted humanized 2G1 (VH- 16901/VL-1901) at 37° C. for 1 hour. RBC lysis was determined by measuring the absorbance at $OD_{405}$ nm. Humanized 2G1 (VH-16901/VL-1901) significantly inhibited 10% NHS-mediated sheep erythrocyte lysis at 10 μg/ml and higher mAb concentrations.
Figure 29:
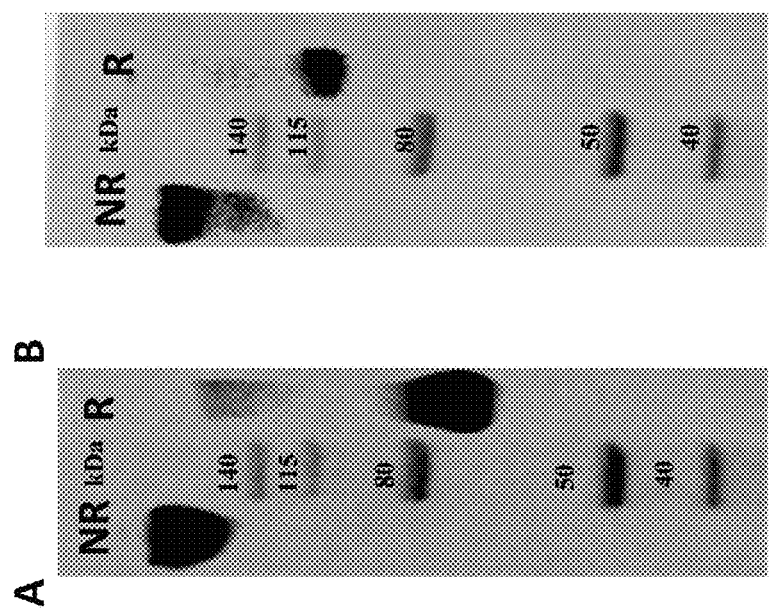
FIG. 29, comprising
Figure 31:
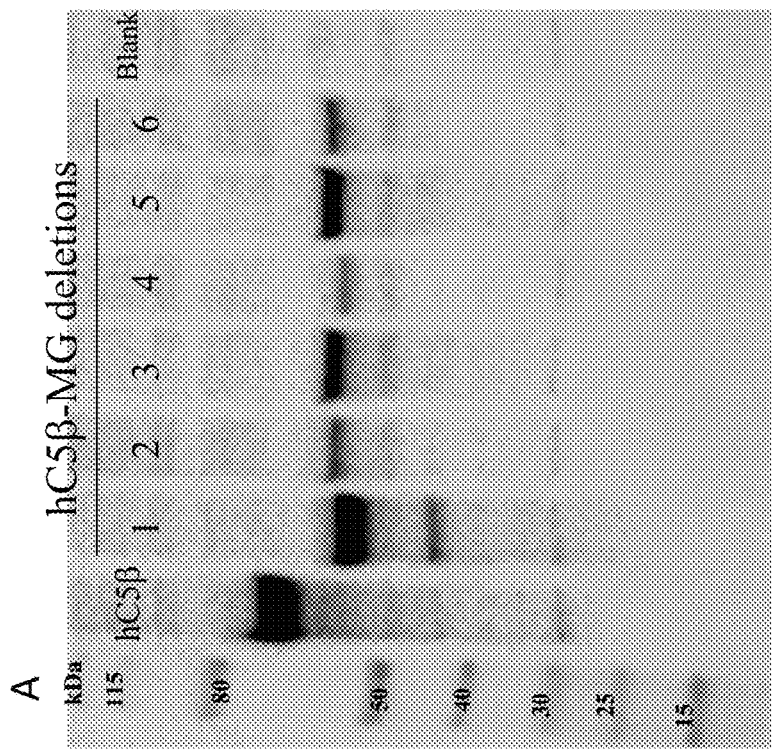
FIG. 31, comprising
Figure 32:
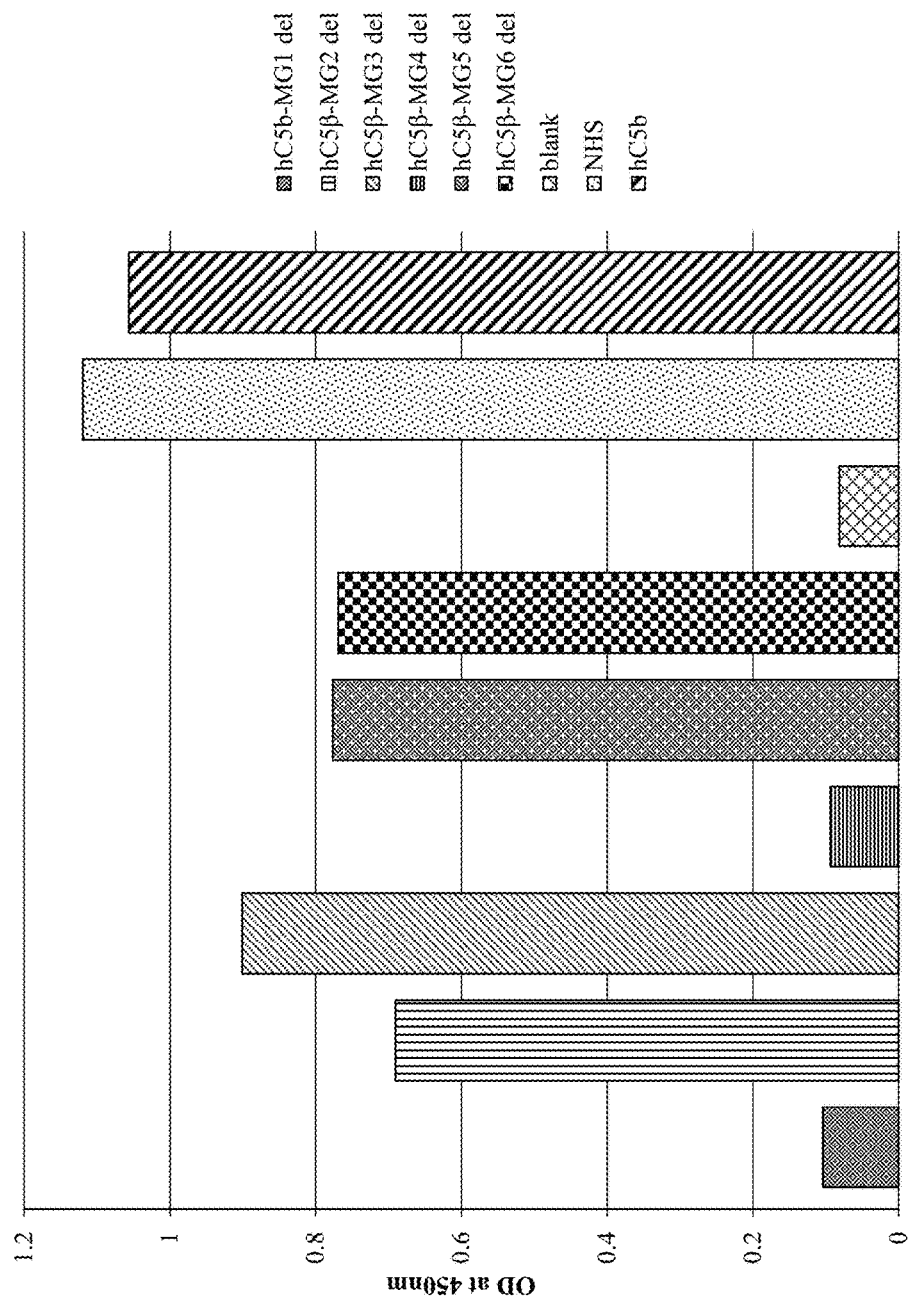
FIG. 32 depicts the results of a Sandwich ELISA assay to assess the critical MG domains with human C5 β chain for mAb 2G1-3 binding. mAb 2G1-3 was coated onto 96 well plate and supernatants from non-transfected or transfected HEK cells were added. After incubation and washing, the bound β chain or deletion mutant proteins were detected by a second anti-human C5 mAb SKY59 (Fukuzawa et al., Sci Rep. 2017 Apr. 24; 7(1):1080. doi: 10.1038/s41598-017-01087-7) which is known to bind sequences within the MG1 domain of human C5. The data demonstrated that signals for MG2, MG3, MG5 and MG6 deletion mutants were still detected, suggesting these domains were not involved in the binding of either 2G1-3 or SKY59. On the other hand, MG1 and MG4 deletion mutants lost binding, suggesting they are critical for human C5 binding by either 2G1-3 or SKY59 or both. Normal human serum (NHS) and intact β chain transfected cell supernatant were used as positive controls and non-transfected HEK cell supernatant (blank) was used as a negative control.
Figure 33:
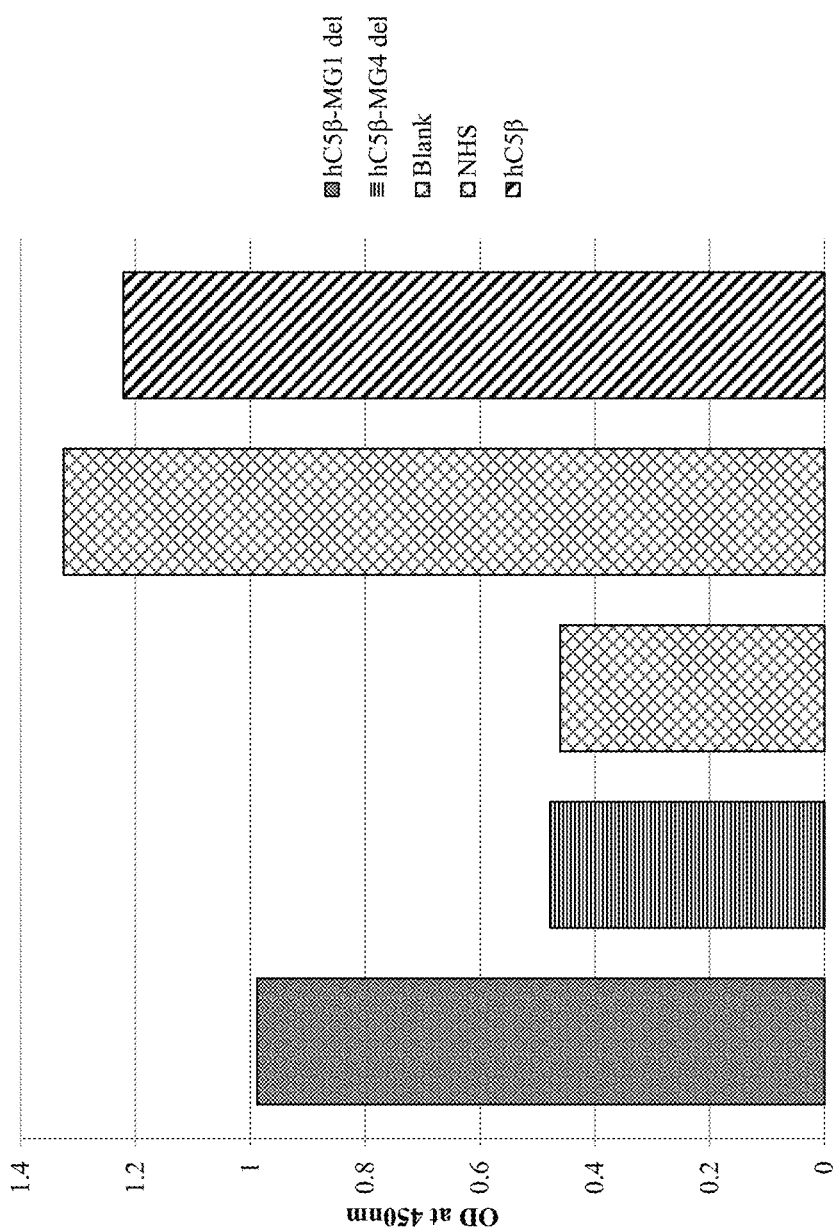

The effects of the humanized 2G1 (VH-16901/VL-1901) on classical pathway complement-mediated hemolysis are shown in FIG. 28. Humanized 2G1 (VH-16901/VL-1901) was expressed as a human IgG4 mAb with S228P mutation in the Fc domain. Sensitized sheep RBCs were incubated with 10% NHS containing serially diluted humanized 2G1 (VH-16901/VL-1901) at 37° C. for 1 hour. RBC lysis was determined by measuring the absorbance at OD405 nm. Humanized 2G1 (VH-16901/VL-1901) significantly inhibited 10% NHS-mediated sheep erythrocyte lysis at 10 μg/ml and higher mAb concentrations.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antibody that specifically binds to human C5, wherein the antibody comprises at least one antibody selected from the group consisting of:
a) an antibody comprising a heavy chain variable (VH) region and a light chain variable (VL) region, wherein the VH region comprises
 i) a VH-CDR1 comprising the amino acid sequence of SEQ ID NO: 3;
 ii) a VH-CDR2 comprising the amino acid sequence of SEQ ID NO: 4; and
 iii) a VH-CDR3 comprising the amino acid sequence of SEQ ID NO: 5; and
wherein the VL region comprises
 i) a VL-CDR1 comprising the amino acid sequence of SEQ ID NO: 8;
 ii) a VL-CDR2 comprising the amino acid sequence of SEQ ID NO: 9; and
 iii) a VL-CDR3 comprising the amino acid sequence of SEQ ID NO: 10;
b) an antibody comprising a heavy chain variable (VH) region and a light chain variable (VL) region, wherein the VH region comprises
 i) a VH-CDR1 comprising the amino acid sequence of SEQ ID NO: 13;
 ii) a VH-CDR2 comprising the amino acid sequence of SEQ ID NO: 14; and
 iii) a VH-CDR3 comprising the amino acid sequence of SEQ ID NO: 15; and
wherein the VL region comprises
 i) a VL-CDR1 comprising the amino acid sequence of SEQ ID NO: 18;
 ii) a VL-CDR2 comprising the amino acid sequence of SEQ ID NO: 19; and
 iii) a VL-CDR3 comprising the amino acid sequence of SEQ ID NO: 20;
c) an antibody comprising a heavy chain comprising the amino acid sequence of SEQ ID NO:22 and a light chain comprising the amino acid sequence of SEQ ID NO:27;
d) an antibody comprising a heavy chain variable (VH) region and a light chain variable (VL) region, wherein the VH region comprises
 i) a VH-CDR1 comprising the amino acid sequence of SEQ ID NO: 32;
 ii) a VH-CDR2 comprising the amino acid sequence of SEQ ID NO: 33; and
 iii) a VH-CDR3 comprising the amino acid sequence of SEQ ID NO: 34; and
wherein the VL region comprises
 i) a VL-CDR1 comprising the amino acid sequence of SEQ ID NO: 37;
 ii) a VL-CDR2 comprising the amino acid sequence of SEQ ID NO: 38; and
 iii) a VL-CDR3 comprising the amino acid sequence of SEQ ID NO: 39;
e) an antibody comprising a heavy chain variable (VH) region and a light chain variable (VL) region, wherein the VH region comprises
 i) a VH-CDR1 comprising the amino acid sequence of SEQ ID NO: 42;
 ii) a VH-CDR2 comprising the amino acid sequence of SEQ ID NO: 43; and
 iii) a VH-CDR3 comprising the amino acid sequence of SEQ ID NO: 44; and
wherein the VL region comprises
 i) a VL-CDR1 comprising the amino acid sequence of SEQ ID NO: 47;
 ii) a VL-CDR2 comprising the amino acid sequence of SEQ ID NO: 48; and
 iii) a VL-CDR3 comprising the amino acid sequence of SEQ ID NO: 49; and
f) an antibody comprising a heavy chain variable (VH) region and a light chain variable (VL) region, wherein the VH region comprises
 i) a VH-CDR1 comprising the amino acid sequence of SEQ ID NO: 52;
 ii) a VH-CDR2 comprising the amino acid sequence of SEQ ID NO: 53; and
 iii) a VH-CDR3 comprising the amino acid sequence of SEQ ID NO: 54; and
wherein the VL region comprises
 i) a VL-CDR1 comprising the amino acid sequence of SEQ ID NO: 57;
 ii) a VL-CDR2 comprising the amino acid sequence of SEQ ID NO: 58; and
 iii) a VL-CDR3 comprising the amino acid sequence of SEQ ID NO: 59.

2. The antibody of claim 1, wherein the antibody is a chimeric antibody.

3. The antibody of claim 1, wherein the antibody comprises the CDRs: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10.

4. The antibody of claim 1, wherein the antibody comprises a heavy chain comprising an amino acid sequence selected from the group consisting of: an amino acid sequence having at least 95% identity to SEQ ID NO:2, amino acid sequence having at least 95% identity to SEQ ID NO: 12, amino acid sequence of SEQ ID NO: 22, amino acid sequence having at least 95% identity to SEQ ID NO: 31, amino acid sequence having at least 95% identity to SEQ ID NO: 41, and amino acid sequence having at least 95% identity to SEQ ID NO: 51.

5. The antibody of claim 1, wherein the antibody comprises a light chain comprising an amino acid sequence selected from the group consisting of: an amino acid sequence having at least 95% identity to SEQ ID NO:7, amino acid sequence having at least 95% identity to SEQ ID NO: 17, amino acid sequence of SEQ ID NO: 27, amino acid sequence having at least 95% identity to SEQ ID NO: 36, amino acid sequence having at least 95% identity to SEQ ID NO: 46, and amino acid sequence having at least 95% identity to SEQ ID NO: 56.

6. The antibody of claim 1, wherein the antibody comprises a combination of a heavy chain and a light chain selected from the group consisting of:
   (a) a heavy chain comprising an amino acid sequence having at least 95% identity to SEQ ID NO:2 and a light chain comprising an amino acid sequence having at least 95% identity to SEQ ID NO:7;
   (b) a heavy chain comprising an amino acid sequence having at least 95% identity to SEQ ID NO:12 and a light chain comprising an amino acid sequence having at least 95% identity to SEQ ID NO:17;
   (c) a heavy chain comprising the amino acid sequence of SEQ ID NO:22 and a light chain comprising the amino acid sequence of SEQ ID NO:27;
   (d) a heavy chain comprising an amino acid sequence having at least 95% identity to SEQ ID NO:31 and a light chain comprising an amino acid sequence having at least 95% identity to SEQ ID NO:36;
   (e) a heavy chain comprising an amino acid sequence having at least 95% identity to SEQ ID NO:41 and a light chain comprising an amino acid sequence having at least 95% identity to SEQ ID NO:46; and
   (f) a heavy chain comprising an amino acid sequence having at least 95% identity to SEQ ID NO:51 and a light chain comprising an amino acid sequence having at least 95% identity to SEQ ID NO:56.

7. The antibody of claim 1, wherein the antibody comprises the CDRs: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO:19; and VL-CDR3: SEQ ID NO:20.

8. The antibody of claim 1, wherein the antibody comprises the CDRs: VH-CDR1: SEQ ID NO:32; VH-CDR2: SEQ ID NO:33; VH-CDR3: SEQ ID NO:34; VL-CDR1: SEQ ID NO:37; VL-CDR2: SEQ ID NO:38, and VL-CDR3: SEQ ID NO:39.

9. The antibody of claim 1, wherein the antibody comprises the CDRs: VH-CDR1: SEQ ID NO:42; VH-CDR2: SEQ ID NO:43; VH-CDR3: SEQ ID NO:44; VL-CDR1: SEQ ID NO:47; VL-CDR2: SEQ ID NO:48, and VL-CDR3: SEQ ID NO:49.

10. The antibody of claim 1, wherein the antibody comprises the CDRs: VH-CDR1: SEQ ID NO:52; VH-CDR2: SEQ ID NO:53; VH-CDR3: SEQ ID NO:54; VL-CDR1: SEQ ID NO:57; VL-CDR2: SEQ ID NO:58, and VL-CDR3: SEQ ID NO:59.

11. A method of treating a complement pathway-mediated disease or disorder in an individual, comprising the step of administering to said individual the anti-C5 antibody of claim 1.

12. The method of claim 11, wherein the disease or disorder is at least one selected from the group consisting of: macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, organ transplantation, inflammation, inflammation associated with cardiopulmonary bypass surgery and kidney dialysis, C3 glomerulopathy, membranous nephropathy, IgA nephropathy, glomerulonephritis, anti-neutrophil cytoplasmic antibody (ANCA)-mediated glomerulonephritis, lupus nephritis, ANCA-mediated vasculitis, Shiga toxin induced HUS, antiphospholipid antibody-induced pregnancy loss, and any combinations thereof.

13. A method of reducing the activity of a complement system of an individual, wherein the method comprises administering an antibody to the individual via a route of administration selected from the group consisting of enteral administration, parenteral administration, and a combination thereof, and wherein the antibody is the antibody of claim 1.

14. The method of claim 13, wherein the antibody is an antibody fragment selected from the group consisting of a Fab, Fab', F(ab)2, F(ab')2, scFv, and combinations thereof.

15. A cell comprising the antibody of claim 1.

16. The cell of claim 15, wherein the cell produces the antibody of claim 1.

17. The cell of claim 15, wherein the cell is a hybridoma.

18. The antibody of claim 3, wherein the antibody comprises a heavy chain comprising the amino acid sequence having at least 95% identity to SEQ ID NO:2 and a light chain comprising the amino acid sequence having at least 95% identity to SEQ ID NO:7.

19. The antibody of claim 7, wherein the antibody comprises a heavy chain comprising the amino acid sequence having at least 95% identity to SEQ ID NO:12 and a light chain comprising the amino acid sequence having at least 95% identity to SEQ ID NO:17.

20. The antibody of claim 1, wherein the antibody comprises a heavy chain comprising the amino acid sequence of SEQ ID NO:22 and a light chain comprising the amino acid sequence of SEQ ID NO:27.

21. The antibody of claim 8, wherein the antibody comprises a heavy chain comprising the amino acid sequence having at least 95% identity to SEQ ID NO:31 and a light chain comprising the amino acid sequence having at least 95% identity to SEQ ID NO:36.

22. The antibody of claim 9, wherein the antibody comprises a heavy chain comprising the amino acid sequence having at least 95% identity to SEQ ID NO:41 and a light chain comprising the amino acid sequence having at least 95% identity to SEQ ID NO:46.

23. The antibody of claim 10, wherein the antibody comprises a heavy chain comprising the amino acid sequence having at least 95% identity to SEQ ID NO:51 and a light chain comprising the amino acid sequence having at least 95% identity to SEQ ID NO:56.

\* \* \* \* \*

```
                        SEQUENCE LISTING

<160> NUMBER OF SEQ ID NOS: 104

<210> SEQ ID NO 1
<211> LENGTH: 432
<212> TYPE: DNA
<213> ORGANISM: Artificial Sequence
<220> FEATURE:
<223> OTHER INFORMATION: Nucleotide sequence of VH of mAb 2G1

<400> SEQUENCE: 1
atgggatgga gctggatctt tctcctcttc ctgtcaggaa ctgcaggtgt cctctctgag      60
gtccagctgc aacagtctgg accagagctg gtgaagcctg gggcttcagt gaagatatcc     120
tgcaaggctt ctggatacac aatcacagac tacaatttgg actgggtgaa gcagagccat     180
ggaaagagcc ttgagtggat tggagatatt agtcctaact atggttatac tatctacaac     240
cagaaattca aggacaaggc cacattgact gtagacaggt cctccagcac agcctacatg     300
gagctccgca gcctgacatc tgaggacact gcagtttatt actgtgcaag aagggacatt     360
cgttactccg gtaattccta caaatggtac ttcgatgtct ggggcacagg gaccacggtc     420
accgtctcct ca                                                         432

<210> SEQ ID NO 2
<211> LENGTH: 144
<212> TYPE: PRT
<213> ORGANISM: Artificial Sequence
<220> FEATURE:
<223> OTHER INFORMATION: Amino acid sequence of VH of mAb 2G1

<400> SEQUENCE: 2

Met Gly Trp Ser Trp Ile Phe Leu Leu Phe Leu Ser Gly Thr Ala Gly
  1               5                  10                  15

Val Leu Ser Glu Val Gln Leu Gln Gln Ser Gly Pro Glu Leu Val Lys
             20                  25                  30

Pro Gly Ala Ser Val Lys Ile Ser Cys Lys Ala Ser Gly Tyr Thr Ile
         35                  40                  45

Thr Asp Tyr Asn Leu Asp Trp Val Lys Gln Ser His Gly Lys Ser Leu
     50                  55                  60

Glu Trp Ile Gly Asp Ile Ser Pro Asn Tyr Gly Tyr Thr Ile Tyr Asn
 65                  70                  75                  80

Gln Lys Phe Lys Asp Lys Ala Thr Leu Thr Val Asp Arg Ser Ser Ser
                 85                  90                  95

Thr Ala Tyr Met Glu Leu Arg Ser Leu Thr Ser Glu Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Val Trp Gly Thr Gly Thr Thr Val Thr Val Ser Ser
```

<210> SEQ ID NO 3
<211> LENGTH: 10
<212> TYPE: PRT
<213> ORGANISM: Artificial Sequence
<220> FEATURE:
<223> OTHER INFORMATION: Amino acid sequence of CDR1 of VH of mAb 2G1

<400> SEQUENCE: 3

Gly Tyr Thr Ile Thr Asp Tyr Asn Leu Asp
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Amino acid sequence of CDR2 of VH of mAb 2G1

<400> SEQUENCE: 4

Asp Ile Ser Pro Asn Tyr Gly Tyr Thr Ile Tyr Asn Gln Lys Phe Lys
1               5                   10                  15

Asp

<210> SEQ ID NO 5
<211> LENGTH: 16
<212> TYPE: PRT
<213> ORGANISM: Artificial Sequence
<220> FEATURE:
<223> OTHER INFORMATION: Amino acid sequence of CDR3 of VH of mAb 2G1

<400> SEQUENCE: 5

Arg Asp Ile Arg Tyr Ser Gly Asn Ser Tyr Lys Trp Tyr Phe Asp Val
1               5                   10                  15

<210> SEQ ID NO 6
<211> LENGTH: 381
<212> TYPE: DNA
<213> ORGANISM: Artificial Sequence
<220> FEATURE:
<223> OTHER INFORMATION: Nucleotide sequence of VL of mAb 2G1

<400> SEQUENCE: 6
atgaggttcc aggttcaggt tctggggctc cttctgctct ggatatcagg tgcccagtgt      60
gatgtccaga taacccagtc tccatcttat cttgctgcat ctcctggaga aaccattact     120
attaattgca ggacaagtaa gagcataagc aaatatttag cctggtatca agagaaacct     180
gggaaaacta ataagcttct tatctactct ggatccacct tgcaatctgg aattccatca     240
aggttcaggg gcagtggatc tggtacagat ttcactctca ccatcagtag cctggagcct     300
gaagattttg caatgtatta ctgtcaacaa cataatgaat acccgtacac gttcggaggg     360
gggaccaagc tggaaataaa a                                               381

<210> SEQ ID NO 7
<211> LENGTH: 127
<212> TYPE: PRT
<213> ORGANISM: Artificial Sequence
<220> FEATURE:
<223> OTHER INFORMATION: Amino acid sequence of VL of mAb 2G1

<400> SEQUENCE: 7

Met Arg Phe Gln Val Gln Val Leu Gly Leu Leu Leu Leu Trp Ile Ser
1               5                   10                  15

```
Gly Ala Gln Cys Asp Val Gln Ile Thr Gln Ser Pro Ser Tyr Leu Ala
            20                  25                  30

Ala Ser Pro Gly Glu Thr Ile Thr Ile Asn Cys Arg Thr Ser Lys Ser
        35                  40                  45

Ile Ser Lys Tyr Leu Ala Trp Tyr Gln Glu Lys Pro Gly Lys Thr Asn
50                  55                  60

Lys Leu Leu Ile Tyr Ser Gly Ser Thr Leu Gln Ser Gly Ile Pro Ser
65                  70                  75                  80

Arg Phe Arg Gly Ser Gly Ser Gly Thr Asp Phe Thr Leu Thr Ile Ser
                85                  90                  95

Ser Leu Glu Pro Glu Asp Phe Ala Met Tyr Tyr Cys Gln Gln His Asn
            100                 105                 110

Glu Tyr Pro Tyr Thr Phe Gly Gly Gly Thr Lys Leu Glu Ile Lys
        115                 120                 125

<210> SEQ ID NO 8
<211> LENGTH: 11
<212> TYPE: PRT
<213> ORGANISM: Artificial Sequence
<220> FEATURE:
<223> OTHER INFORMATION: Amino acid sequence of CDR1 of VL of mAb 2G1

<400> SEQUENCE: 8

Arg Thr Ser Lys Ser Ile Ser Lys Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence of CDR2 of VL of mAb 2G1

<400> SEQUENCE: 9

Ser Gly Ser Thr Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence of CDR3 of VL of mAb 2G1

<400> SEQUENCE: 10

Gln Gln His Asn Glu Tyr Pro Tyr Thr
1               5

<210> SEQ ID NO 11
<211> LENGTH: 414
<212> TYPE: DNA
<213> ORGANISM: Artificial Sequence
<220> FEATURE:
<223> OTHER INFORMATION: Nucleotide sequence of VH of mAb 8E1

<400> SEQUENCE: 11
atggctgtcc tggggctgct tctctgcctg gtgactttcc caagctgtgt cctgtcccag      60
gtgcagctga aggagtcagg acctggcctg gtggcgccct cacagagcct gtccatcaca     120
tgcaccgtct cagggttccc tttaaacaac tatggaatac actgggttcg ccagcctcca     180
ggaaagggtc tggagtggct ggcagtgata tggagtgatg gaagaacaac ctataattca     240
```

```
gctctcaact ccagactgag catcagcaag acaactcca agagccaagt tttctttaaa      300
atgaacagtc tccaaactga tgacacagcc atgtactatt gtgccagaca tgatggtcgg      360
ggggactata gtatggacta ctggggtcaa ggaacctcag tcaccgtctc ctca            414
```

<210> SEQ ID NO 12
<211> LENGTH: 138
<212> TYPE: PRT
<213> ORGANISM: Artificial Sequence
<220> FEATURE:
<223> OTHER INFORMATION: Amino acid sequence of VH of mAb 8E1

<400> SEQUENCE: 12

```
Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Pro Leu
        35                  40                  45

Asn Asn Tyr Gly Ile His Trp Val Arg Gln Pro Pro Gly Lys Gly Leu
    50                  55                  60

Glu Trp Leu Ala Val Ile Trp Ser Asp Gly Arg Thr Thr Tyr Asn Ser
65                  70                  75                  80

Ala Leu Asn Ser Arg Leu Ser Ile Ser Lys Asp Asn Ser Lys Ser Gln
                85                  90                  95

Val Phe Phe Lys Met Asn Ser Leu Gln Thr Asp Asp Thr Ala Met Tyr
            100                 105                 110

Tyr Cys Ala Arg His Asp Gly Arg Gly Asp Tyr Ser Met Asp Tyr Trp
        115                 120                 125

Gly Gln Gly Thr Ser Val Thr Val Ser Ser
    130                 135
```

<210> SEQ ID NO 13
<211> LENGTH: 10
<212> TYPE: PRT
<213> ORGANISM: Artificial Sequence
<220> FEATURE:
<223> OTHER INFORMATION: Amino acid sequence of CDR1 of VH of mAb 8E1

<400> SEQUENCE: 13

```
Gly Phe Pro Leu Asn Asn Tyr Gly Ile His
1               5                   10
```

<210> SEQ ID NO 14
<211> LENGTH: 16
<212> TYPE: PRT
<213> ORGANISM: Artificial Sequence
<220> FEATURE:
<223> OTHER INFORMATION: Amino acid sequence of CDR2 of VH of mAb 8E1

<400> SEQUENCE: 14

```
Val Ile Trp Ser Asp Gly Arg Thr Thr Tyr Asn Ser Ala Leu Asn Ser
1               5                   10                  15
```

<210> SEQ ID NO 15
<211> LENGTH: 11
<212> TYPE: PRT
<213> ORGANISM: Artificial Sequence
<220> FEATURE:
<223> OTHER INFORMATION: Amino acid sequence of CDR3 of VH of mAb 8E1

<400> SEQUENCE: 15

His Asp Gly Arg Gly Asp Tyr Ser Met Asp Tyr
1               5                   10

<210> SEQ ID NO 16
<211> LENGTH: 390
<212> TYPE: DNA
<213> ORGANISM: Artificial Sequence
<220> FEATURE:
<223> OTHER INFORMATION: Nucleotide sequence of VL of mAb 8E1

<400> SEQUENCE: 16

```
atggagacag acacactcct gttatgggta ctgctgctct gggcccttag ttccgagctc    60
gtgatgacac agtctcctgc ttccttagtt gtatctctgg ggcagagggc caccatctca   120
tgcagggcca gcaaaggtgt cagtacatct gtctacagtt atatgcactg gtaccaacag   180
aaaccaggac agcccaccaa actcctcatc tatcttgcat ccaacctaga atctggggtc   240
cctgccaggt tcagtggcag tgggtctggg acagacttct ccctcaacat ccatcctgtg   300
gaggaggagg atgctgcaac ctattactgt cagcaaagtg gggagcttcc gctcacgttc   360
ggtgctggga ccaagctgga gctgaaacgg                                     390
```

<210> SEQ ID NO 17
<211> LENGTH: 130
<212> TYPE: PRT
<213> ORGANISM: Artificial Sequence
<220> FEATURE:
<223> OTHER INFORMATION: Amino acid sequence of VL of mAb 8E1

<400> SEQUENCE: 17

Met Glu Thr Asp Thr Leu Leu Leu Trp Val Leu Leu Leu Trp Ala Leu
1               5                   10                  15

Ser Ser Glu Leu Val Met Thr Gln Ser Pro Ala Ser Leu Val Val Ser
            20                  25                  30

Leu Gly Gln Arg Ala Thr Ile Ser Cys Arg Ala Ser Lys Gly Val Ser
        35                  40                  45

Thr Ser Val Tyr Ser Tyr Met His Trp Tyr Gln Gln Lys Pro Gly Gln
    50                  55                  60

Pro Pro Lys Leu Leu Ile Tyr Leu Ala Ser Asn Leu Glu Ser Gly Val
65                  70                  75                  80

Pro Ala Arg Phe Ser Gly Ser Gly Ser Gly Thr Asp Phe Ser Leu Asn
                85                  90                  95

Ile His Pro Val Glu Glu Glu Asp Ala Ala Thr Tyr Tyr Cys Gln Gln
            100                 105                 110

Ser Gly Glu Leu Pro Leu Thr Phe Gly Ala Gly Thr Lys Leu Glu Leu
        115                 120                 125

Lys Arg
    130

<210> SEQ ID NO 18
<211> LENGTH: 15
<212> TYPE: PRT
<213> ORGANISM: Artificial Sequence
<220> FEATURE:
<223> OTHER INFORMATION: Amino acid sequence of CDR1 of VL of mAb 8E1

<400> SEQUENCE: 18

Arg Ala Ser Lys Gly Val Ser Thr Ser Val Tyr Ser Tyr Met His
1               5                   10                  15

<210> SEQ ID NO 19

```
<211> LENGTH: 7
<212> TYPE: PRT
<213> ORGANISM: Artificial Sequence
<220> FEATURE:
<223> OTHER INFORMATION: Amino acid sequence of CDR2 of VL of mAb 8E1

<400> SEQUENCE: 19

Leu Ala Ser Asn Leu Glu Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Amino acid sequence of CDR3 of VL of mAb 8E1

<400> SEQUENCE: 20

Gln Gln Ser Gly Glu Leu Pro Leu Thr
1               5

<210> SEQ ID NO 21
<211> LENGTH: 429
<212> TYPE: DNA
<213> ORGANISM: Artificial Sequence
<220> FEATURE:
<223> OTHER INFORMATION: Nucleotide sequence of VH of mAb 4E7

<400> SEQUENCE: 21
atgtcctctc ctcagacact gaacacactg actctaacca tgggatggag ctggatcttt      60
ctctttctcc tgtcagaaac tgcaggagtc ctctctgagg tccagctgca acagggggct     120
tcagtgaaga tgtcctgtaa gacttctcga tactcattca ctgactacat catgcactgg     180
gtgaagctga gccatggaaa gagccttgag tggattggat atattaaccc taacaatggt     240
ggtactatct acaaccagaa gttcaaggac aaggccacat tgactgtaaa caagtcctcc     300
agcacagcct acatggaatt cgcagcctg acatcggagg attctgcagt ctatttctgt     360
tcaagagggg gggtttatta ccggggggttt gcttactggg gccaagggac actggtcact     420
gtctctgca                                                              429

<210> SEQ ID NO 22
<211> LENGTH: 143
<212> TYPE: PRT
<213> ORGANISM: Artificial Sequence
<220> FEATURE:
<223> OTHER INFORMATION: Amino acid sequence of VH of mAb 4E7

<400> SEQUENCE: 22

Met Ser Ser Pro Gln Thr Leu Asn Thr Leu Thr Leu Thr Met Gly Trp
1               5                   10                  15

Ser Trp Ile Phe Leu Phe Leu Leu Ser Glu Thr Ala Gly Val Leu Ser
            20                  25                  30

Glu Val Gln Leu Gln Gln Gly Ala Ser Val Lys Met Ser Cys Lys Thr
        35                  40                  45

Ser Arg Tyr Ser Phe Thr Asp Tyr Ile Met His Trp Val Lys Leu Ser
    50                  55                  60

His Gly Lys Ser Leu Glu Trp Ile Gly Tyr Ile Asn Pro Asn Asn Gly
65                  70                  75                  80

Gly Thr Ile Tyr Asn Gln Lys Phe Lys Asp Lys Ala Thr Leu Thr Val
                85                  90                  95

Asn Lys Ser Ser Ser Thr Ala Tyr Met Glu Phe Arg Ser Leu Thr Ser
```

```
                    100                 105                 110
Glu Asp Ser Ala Val Tyr Phe Cys Ser Arg Gly Gly Val Tyr Tyr Arg
            115                 120                 125

Gly Phe Ala Tyr Trp Gly Gln Gly Thr Leu Val Thr Val Ser Ala
        130                 135                 140
```

<210> SEQ ID NO 23
<211> LENGTH: 9
<212> TYPE: PRT
<213> ORGANISM: Artificial Sequence
<220> FEATURE:
<223> OTHER INFORMATION: Amino acid sequence of CDR1 of VH of mAb 4E7

<400> SEQUENCE: 23

```
Arg Tyr Ser Phe Thr Asp Tyr Ile Met
1               5
```

<210> SEQ ID NO 24
<211> LENGTH: 17
<212> TYPE: PRT
<213> ORGANISM: Artificial Sequence
<220> FEATURE:
<223> OTHER INFORMATION: Amino acid sequence of CDR2 of VH of mAb 4E7

<400> SEQUENCE: 24

```
Tyr Ile Asn Pro Asn Asn Gly Gly Thr Ile Tyr Asn Gln Lys Phe Lys
1               5                   10                  15

Asp
```

<210> SEQ ID NO 25
<211> LENGTH: 10
<212> TYPE: PRT
<213> ORGANISM: Artificial Sequence
<220> FEATURE:
<223> OTHER INFORMATION: Amino acid sequence of CDR3 of VH of mAb 4E7

<400> SEQUENCE: 25

```
Gly Gly Val Tyr Tyr Arg Gly Phe Ala Tyr
1               5                   10
```

<210> SEQ ID NO 26
<211> LENGTH: 411
<212> TYPE: DNA
<213> ORGANISM: Artificial Sequence
<220> FEATURE:
<223> OTHER INFORMATION: Nucleotide sequence of VL of mAb 4E7

<400> SEQUENCE: 26

```
atggcctgga tttcacttat actctctctc ctggctctca gctcaggggc catttcccag      60
gctgttgtga ctcaggaatc tgcactcacc acatcacctg gtgaaacagt cacattcact     120
tgtcgctcaa gtactggggc tgttacaaac agtaactatg ccaactgggt ccaagaaaaa     180
ccagatcatt ttttcactgg tctaataggt gttaccaaca accgaggtcc aggtgttcct     240
gcccgattct caggctccct gattggagac aaggctgccc tcaccatcac aggggcacag     300
actgaggatg aggcaatata tttctgtgct ctatggtaca gcaaccactt gggtgttcgg     360
tggaggaacc aaactgactg tcctaggcca gcccaagtct cgccatcag t               411
```

<210> SEQ ID NO 27
<211> LENGTH: 137
<212> TYPE: PRT
<213> ORGANISM: Artificial Sequence
<220> FEATURE:

<223> OTHER INFORMATION: Amino acid sequence of VL of mAb 4E7

<400> SEQUENCE: 27

Met Ala Trp Ile Ser Leu Ile Leu Ser Leu Leu Ala Leu Ser Ser Gly
1               5                   10                  15
Ala Ile Ser Gln Ala Val Val Thr Gln Glu Ser Ala Leu Thr Thr Ser
            20                  25                  30
Pro Gly Glu Thr Val Thr Phe Thr Cys Arg Ser Ser Thr Gly Ala Val
        35                  40                  45
Thr Asn Ser Asn Tyr Ala Asn Trp Val Gln Glu Lys Pro Asp His Phe
    50                  55                  60
Phe Thr Gly Leu Ile Gly Val Thr Asn Asn Arg Gly Pro Gly Val Pro
65                  70                  75                  80
Ala Arg Phe Ser Gly Ser Leu Ile Gly Asp Lys Ala Ala Leu Thr Ile
                85                  90                  95
Thr Gly Ala Gln Thr Glu Asp Glu Ala Ile Tyr Phe Cys Ala Leu Trp
            100                 105                 110
Tyr Ser Asn His Leu Gly Val Arg Trp Arg Asn Gln Thr Asp Cys Pro
        115                 120                 125
Arg Pro Ala Gln Val Phe Ala Ile Ser
    130                 135

<210> SEQ ID NO 28
<211> LENGTH: 14
<212> TYPE: PRT
<213> ORGANISM: Artificial Sequence
<220> FEATURE:
<223> OTHER INFORMATION: Amino acid sequence of CDR1 of VL of mAb 4E7

<400> SEQUENCE: 28

Arg Ser Ser Thr Gly Ala Val Thr Asn Ser Asn Tyr Ala Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Amino acid sequence of CDR2 of VL of mAb 4E7

<400> SEQUENCE: 29

Val Thr Asn Asn Arg Gly Pro
1               5

<210> SEQ ID NO 30
<211> LENGTH: 423
<212> TYPE: DNA
<213> ORGANISM: Artificial Sequence
<220> FEATURE:
<223> OTHER INFORMATION: Nucleotide sequence of VH of mAb 9G6

<400> SEQUENCE: 30
atggattggg tgtggacctt ggtattcctg atagcagctg cccaaagtgc ccaagcacag    60
atccagttgg tgcagtctgg acctgagctg aagaagcctg gagagacagt caagatctcc   120
tgcaaggctt ctgggtatac cttcacagaa tatccaatgc actgggtgaa gcaggctcca   180
ggaaagagtt tcaagtggat gggcatccta tacaccgaca ctggagagcc aacatatgct   240
gaagagttca gggacggtt tgccttctct ttggagacct ctgccagcac tgcctatttg   300
cagatcaaca acctcaaaaa tgaggacacg gctacatatt tctgtgttca ctcaggctac   360
gtaggctact ggggccaagg caccactctc acagtctcat cagccaaaac aacaccccca    420
tca                                                                  423

<210> SEQ ID NO 31
<211> LENGTH: 134
<212> TYPE: PRT
<213> ORGANISM: Artificial Sequence
<220> FEATURE:
<223> OTHER INFORMATION: Amino acid sequence of VH of mAb 9G6

<400> SEQUENCE: 31

Met Asp Trp Val Trp Thr Leu Val Phe Leu Ile Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Glu Tyr Pro Met His Trp Val Lys Gln Ala Pro Gly Lys Ser Phe
    50                  55                  60

Lys Trp Met Gly Ile Leu Tyr Thr Asp Thr Gly Glu Pro Thr Tyr Ala
65                  70                  75                  80

Glu Glu Phe Arg Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val His Ser Gly Tyr Val Gly Tyr Trp Gly Gln Gly Thr
        115                 120                 125

Thr Leu Thr Val Ser Ser
    130

<210> SEQ ID NO 32
<211> LENGTH: 10
<212> TYPE: PRT
<213> ORGANISM: Artificial Sequence
<220> FEATURE:
<223> OTHER INFORMATION: Amino acid sequence of CDR1 of VH of mAb 9G6

<400> SEQUENCE: 32

Gly Tyr Thr Phe Thr Glu Tyr Pro Met His
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Amino acid sequence of CDR2 of VH of mAb 9G6

<400> SEQUENCE: 33

Ile Leu Tyr Thr Asp Thr Gly Glu Pro Thr Tyr Ala Glu Glu Phe Arg
1               5                   10                  15

Gly

<210> SEQ ID NO 34
<211> LENGTH: 6
<212> TYPE: PRT
<213> ORGANISM: Artificial Sequence
<220> FEATURE:
<223> OTHER INFORMATION: Amino acid sequence of CDR3 of VH of mAb 9G6

<400> SEQUENCE: 34

<210> SEQ ID NO 35
<211> LENGTH: 384
<212> TYPE: DNA
<213> ORGANISM: Artificial Sequence
<220> FEATURE:
<223> OTHER INFORMATION: Nucleotide sequence of VL of mAb 9G6

<400> SEQUENCE: 35

```
atgagtgtgc ccactcaggt cctggggttg ctgctgctgt ggcttacagg tgccagatgt    60
gacatccaga tgactcagtc tccagcctcc ctatcagcat ctgtgggaga aactgtcacc   120
ttcacatgtc gggcaagtga gattatttac agttatttag tttggtatca gcagaaacag   180
ggaaaatctc ctcagctcct ggtctctaat gcaaaaacct agcagagggg tgtgccatca   240
aggttcagtg gcagtggatc aggcacacag tttttctctga agatcaatag cctgcagcct   300
gaagattttg ggagttatta ctgtcaacat tattatggta atcctcccac gttcggaggg   360
gggaccaagc tggaaataaa acgg                                           384
```

<210> SEQ ID NO 36
<211> LENGTH: 128
<212> TYPE: PRT
<213> ORGANISM: Artificial Sequence
<220> FEATURE:
<223> OTHER INFORMATION: Amino acid sequence of VL of mAb 9G6

<400> SEQUENCE: 36

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Phe Thr Cys Arg Ala Ser Glu Ile
        35                  40                  45

Ile Tyr Ser Tyr Leu Val Trp Tyr Gln Gln Lys Gln Gly Lys Ser Pro
    50                  55                  60

Gln Leu Leu Val Ser Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His Tyr Tyr
                100                 105                 110

Gly Asn Pro Pro Thr Phe Gly Gly Gly Thr Lys Leu Glu Ile Lys Arg
            115                 120                 125

<210> SEQ ID NO 37
<211> LENGTH: 11
<212> TYPE: PRT
<213> ORGANISM: Artificial Sequence
<220> FEATURE:
<223> OTHER INFORMATION: Amino acid sequence of CDR1 of VL of mAb 9G6

<400> SEQUENCE: 37

Arg Ala Ser Glu Ile Ile Tyr Ser Tyr Leu Val
1               5                   10

<210> SEQ ID NO 38
<211> LENGTH: 7
<212> TYPE: PRT
<213> ORGANISM: Artificial Sequence

```
<220> FEATURE:
<223> OTHER INFORMATION: Amino acid sequence of CDR2 of VL of mAb 9G6

<400> SEQUENCE: 38

Asn Ala Lys Thr Leu Ala Glu
1               5

<210> SEQ ID NO 39
<211> LENGTH: 9
<212> TYPE: PRT
<213> ORGANISM: Artificial Sequence
<220> FEATURE:
<223> OTHER INFORMATION: Amino acid sequence of CDR3 of VL of mAb 9G6

<400> SEQUENCE: 39

Gln His Tyr Tyr Gly Asn Pro Pro Thr
1               5

<210> SEQ ID NO 40
<211> LENGTH: 447
<212> TYPE: DNA
<213> ORGANISM: Artificial Sequence
<220> FEATURE:
<223> OTHER INFORMATION: Nucleotide sequence of VH of mAb 11C5

<400> SEQUENCE: 40
atgagcactg aacacggacc cctcaccatg aacttcgggc tcagcttgat tttccttgtc      60
cttgttttaa aggtgtcca gtgtgaagtg cagctagtgg agtctggggg aggcttagtg     120
aagcctggag gtccctgaa actctcctgt gcagcctctg gattcacttt cactacctat     180
gccatgtctt gggttcgcca gactccggaa agaggctgg agtgggtcgc aaccattagt     240
gctggtggta cttacaccta ctattcagac aatgtaaagg gccgattcac catctcccaga    300 gacaatgcca agaacaacct gtacctgcaa atgagccatc tgaagtctga ggacacagcc    360
atgttttact gtgcaagaga tcccgattac tacggtagaa gcccgtttgc ttactggggc    420
caagggactc tggtcactgt ctctgca                                         447

<210> SEQ ID NO 41
<211> LENGTH: 149
<212> TYPE: PRT
<213> ORGANISM: Artificial Sequence
<220> FEATURE:
<223> OTHER INFORMATION: Amino acid sequence of VH of mAb 11C5

<400> SEQUENCE: 41

Met Ser Thr Glu His Gly Pro Leu Thr Met Asn Phe Gly Leu Ser Leu
1               5                   10                  15

Ile Phe Leu Val Leu Val Leu Lys Gly Val Gln Cys Glu Val Gln Leu
            20                  25                  30

Val Glu Ser Gly Gly Gly Leu Val Lys Pro Gly Gly Ser Leu Lys Leu
        35                  40                  45

Ser Cys Ala Ala Ser Gly Phe Thr Phe Thr Thr Tyr Ala Met Ser Trp
    50                  55                  60

Val Arg Gln Thr Pro Glu Lys Arg Leu Glu Trp Val Ala Thr Ile Ser
65                  70                  75                  80

Ala Gly Gly Thr Tyr Thr Tyr Tyr Ser Asp Asn Val Lys Gly Arg Phe
                85                  90                  95

Thr Ile Ser Arg Asp Asn Ala Lys Asn Asn Leu Tyr Leu Gln Met Ser
            100                 105                 110

His Leu Lys Ser Glu Asp Thr Ala Met Phe Tyr Cys Ala Arg Asp Pro
```

```
                115                 120                 125
Asp Tyr Tyr Gly Arg Ser Pro Phe Ala Tyr Trp Gly Gln Gly Thr Leu
        130                 135                 140

Val Thr Val Ser Ala
145

<210> SEQ ID NO 42
<211> LENGTH: 10
<212> TYPE: PRT
<213> ORGANISM: Artificial Sequence
<220> FEATURE:
<223> OTHER INFORMATION: Amino acid sequence of CDR1 of VH of mAb 11C5

<400> SEQUENCE: 42

Gly Phe Thr Phe Thr Thr Tyr Ala Met Ser
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Amino acid sequence of CDR2 of VH of mAb 11C5

<400> SEQUENCE: 43

Thr Ile Ser Ala Gly Gly Thr Tyr Thr Tyr Tyr Ser Asp Asn Val Lys
1               5                   10                  15

Gly

<210> SEQ ID NO 44
<211> LENGTH: 12
<212> TYPE: PRT
<213> ORGANISM: Artificial Sequence
<220> FEATURE:
<223> OTHER INFORMATION: Amino acid sequence of CDR3 of VH of mAb 11C5

<400> SEQUENCE: 44

Asp Pro Asp Tyr Tyr Gly Arg Ser Pro Phe Ala Tyr
1               5                   10

<210> SEQ ID NO 45
<211> LENGTH: 384
<212> TYPE: DNA
<213> ORGANISM: Artificial Sequence
<220> FEATURE:
<223> OTHER INFORMATION: Nucleotide sequence of VL of mAb 11C5

<400> SEQUENCE: 45
atggttttca cacctcagat acttggactt atgctttttt ggatttcagc ctccagaggt      60
gaaattgtgc tcactcagtc tccagccacc ctgtctgtga ctccaggaga gagcgtcagt     120
ctttcctgta gggccagcca agtattagc aacaacctac agtggtatca acaaaaatca     180
catgagtctc caagacttct catcaaatat gcttcccagt ccatctctgg atcccctcc     240 aggttcagtg gcagtggatc aggacagat ttcactctca gtatcaacag tgtggagact     300
gaagattttg gaatgtattt ctgtcaacag agtaacagct ggcctctcac gttcggtggt     360
gggaccaagg tggagctgaa acgg                                            384

<210> SEQ ID NO 46
<211> LENGTH: 128
<212> TYPE: PRT
<213> ORGANISM: Artificial Sequence
<220> FEATURE:
```

<223> OTHER INFORMATION: Amino acid sequenceof VL of mAb 11C5

<400> SEQUENCE: 46

Met Val Phe Thr Pro Gln Ile Leu Gly Leu Met Leu Phe Trp Ile Ser
1               5                   10                  15

Ala Ser Arg Gly Glu Ile Val Leu Thr Gln Ser Pro Ala Thr Leu Ser
            20                  25                  30

Val Thr Pro Gly Glu Ser Val Ser Leu Ser Cys Arg Ala Ser Gln Ser
        35                  40                  45

Ile Ser Asn Asn Leu Gln Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Ser Asn
            100                 105                 110

Ser Trp Pro Leu Thr Phe Gly Gly Gly Thr Lys Val Glu Leu Lys Arg
        115                 120                 125

<210> SEQ ID NO 47
<211> LENGTH: 11
<212> TYPE: PRT
<213> ORGANISM: Artificial Sequence
<220> FEATURE:
<223> OTHER INFORMATION: Amino acid sequence of CDR1 of VL of mAb 11C5

<400> SEQUENCE: 47

Arg Ala Ser Gln Ser Ile Ser Asn Asn Leu Gln
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Amino acid sequence of CDR2 of VL of mAb 11C5

<400> SEQUENCE: 48

Tyr Ala Ser Gln Ser Ile Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Amino acid sequence of CDR3 of VL of mAb 11C5

<400> SEQUENCE: 49

Gln Gln Ser Asn Ser Trp Pro Leu Thr
1               5

<210> SEQ ID NO 50
<211> LENGTH: 465
<212> TYPE: DNA
<213> ORGANISM: Artificial Sequence
<220> FEATURE:
<223> OTHER INFORMATION: Nucleotide sequence of VH of mAb 11D9

<400> SEQUENCE: 50
atgtcctcac cacagacact gaacacactg actctaacca tgggatggag ctggatcttt      60

```
ctctttctcc tgtcaggaac tgcaggtgtc ctctctgagg tccagctgca acaatctgga    120
cctgaggtgg tgaagcctgg ggcttcagtg aagatatcct gtaaggcttc tggatacacg    180
ttcactgact tctacatgaa ctgggtgaaa cagagccatg gaaagagcct tgagtggatt    240
ggatatatta atcctaacaa tggtgatact agttacaacc agaagttcaa gggcaaggcc    300
acatcgactg tagacaggtc ctccaacaca gcctacatgg agctccgcag cctgacatct    360
gaggactctg cagtctatta ctgtgcaaga ctcatcttct atggtaactg gtactttgat    420
gtctggggca cagggaccac ggtcaccgtc tcctcagcca aaaca                    465
```

<210> SEQ ID NO 51
<211> LENGTH: 155
<212> TYPE: PRT
<213> ORGANISM: Artificial Sequence
<220> FEATURE:
<223> OTHER INFORMATION: Amino acid sequence of VH of mAb 11D9

<400> SEQUENCE: 51

```
Met Ser Ser Pro Gln Thr Leu Asn Thr Leu Thr Leu Thr Met Gly Trp
1               5                   10                  15

Ser Trp Ile Phe Leu Phe Leu Leu Ser Gly Thr Ala Gly Val Leu Ser
            20                  25                  30

Glu Val Gln Leu Gln Gln Ser Gly Pro Glu Val Val Lys Pro Gly Ala
        35                  40                  45

Ser Val Lys Ile Ser Cys Lys Ala Ser Gly Tyr Thr Phe Thr Asp Phe
    50                  55                  60

Tyr Met Asn Trp Val Lys Gln Ser His Gly Lys Ser Leu Glu Trp Ile
65                  70                  75                  80

Gly Tyr Ile Asn Pro Asn Asn Gly Asp Thr Ser Tyr Asn Gln Lys Phe
                85                  90                  95

Lys Gly Lys Ala Thr Ser Thr Val Asp Arg Ser Ser Asn Thr Ala Tyr
            100                 105                 110

Met Glu Leu Arg Ser Leu Thr Ser Glu Asp Ser Ala Val Tyr Tyr Cys
        115                 120                 125

Ala Arg Leu Ile Phe Tyr Gly Asn Trp Tyr Phe Asp Val Trp Gly Thr
    130                 135                 140

Gly Thr Thr Val Thr Val Ser Ser Ala Lys Thr
145                 150                 155
```

<210> SEQ ID NO 52
<211> LENGTH: 10
<212> TYPE: PRT
<213> ORGANISM: Artificial Sequence
<220> FEATURE:
<223> OTHER INFORMATION: Amino acid sequence of CDR1 of VH of mAb 11D9

<400> SEQUENCE: 52

```
Gly Tyr Thr Phe Thr Asp Phe Tyr Met Asn
1               5                   10
```

<210> SEQ ID NO 53
<211> LENGTH: 17
<212> TYPE: PRT
<213> ORGANISM: Artificial Sequence
<220> FEATURE:
<223> OTHER INFORMATION: Amino acid sequence of CDR2 of VH of mAb 11D9

<400> SEQUENCE: 53

```
Tyr Ile Asn Pro Asn Asn Gly Asp Thr Ser Tyr Asn Gln Lys Phe Lys
1               5                   10                  15
```

Gly

<210> SEQ ID NO 54
<211> LENGTH: 11
<212> TYPE: PRT
<213> ORGANISM: Artificial Sequence
<220> FEATURE:
<223> OTHER INFORMATION: Amino acid sequence of CDR3 of VH of mAb 11D9

<400> SEQUENCE: 54

```
Leu Ile Phe Tyr Gly Asn Trp Tyr Phe Asp Val
1               5                   10
```

<210> SEQ ID NO 55
<211> LENGTH: 393
<212> TYPE: DNA
<213> ORGANISM: Artificial Sequence
<220> FEATURE:
<223> OTHER INFORMATION: Nucleotide sequence of VL of mAb 11D9

<400> SEQUENCE: 55

```
atggattttc agatgcagat tatcagcttg ctgctaatca gtgtcacagt catagtgtct      60
aatgagaaa ttgtgctcac ccagtctcca cccaccatgg ctgcatctcc cggggagaag     120
atcactatca cctgcagtgc cagctcaagt ataagttcca attacgtgca ttggtatcag    180
cagaagccag gattctcccc taaactcttg atttatagga catccaatct ggcttctgga    240
gtcccagttc gcttcagtgg cagtgggtct gggacctctt actctctcac aattggcacc    300
atggaggctg aagatgttgc cacttactac tgccagcagg gtactagtat accgtggacg    360
ttcggtggag gcaccaaggt ggaaattaat cgg                                  393
```

<210> SEQ ID NO 56
<211> LENGTH: 131
<212> TYPE: PRT
<213> ORGANISM: Artificial Sequence
<220> FEATURE:
<223> OTHER INFORMATION: Amino acid sequence of VL of mAb 11D9

<400> SEQUENCE: 56

```
Met Asp Phe Gln Met Gln Ile Ile Ser Leu Leu Leu Ile Ser Val Thr
1               5                   10                  15

Val Ile Val Ser Asn Gly Glu Ile Val Leu Thr Gln Ser Pro Pro Thr
            20                  25                  30

Met Ala Ala Ser Pro Gly Glu Lys Ile Thr Ile Thr Cys Ser Ala Ser
        35                  40                  45

Ser Ser Ile Ser Ser Asn Tyr Val His Trp Tyr Gln Gln Lys Pro Gly
    50                  55                  60

Phe Ser Pro Lys Leu Leu Ile Tyr Arg Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Gly Thr Met Glu Ala Glu Asp Val Ala Thr Tyr Tyr Cys Gln
            100                 105                 110

Gln Gly Thr Ser Ile Pro Trp Thr Phe Gly Gly Gly Thr Lys Val Glu
        115                 120                 125

Ile Asn Arg
    130
```

<210> SEQ ID NO 57

```
<211> LENGTH: 12
<212> TYPE: PRT
<213> ORGANISM: Artificial Sequence
<220> FEATURE:
<223> OTHER INFORMATION: Amino acid sequence of CDR1 of VL of mAb 11D9

<400> SEQUENCE: 57

Ser Ala Ser Ser Ser Ile Ser Ser Asn Tyr Val His
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Amino acid sequence of CDR2 of VL of mAb 11D9

<400> SEQUENCE: 58

Arg Thr Ser Asn Leu Ala Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Amino acid sequence of CDR3 of VL of mAb 11D9

<400> SEQUENCE: 59

Gln Gln Gly Thr Ser Ile Pro Trp Thr
1               5

<210> SEQ ID NO 60
<211> LENGTH: 327
<212> TYPE: PRT
<213> ORGANISM: Artificial Sequence
<220> FEATURE:
<223> OTHER INFORMATION: Amino acid sequence of human IgG4 Constant
      Heavy chain region with S228P mutation

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                165                 170                 175
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 61
<211> LENGTH: 106
<212> TYPE: PRT
<213> ORGANISM: Artificial Sequence
<220> FEATURE:
<223> OTHER INFORMATION: Amino acid sequence of human Kappa Constant
      Light region

<400> SEQUENCE: 61

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 62
<211> LENGTH: 432
<212> TYPE: DNA
<213> ORGANISM: Artificial Sequence
<220> FEATURE:
<223> OTHER INFORMATION: Nucleotide sequence of Humanized 2G1 VH-11801

<400> SEQUENCE: 62
atggactgga cctgggtctt tctcttcctc ctgtcagtaa ctgcaggtgt ccactcccag    60
gttcagctgg tgcagtctgg agctgaggtg aagaagcctg gggcctcagt gaaggtctcc   120
tgcaaggctt ctggatacac aatcacagac tacaatttgg actgggtgcg acaggcccct   180
```
ggacaagggc ttgagtggat gggagatatt agtcctaact atggttatac tatctacaac    240
cagaaattca aggacagagt caccatgacc acagacacat ccacgagcac agcctacatg    300
gagctgagga gcctgagatc tgacgacacg gccgtgtatt actgtgcgag aagggacatt    360
cgttactccg gtaattccta caatggtac ttcgatgtct ggggccaagg gacaatggtc    420
accgtctctt ca    432

<210> SEQ ID NO 63
<211> LENGTH: 144
<212> TYPE: PRT
<213> ORGANISM: Artificial Sequence
<220> FEATURE:
<223> OTHER INFORMATION: Amino acid sequence of Humanized 2G1 VH-11801

<400> SEQUENCE: 63

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Ile
        35                  40                  45

Thr Asp Tyr Asn Leu Asp Trp Val Arg Gln Ala Pro Gly Gln Gly Leu
    50                  55                  60

Glu Trp Met Gly Asp Ile Ser Pro Asn Tyr Gly Tyr Thr Ile Tyr Asn
65                  70                  75                  80

Gln Lys Phe Lys Asp Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Val Trp Gly Gln Gly Thr Met Val Thr Val Ser Ser
    130                 135                 140

<210> SEQ ID NO 64
<211> LENGTH: 10
<212> TYPE: PRT
<213> ORGANISM: Artificial Sequence
<220> FEATURE:
<223> OTHER INFORMATION: Amino acid sequence of CDR1 of Humanized 2G1
      VH-11801

<400> SEQUENCE: 64

Gly Tyr Thr Ile Thr Asp Tyr Asn Leu Asp
1               5                   10

<210> SEQ ID NO 65
<211> LENGTH: 18
<212> TYPE: PRT
<213> ORGANISM: Artificial Sequence
<220> FEATURE:
<223> OTHER INFORMATION: Amino acid sequence of CDR2 of Humanized 2G1
      VH-11801

<400> SEQUENCE: 65

Gly Asp Ile Ser Pro Asn Tyr Gly Tyr Thr Ile Tyr Asn Gln Lys Phe
1               5                   10                  15

Lys Asp

<210> SEQ ID NO 66
<211> LENGTH: 16
<212> TYPE: PRT
<213> ORGANISM: Artificial Sequence
<220> FEATURE:
<223> OTHER INFORMATION: Amino acid sequence of CDR3 of Humanized 2G1 VH-11801

<400> SEQUENCE: 66

Arg Asp Ile Arg Tyr Ser Gly Asn Ser Tyr Lys Trp Tyr Phe Asp Val
1               5                   10                  15

<210> SEQ ID NO 67
<211> LENGTH: 432
<212> TYPE: DNA
<213> ORGANISM: Artificial Sequence
<220> FEATURE:
<223> OTHER INFORMATION: Nucleotide sequence of Humanized 2G1 VH-16901

<400> SEQUENCE: 67
atggactgga cctgggtctt tctcttcctc ctgtcagtaa ctgcaggtgt ccactcccag      60
gtgcagctgg tgcagtctgg ggctgaggtg aagaagcctg gtcctcggt gaaggtctcc      120 tgcaaggctt ctggatacac aatcacagac tacaatttgg actgggtgcg acaggccct      180 ggacaagggc ttgagtggat gggagatatt agtcctaact atggttatac tatctacaac      240
cagaaattca aggacagagt cacgattacc gcggacgaat ccacgagcac agcctacatg      300
gagctgagca gcctgagatc tgaggacacg gccgtgtatt actgtgcgag aagggacatt      360
cgttactccg gtaattccta caaatggtac ttcgatgtct ggggccaagg gacaatggtc      420
accgtctctt ca                                                          432

<210> SEQ ID NO 68
<211> LENGTH: 144
<212> TYPE: PRT
<213> ORGANISM: Artificial Sequence
<220> FEATURE:
<223> OTHER INFORMATION: Amino acid sequence of Humanized 2G1 VH-16901

<400> SEQUENCE: 68

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Ile
            35                  40                  45

Thr Asp Tyr Asn Leu Asp Trp Val Arg Gln Ala Pro Gly Gln Gly Leu
        50                  55                  60

Glu Trp Met Gly Asp Ile Ser Pro Asn Tyr Gly Tyr Thr Ile Tyr Asn
65                  70                  75                  80

Gln Lys Phe Lys Asp Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Arg Tyr Ser Gly Asn Ser Tyr Lys
        115                 120                 125

Trp Tyr Phe Asp Val Trp Gly Gln Gly Thr Met Val Thr Val Ser Ser
    130                 135                 140

<210> SEQ ID NO 69
<211> LENGTH: 10

<212> TYPE: PRT
<213> ORGANISM: Artificial Sequence
<220> FEATURE:
<223> OTHER INFORMATION: Amino acid sequence of CDR1 of Humanized 2G1
      VH-16901

<400> SEQUENCE: 69

Gly Tyr Thr Ile Thr Asp Tyr Asn Leu Asp
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Amino acid sequence of CDR2 of Humanized 2G1
      VH-16901

<400> SEQUENCE: 70

Asp Ile Ser Pro Asn Tyr Gly Tyr Thr Ile Tyr Asn Gln Lys Phe Lys
1               5                   10                  15

Asp

<210> SEQ ID NO 71
<211> LENGTH: 16
<212> TYPE: PRT
<213> ORGANISM: Artificial Sequence
<220> FEATURE:
<223> OTHER INFORMATION: Amino acid sequence of CDR3 of Humanized 2G1
      VH-16901

<400> SEQUENCE: 71

Arg Asp Ile Arg Tyr Ser Gly Asn Ser Tyr Lys Trp Tyr Phe Asp Val
1               5                   10                  15

<210> SEQ ID NO 72
<211> LENGTH: 381
<212> TYPE: DNA
<213> ORGANISM: Artificial Sequence
<220> FEATURE:
<223> OTHER INFORMATION: Nucleotide sequence of Humanized 2G1 VL-1901

<400> SEQUENCE: 72
atggaagccc cagctcagct tctcttcctc ctgctactct ggctcccaga taccaccgga      60
gacatccagt tgacccagtc tccatccttc tgtctgcat ctgtaggaga cagagtcacc      120
atcacttgca ggacaagtaa gagcataagc aaatatttag cctggtatca gcaaaaacca     180
gggaaagccc ctaagctcct gatctattct ggatccacct tgcaatctgg ggtcccatca     240
aggttcagcg gcagtggatc tgggacagaa ttcactctca caatcagcag cctgcagcct    300
gaagattttg caactcatta ctgtcaacaa cataatgaat cccgtacac gtttggccag    360 gggaccaagc tggagatcaa a                                              381

<210> SEQ ID NO 73
<211> LENGTH: 127
<212> TYPE: PRT
<213> ORGANISM: Artificial Sequence
<220> FEATURE:
<223> OTHER INFORMATION: Amino acid sequence of Humanized 2G1 VL-1901

<400> SEQUENCE: 73

Met Glu Ala Pro Ala Gln Leu Leu Phe Leu Leu Leu Leu Trp Leu Pro
1               5                   10                  15

Asp Thr Thr Gly Asp Ile Gln Leu Thr Gln Ser Pro Ser Phe Leu Ser

```
                   20                  25                  30
Ala Ser Val Gly Asp Arg Val Thr Ile Thr Cys Arg Thr Ser Lys Ser
            35                  40                  45

Ile Ser Lys Tyr Leu Ala Trp Tyr Gln Gln Lys Pro Gly Lys Ala Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Gln Gln His Asn
            100                 105                 110

Glu Tyr Pro Tyr Thr Phe Gly Gln Gly Thr Lys Leu Glu Ile Lys
        115                 120                 125

<210> SEQ ID NO 74
<211> LENGTH: 11
<212> TYPE: PRT
<213> ORGANISM: Artificial Sequence
<220> FEATURE:
<223> OTHER INFORMATION: Amino acid sequence of CDR1 of Humanized 2G1
      VL-1901

<400> SEQUENCE: 74

Arg Thr Ser Lys Ser Ile Ser Lys Tyr Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Amino acid sequence of CDR2 of Humanized 2G1
      VL-1901

<400> SEQUENCE: 75

Ser Gly Ser Thr Leu Gln Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Amino acid sequence of CDR3 of Humanized 2G1
      VL-1901

<400> SEQUENCE: 76

Gln Gln His Asn Glu Tyr Pro Tyr Thr
1               5

<210> SEQ ID NO 77
<211> LENGTH: 24
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (19)..(19)
<223> OTHER INFORMATION: A or T
<220> FEATURE:
<221> NAME/KEY: misc_feature
<222> LOCATION: (21)..(21)
<223> OTHER INFORMATION: A or T

<400> SEQUENCE: 77
```

```
gaggtgaagc tggtggagnc nagg                                          24
```

<210> SEQ ID NO 78
<211> LENGTH: 17
<212> TYPE: DNA
<213> ORGANISM: Artificial Sequence
<220> FEATURE:
<223> OTHER INFORMATION: PCR primer

<400> SEQUENCE: 78

```
ggggccagtg gatagac                                                  17
```

<210> SEQ ID NO 79
<211> LENGTH: 32
<212> TYPE: DNA
<213> ORGANISM: Artificial Sequence
<220> FEATURE:
<223> OTHER INFORMATION: PCR primer

<400> SEQUENCE: 79

```
ccagttccga gctccagatg acccagactc ca                                 32
```

<210> SEQ ID NO 80
<211> LENGTH: 32
<212> TYPE: DNA
<213> ORGANISM: Artificial Sequence
<220> FEATURE:
<223> OTHER INFORMATION: PCR primer

<400> SEQUENCE: 80

```
ccagttccga gctcgtgctc acccagtctc ca                                 32
```

<210> SEQ ID NO 81
<211> LENGTH: 32
<212> TYPE: DNA
<213> ORGANISM: Artificial Sequence
<220> FEATURE:
<223> OTHER INFORMATION: PCR primer

<400> SEQUENCE: 81

```
ccagttccga gctccagatg acccagtctc ca                                 32
```

<210> SEQ ID NO 82
<211> LENGTH: 32
<212> TYPE: DNA
<213> ORGANISM: Artificial Sequence
<220> FEATURE:
<223> OTHER INFORMATION: PCR primer

<400> SEQUENCE: 82

```
ccagttccga gctcgtgatg acacagtctc ca                                 32
```

<210> SEQ ID NO 83
<211> LENGTH: 17
<212> TYPE: DNA
<213> ORGANISM: Artificial Sequence
<220> FEATURE:
<223> OTHER INFORMATION: PCR primer

<400> SEQUENCE: 83

```
gttggtgcag catcagc                                                  17
```

<210> SEQ ID NO 84
<211> LENGTH: 104
<212> TYPE: PRT

<213> ORGANISM: Homo sapiens

<400> SEQUENCE: 84

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
            20                  25                  30

Asp Ala Thr Ile Ser Ile Lys Ser Tyr Pro Asp Lys Lys Phe Ser Tyr
        35                  40                  45

Ser Ser Gly His Val His Leu Ser Ser Glu Asn Lys Phe Gln Asn Ser
    50                  55                  60

Ala Ile Leu Thr Ile Gln Pro Lys Gln Leu Pro Gly Gly Gln Asn Pro
65                  70                  75                  80

Val Ser Tyr Val Tyr Leu Glu Val Val Ser Lys His Phe Ser Lys Ser
                85                  90                  95

Lys Arg Met Pro Ile Thr Tyr Asp
            100

<210> SEQ ID NO 85
<211> LENGTH: 101
<212> TYPE: PRT
<213> ORGANISM: Homo sapiens

<400> SEQUENCE: 85

Asn Gly Phe Leu Phe Ile His Thr Asp Lys Pro Val Tyr Thr Pro Asp
1               5                   10                  15

Gln Ser Val Lys Val Arg Val Tyr Ser Leu Asn Asp Asp Leu Lys Pro
            20                  25                  30

Ala Lys Arg Glu Thr Val Leu Thr Phe Ile Asp Pro Glu Gly Ser Glu
        35                  40                  45

Val Asp Met Val Glu Glu Ile Asp His Ile Gly Ile Ile Ser Phe Pro
    50                  55                  60

Asp Phe Lys Ile Pro Ser Asn Pro Arg Tyr Gly Met Trp Thr Ile Lys
65                  70                  75                  80

Ala Lys Tyr Lys Glu Asp Phe Ser Thr Thr Gly Thr Ala Tyr Phe Glu
                85                  90                  95

Val Lys Glu Tyr Val
            100

<210> SEQ ID NO 86
<211> LENGTH: 127
<212> TYPE: PRT
<213> ORGANISM: Homo sapiens

<400> SEQUENCE: 86

Leu Pro His Phe Ser Val Ser Ile Glu Pro Glu Tyr Asn Phe Ile Gly
1               5                   10                  15

Tyr Lys Asn Phe Lys Asn Phe Glu Ile Thr Ile Lys Ala Arg Tyr Phe
            20                  25                  30

Tyr Asn Lys Val Val Thr Glu Ala Asp Val Tyr Ile Thr Phe Gly Ile
        35                  40                  45

Arg Glu Asp Leu Lys Asp Asp Gln Lys Glu Met Met Gln Thr Ala Met
    50                  55                  60

Gln Asn Thr Met Leu Ile Asn Gly Ile Ala Gln Val Thr Phe Asp Ser
65                  70                  75                  80

Glu Thr Ala Val Lys Glu Leu Ser Tyr Tyr Ser Leu Glu Asp Leu Asn
                85                  90                  95

```
Asn Lys Tyr Leu Tyr Ile Ala Val Thr Val Ile Glu Ser Thr Gly Gly
            100                 105                 110

Phe Ser Glu Glu Ala Glu Ile Pro Gly Ile Lys Tyr Val Leu Ser
        115                 120                 125

<210> SEQ ID NO 87
<211> LENGTH: 108
<212> TYPE: PRT
<213> ORGANISM: Homo sapiens

<400> SEQUENCE: 87

Pro Tyr Lys Leu Asn Leu Val Ala Thr Pro Leu Phe Leu Lys Pro Gly
1               5                   10                  15

Ile Pro Tyr Pro Ile Lys Val Gln Val Lys Asp Ser Leu Asp Gln Leu
            20                  25                  30

Val Gly Gly Val Pro Val Thr Leu Asn Ala Gln Thr Ile Asp Val Asn
        35                  40                  45

Gln Glu Thr Ser Asp Leu Asp Pro Ser Lys Ser Val Thr Arg Val Asp
    50                  55                  60

Asp Gly Val Ala Ser Phe Val Leu Asn Leu Pro Ser Gly Val Thr Val
65                  70                  75                  80

Leu Glu Phe Asn Val Lys Thr Asp Ala Pro Asp Leu Pro Glu Glu Asn
                85                  90                  95

Gln Ala Arg Glu Gly Tyr Arg Ala Ile Ala Tyr Ser
            100                 105

<210> SEQ ID NO 88
<211> LENGTH: 108
<212> TYPE: PRT
<213> ORGANISM: Homo sapiens

<400> SEQUENCE: 88

Ser Leu Ser Gln Ser Tyr Leu Tyr Ile Asp Trp Thr Asp Asn His Lys
1               5                   10                  15

Ala Leu Leu Val Gly Glu His Leu Asn Ile Ile Val Thr Pro Lys Ser
            20                  25                  30

Pro Tyr Ile Asp Lys Ile Thr His Tyr Asn Tyr Leu Ile Leu Ser Lys
        35                  40                  45

Gly Lys Ile Ile His Phe Gly Thr Arg Glu Lys Phe Ser Asp Ala Ser
    50                  55                  60

Tyr Gln Ser Ile Asn Ile Pro Val Thr Gln Asn Met Val Pro Ser Ser
65                  70                  75                  80

Arg Leu Leu Val Tyr Tyr Ile Val Thr Gly Glu Gln Thr Ala Glu Leu
                85                  90                  95

Val Ser Asp Ser Val Trp Leu Asn Ile Glu Glu Lys
            100                 105

<210> SEQ ID NO 89
<211> LENGTH: 107
<212> TYPE: PRT
<213> ORGANISM: Homo sapiens

<400> SEQUENCE: 89

Cys Gly Asn Gln Leu Gln Val His Leu Ser Pro Asp Ala Asp Ala Tyr
1               5                   10                  15

Ser Pro Gly Gln Thr Val Ser Leu Asn Met Ala Thr Gly Met Asp Ser
            20                  25                  30
```

```
Trp Val Ala Leu Ala Ala Val Asp Ser Ala Val Tyr Gly Val Gln Arg
            35                  40                  45

Gly Ala Lys Lys Pro Leu Glu Arg Val Phe Gln Phe Leu Glu Lys Ser
 50                  55                  60

Asp Leu Gly Cys Gly Ala Gly Gly Leu Asn Asn Ala Asn Val Phe
 65                  70                  75                  80

His Leu Ala Gly Leu Thr Phe Leu Thr Asn Ala Asn Ala Asp Ser
                85                  90                  95

Gln Glu Asn Asp Glu Pro Cys Lys Glu Ile Leu
            100                 105
```

<210> SEQ ID NO 90
<211> LENGTH: 24
<212> TYPE: DNA
<213> ORGANISM: Artificial Sequence
<220> FEATURE:
<223> OTHER INFORMATION: PCR Primer

<400> SEQUENCE: 90
tccccaggtt ttccccagga agat         24

<210> SEQ ID NO 91
<211> LENGTH: 23
<212> TYPE: DNA
<213> ORGANISM: Artificial Sequence
<220> FEATURE:
<223> OTHER INFORMATION: PCR primer

<400> SEQUENCE: 91
aatggatttc tcttcattca tac          23

<210> SEQ ID NO 92
<211> LENGTH: 22
<212> TYPE: DNA
<213> ORGANISM: Artificial Sequence
<220> FEATURE:
<223> OTHER INFORMATION: PCR primer

<400> SEQUENCE: 92
gtcataggtt attggcattc tt           22

<210> SEQ ID NO 93
<211> LENGTH: 24
<212> TYPE: DNA
<213> ORGANISM: Artificial Sequence
<220> FEATURE:
<223> OTHER INFORMATION: PCR primer

<400> SEQUENCE: 93
ttgccacatt tttctgtctc aatc         24

<210> SEQ ID NO 94
<211> LENGTH: 26
<212> TYPE: DNA
<213> ORGANISM: Artificial Sequence
<220> FEATURE:
<223> OTHER INFORMATION: PCR primer

<400> SEQUENCE: 94
gacatattct ttaacttcaa aatatg       26

<210> SEQ ID NO 95
<211> LENGTH: 22
<212> TYPE: DNA

```
<213> ORGANISM: Artificial Sequence
<220> FEATURE:
<223> OTHER INFORMATION: PCR primer

<400> SEQUENCE: 95
ccctacaaac tgaatttggt tg                                              22

<210> SEQ ID NO 96
<211> LENGTH: 23
<212> TYPE: DNA
<213> ORGANISM: Artificial Sequence
<220> FEATURE:
<223> OTHER INFORMATION: PCR primer

<400> SEQUENCE: 96
agagaggaca tatttgatgc cag                                             23

<210> SEQ ID NO 97
<211> LENGTH: 21
<212> TYPE: DNA
<213> ORGANISM: Artificial Sequence
<220> FEATURE:
<223> OTHER INFORMATION: PCR primer

<400> SEQUENCE: 97
tctctcagcc aaagttacct t                                               21

<210> SEQ ID NO 98
<211> LENGTH: 23
<212> TYPE: DNA
<213> ORGANISM: Artificial Sequence
<220> FEATURE:
<223> OTHER INFORMATION: PCR primer

<400> SEQUENCE: 98
tgagtatgct attgctcggt aac                                             23

<210> SEQ ID NO 99
<211> LENGTH: 22
<212> TYPE: DNA
<213> ORGANISM: Artificial Sequence
<220> FEATURE:
<223> OTHER INFORMATION: PCR primer

<400> SEQUENCE: 99
tgtggcaacc agctccaggt tc                                              22

<210> SEQ ID NO 100
<211> LENGTH: 22
<212> TYPE: DNA
<213> ORGANISM: Artificial Sequence
<220> FEATURE:
<223> OTHER INFORMATION: PCR primer

<400> SEQUENCE: 100
ttttctttca atatttaacc ag                                              22

<210> SEQ ID NO 101
<211> LENGTH: 24
<212> TYPE: DNA
<213> ORGANISM: Artificial Sequence
<220> FEATURE:
<223> OTHER INFORMATION: PCR primer

<400> SEQUENCE: 101
aggccaagaa gaacgctgca aaag                                            24
```

<210> SEQ ID NO 102
<211> LENGTH: 41
<212> TYPE: DNA
<213> ORGANISM: Artificial Sequence
<220> FEATURE:
<223> OTHER INFORMATION: PCR primer

<400> SEQUENCE: 102
ttttggcaaa gaattcgcca ccatgggcct tttgggaata c        41

<210> SEQ ID NO 103
<211> LENGTH: 58
<212> TYPE: DNA
<213> ORGANISM: Artificial Sequence
<220> FEATURE:
<223> OTHER INFORMATION: PCR primer

<400> SEQUENCE: 103
cctgaggagt gaattcttaa tggtgatggt gatggtggag aatttcttta caaggttc    58

<210> SEQ ID NO 104
<211> LENGTH: 327
<212> TYPE: PRT
<213> ORGANISM: Artificial Sequence
<220> FEATURE:
<223> OTHER INFORMATION: Amino acid sequence of human IgG4 Constant
      Heavy chain region

<400> SEQUENCE: 104

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys

```
225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Pro Gly Lys
                325
```